(12) United States Patent
Beaton et al.

(10) Patent No.: US 11,866,421 B2
(45) Date of Patent: Jan. 9, 2024

(54) PYRIMIDINE AND PYRIDINE AMINE COMPOUNDS AND USAGE THEREOF IN DISEASE TREATMENT

(71) Applicant: Epigen Biosciences, Inc., San Diego, CA (US)

(72) Inventors: Graham Beaton, Vista, CA (US);
Fabio Tucci, San Diego, CA (US);
Satheesh Ravula, San Diego, CA (US);
Suk Joong Lee, San Diego, CA (US);
Chandravadan Shah, San Diego, CA (US)

(73) Assignee: Epigen Biosciences, INC., San Diego, CA (US)

( * ) Notice: Subject to any disclaimer, the term of this patent is extended or adjusted under 35 U.S.C. 154(b) by 0 days.

(21) Appl. No.: 17/334,921

(22) Filed: May 31, 2021

(65) Prior Publication Data

US 2022/0396564 A1    Dec. 15, 2022

(51) Int. Cl.
*C07D 403/04*    (2006.01)
*C07D 401/04*    (2006.01)
*C07D 405/14*    (2006.01)

(52) U.S. Cl.
CPC ......... *C07D 403/04* (2013.01); *C07D 401/04* (2013.01); *C07D 405/14* (2013.01)

(58) Field of Classification Search
CPC ... C07D 403/04; C07D 401/04; C07D 405/14
See application file for complete search history.

(56) References Cited

U.S. PATENT DOCUMENTS

| | | | |
|---|---|---|---|
| 8,946,247 B2 * | 2/2015 | Huck | A61P 9/10 514/266.1 |
| 9,145,392 B2 | 9/2015 | An et al. | |
| 9,321,760 B2 | 4/2016 | Lan et al. | |
| 9,434,714 B2 | 9/2016 | Lan et al. | |
| 9,458,134 B2 | 10/2016 | Lan et al. | |
| 9,662,330 B2 | 5/2017 | Lan et al. | |
| 10,080,750 B2 | 9/2018 | Lan et al. | |
| 2014/0343029 A1 | 11/2014 | Lan et al. | |
| 2015/0126484 A1 | 5/2015 | Lan et al. | |
| 2015/0225371 A1 | 8/2015 | Lan et al. | |
| 2016/0000785 A1 | 1/2016 | Lan et al. | |
| 2016/0016936 A1 | 1/2016 | Lan et al. | |
| 2016/0184308 A1 | 6/2016 | Lan et al. | |
| 2017/0119766 A1 | 5/2017 | Huck et al. | |
| 2017/0136018 A1 | 5/2017 | Delovade et al. | |
| 2017/0217905 A1 | 8/2017 | Lan et al. | |
| 2018/0244654 A1 | 8/2018 | Schiltz et al. | |
| 2022/0289686 A1 | 9/2022 | Major et al. | |

FOREIGN PATENT DOCUMENTS

| | | |
|---|---|---|
| CN | 106045918 B | 2/2019 |
| WO | 2013040044 A1 | 3/2013 |
| WO | 2013040059 A1 | 3/2013 |
| WO | 2013174780 A1 | 11/2013 |
| WO | 2014093230 A2 | 6/2014 |
| WO | 2014143612 A1 | 9/2014 |
| WO | 2015123174 A1 | 8/2015 |
| WO | 2020101382 A1 | 5/2020 |

OTHER PUBLICATIONS

Muchmore Steven W. Crystal Structures of Human Adenosine Kinase Inhibitor Complexes Reveal Two Distinct Binding Modes. J. Med. Chem. 2006, 49, 6726-6731.
Pearce Laura R. et al. Characterization of PF-4708671, a novel and highly specific inhibitor of p70 ribosomal S6 kinase (S6K1). Biochem. J. (2010) 431, 245-255.
Bussenius Joerg et al. Design and evaluation of a series of pyrazolopyrimidines as p70S6K inhibitors. Bioorganic & Medicinal Chemistry Letters 22 (2012) 2283-2286.
Bavetsias Vassilios et al. 7-(Pyrazol-4-yl)-3H-imidazo[4,5-b]pyridine-based derivatives for kinase inhibition: Co-crystallisation studies with Aurora—A reveal distinct differences in the orientation of the pyrazole N1-substituent. Bioorganic & Medicinal Chemistry Letters 25 (2015) 4203-4209.
Xiao Yufang et al. Discovery of 4-aminopyrimidine analogs as highly potent dual P70S6K/Akt inhibitors. Bioorg. Med. Chem. Lett. 50 (2021) 128352.
Bolli Martin H. et al. The The Discovery of N-[5-(4-Bromophenyl)-6-[2-[(5-bromo-2-pyrimidinyl)oxy]ethoxy]-4-pyrimidinyl]-N'-propylsulfamide(Macitentan), an Orally Active, Potent Dual Endothelin Receptor Antagonist. J. Med. Chem 55 (2012) 7849.

* cited by examiner

*Primary Examiner* — Kamal A Saeed
(74) *Attorney, Agent, or Firm* — Angelo Castellino

(57) ABSTRACT

Pyrimidine and Pyridine containing compounds are described herein that are enzyme p70S6K inhibitors useful in the treatment of S6K-dependent or S6K-mediated diseases and conditions, including but not limited to cancer, fibrotic metabolic and certain neurological disorders.

21 Claims, No Drawings

PYRIMIDINE AND PYRIDINE AMINE COMPOUNDS AND USAGE THEREOF IN DISEASE TREATMENT

STATEMENT OF GOVERNMENT INTEREST

This invention was made with government support under Grants CA183195 and MH115529 awarded by the National Institutes of Health. The government has certain rights in the invention.

FIELD OF THE INVENTION

The invention relates to a series of heterocyclic pyrimidine and pyridine amine compounds that are useful in the treatment of diseases, such as cancer, fibrotic, metabolic and certain neurological disorders in mammals. Also encompassed by the present invention is the use of such compounds in the treatment of diseases in mammals, especially humans, and pharmaceutical compositions containing such compounds.

BACKGROUND OF THE INVENTION

Protein kinases constitute a large family of structurally related enzymes that are responsible for the control of a wide variety of signal transduction processes within the cell [Hardie (1995)]. Kinases regulate many different cell processes including, but not limited to, proliferation, differentiation, apoptosis, motility, transcription, translation and other signaling processes. Dysfunctional signaling due to defective control of protein phosphorylation has been implicated in a number of diseases, including, for example, inflammation, cancer, allergy/asthma, diseases and conditions of the immune system, diseases and conditions of the central nervous system, and angiogenesis. The enzyme p70S6K modulates protein synthesis by phosphorylation of the S6 ribosomal protein. p70S6K (S6K) activation has been implicated in cell cycle control, neuronal cell differentiation, regulation of cell motility and a cellular response that is important in tumor metastases, the immune response and tissue repair.

A role for S6K in tumor cell proliferation and protection of cells from apoptosis is supported based on its participation in growth factor receptor signal transduction, overexpression and activation in tumor tissues. [Magnuson (2012)]. S6K activation is further implicated in directed metastasis of breast and ovarian cancer cells [Khotskaya (2014), Akar (2010), Ip (2011)]. Accordingly, inhibitors of S6K are of utility in the treatment of cancers.

Tissue scarring caused by fibrosis is a proliferative condition that leads to health complications. Idiopathic pulmonary fibrosis (IPF) is a disease in which lung tissue is scarred that leads to shortness of breath for which very few treatments are available. S6K has been implicated in aspects of pulmonary fibrosis [Madala (2016)] indicating that S6K inhibitors are of utility in IPF.

The absence of S6K protects against age- and diet-induced obesity while enhancing insulin sensitivity. S6K inhibition is of utility in metabolic diseases and disorders such as obesity, diabetes, metabolic syndrome, insulin resistance, hyperglycemia, hyperaminoacidemia, and hyperlipidmia is supported based upon these findings. In relation to these findings S6K inhibition has been identified as a therapeutic strategy to treat dysfunction of this pathway in the liver and so treat conditions including liver fibrosis, liver cancer and non-alcoholic steatohepatitis (NASH) [Hwahng (2009), Gäbele (2005), Bae (2012)].

Aberrant neuronal translation linked to S6K is apparent in a number of neuropsychiatric conditions known as autism spectrum disorders [Ehninger (2011)] including Fragile X syndrome [Bhattacharya (2012), Bhattacharya (2015)]. S6K activation has been reported as an important factor in these conditions suggesting that S6K inhibitors will be of utility for the treatment of such diseases.

Agents that modulate S6K to alter signal transduction through its signaling pathway (i.e., by competitive or non-competitive inhibition or acting as inverse agonists or activators or allosteric potentiators or inhibitors) reduce manifestations of the diseases described herein. Compounds described as suitable for S6K inhibition are disclosed in WO 03/064397, WO 04/092154, WO 05/054237, WO 05/056014, WO 05/033086, WO 05/117909, WO 05/039506, WO 06/120573, WO 06/136821, WO 06/071819, WO 06/131835, WO 08/140947, WO 10/093419, WO 10/056563, WO 12/013282, WO 12/016001 and WO 12/069146.

SUMMARY OF THE INVENTION

Disclosed herein are heterocyclic compounds, methods of their preparation and their uses in treating diseases, such as cancer, fibrotic, metabolic and certain neurological disorders.

The heterocyclic compounds of the invention include compounds of Formula I that have the structure:

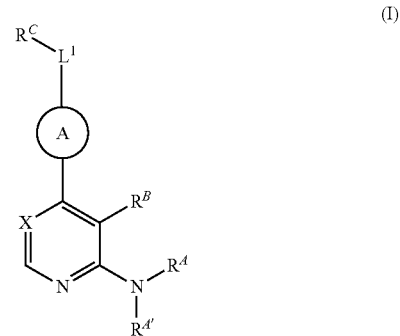

or a salt, including a pharmaceutically acceptable salt prodrug thereof, wherein X is =N— or a carbon that is substituted or unsubstituted;

$R^A$ is —H, —CN, $C_1$-$C_4$ alkyl, $C_1$-$C_4$ fluoroalkyl, —C(O)$R^D$, —$SO_2R^D$;

$R^{A'}$ is —H, $C_1$-$C_4$ alkyl, $C_1$-$C_4$ fluoroalkyl, or —C(O)$R^D$;

$R^B$ is substituted phenyl or $C_5$-$C_6$ heteroaryl (Ar, or HetAr), either of which is unsubstituted or substituted by up to three $R^E$ independently of one another;

$L^1$ is a bond, or a $C_1$-$C_4$ unbranched alkylene, a $C_3$-$C_6$ cycloalkylene or a 3-6-membered heterocycloalkylene, either one of which is unsubstituted or substituted by one or two $R^F$ independently of one another and/or having one, two or three of its —$CH_2$— groups independently replaced by —O—, —NH—, or —CO— or, $L^1$ is a $C_3$-$C_7$ branched alkylene, which is unsubstituted or substituted by one or two $R^F$ independently of one another, and/or having one, two or three of its —$CH_2$— groups independently replaced by —O—, —NH—, or —CO— and/or having one of its —CH— groups replaced by —N—;

$R^C$ is a $C_6$ or $C_{10}$ aryl or $C_5$-$C_{10}$ heteroaryl, either of which is unsubstituted or substituted by up to three $R^G$ independently of one another, Ring A is a pyrazole moiety having the structure of:

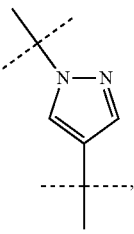

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;

$R^D$ is —H or an unsubstituted or substituted $C_1$-$C_4$ alkyl or an amino acid moiety;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$ alkyl, —S(O)$C_1$-$C_4$ alkyl, —SO$_2C_1$-$C_4$ alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$ alkyl, —SO$_2C_1$-$C_4$ alkyl, —N($C_1$-$C_4$ alkyl)$_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —NH$_2$, —NMe$_2$, —CONH$_2$, —CONHMe, —CONMe$_2$, —COOH, —CH$_3$ and —CF$_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2C_1$-$C_4$alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —SO$_2C_1$-$C_4$alkyl, —N($C_1$-$C_4$ alkyl)$_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

wherein the remaining aromatic carbon atom(s) of the pyrimidine or pyridine ring of formula I is unsubstituted or independently substituted by $R^J$; and wherein each $R^J$, if present is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2C_1$-$C_4$alkyl, —NH$_2$, —NH$C_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —NH$_2$, and —OH.

Other compounds of the invention have structures recited in the numbered embodiments and claims.

Further disclosed is a medicament for treating a subject with a S6K-dependent disease or condition, the medicament comprising a compound of formula 1, together with methods for treating said S6K-dependent or S6K-mediated disease or condition.

DETAILED DESCRIPTION OF THE INVENTION

Definitions

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or where permitted by context. Thus, as used in the specification and the appended claims, the singular forms "a," "an" and "the" include plural referents unless the context clearly dictates otherwise.

At various locations in the present disclosure, e.g., in any disclosed embodiments or in the claims, reference is made to compounds, compositions or methods that "comprise" one or more specified components, elements or steps. Invention embodiments also specifically include those compounds, compositions or methods that are or that consist of or that consist essentially of those specified components, elements or steps. The terms "comprising", "consist of" and "consist essentially of" have their normally accepted meanings under U.S. patent law unless otherwise specifically stated. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s) that do not adversely effect or negate the use of the compositions or methods as disclosed herein. Similarly, disclosed compositions, devices, articles of manufacture or methods that "consist of" a component or step are closed and they would not include or read on those compositions or methods having appreciable amounts of an additional component(s) or an additional step(s). Furthermore, use of the term "including" as well as other forms, such as "include", "includes," and "included," is not limiting. The section headings used herein are for organizational purposes only and are not to be construed as limiting the subject matter described. Unless otherwise indicated, conventional methods of mass spectroscopy, NMR, HPLC, protein chemistry, cell biology, biochemistry, pharmacology, recombinant DNA techniques and cell culture are employed.

"Bond" or "single bond" as used herein means a chemical bond between two atoms, or two moieties when the atoms joined by the bond are considered to be part of larger substructure. As explicitly stated or implied by context, when a group described herein is a bond, the referenced group is absent thereby allowing a bond to be formed between the remaining identified groups.

"Membered ring" as used herein means any cyclic structure. The term "membered" is meant to denote the number of skeletal atoms that constitute the ring. Thus, by way of example and not limitation, those membered rings include cyclohexyl, pyridinyl, pyranyl and thiopyranyl, which are 6-membered rings and cyclopentyl, pyrrolyl, furanyl, and thienyl, which are 5-membered rings.

"Moiety" as used herein means a specific segment, fragment or functional group of a molecule or compound. Chemical moieties are sometimes indicated as chemical entities that are embedded in or appended to (i.e., a substituent or variable group) a molecule or compound.

"Alkyl" as used herein is methyl or a collection of carbon atoms that are covalently linked together (i.e., contiguous) in normal, secondary, tertiary or cyclic arrangements, i.e., in a linear, branched, or cyclic arrangement (i.e., cycloalkyl) or some combination thereof having a radical $sp^3$ carbon center. An alkyl substituent to a larger structure or moiety is methyl or that group of contiguous carbon atoms covalently attached to the structure or moiety with which it is associated through the radical $sp^3$ carbon of the alkyl substituent. Therefore, an alkyl substituent, as used herein, contains at least one saturated moiety or group and may additionally contain unsaturated alkyl moieties or groups wherein one or more of the hydrogen atoms within a group of contiguous saturated alkyl moieties or groups or on methyl are replaced by independently selected unsaturated alkyl moieties or groups, i.e., an alkyl substituent may comprise a single or contiguous groups of carbons and one, two, three or more independently selected unsaturated alkyl moieties or groups, if such moieties or groups within the alkyl substituent are present, and may contain or further contain one, two, three or more independently selected double bonds or triple bonds or a combination therefore, typically one double or one triple bond if such unsaturation within the alkyl substituent is present.

A saturated alkyl or cycloalkyl substituent contains $sp^3$ carbon atoms and no aromatic, $sp^2$ or sp carbon atoms. An unsaturated alkyl substituent, moiety or group is as described below for alkenyl, cycloalkenyl and alkynyl moieties and additionally contains at least one $sp^3$ carbon atom. Typically, a saturated alkyl or cycloalkyl is related to parent alkane or cycloalkane in which a hydrogen atom from one of its $sp^3$ carbons of the alkane or cycloalkane has been removed to provide a radical center.

The number of carbon atoms in a saturated or unsaturated alkyl substituent, moiety or group can vary and typically is 1 to about 50, e.g., 1-30, 1-20, or 1-10, more typically 1-8 or 1-6, unless otherwise specified, e.g., $C_{1-8}$ alkyl or C1-C8 alkyl means an alkyl substituent, moiety or group containing 1, 2, 3, 4, 5, 6, 7 or 8 carbon atoms, wherein one or more of the carbon atoms are $sp^3$ carbons, and $C_{1-6}$ alkyl or C1-C6 means an alkyl substituent, moiety or group containing 1, 2, 3, 4, 5 or 6 carbon atoms, wherein one or more of the carbon atoms are $sp^3$ carbon atoms. When an alkyl substituent, moiety or group is specified, species may include saturated alkyl moieties such as methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear, cyclic and branched chain saturated alkyl moieties.

Unless otherwise specified, alkyl groups can be substituted with cyclic saturated species and/or unsaturated species and groups described below for cycloalkyl, alkenyl, alkynyl, (hetero)aryl, alkyl(hetero)aryl groups and the like.

"Cycloalkyl" as used herein is a monocyclic, bicyclic, tricyclic or polycyclic ring system having a radical center and is composed of only carbon atoms wherein at least one carbon atoms is saturated. The term "cycloalkyl" encompasses a monocyclic, bicyclic, tricyclic or polycyclic aliphatic moiety wherein each of the atoms forming the ring(s) (i.e., skeletal atoms) is a carbon atom. A cycloalkyl substituent to a larger structure or moiety is that group of cyclic carbon atoms that is covalently attached to the structure or moiety with which it is associated through the radical carbon of the cyclic ring system. Typically, cycloalkyl is related to a parent cycloalkane or cycloalkene in which a hydrogen atom from one of its ring carbons has been removed to provide a radical center.

The number of carbon atoms in a cycloalkyl substituent, moiety or group can vary and typically is 3 to about 50, e.g., 3-30, 3-20, or 3-10, more typically 3-8 or 3-6, unless otherwise specified, e.g., $C_{3-8}$ cycloalkyl or C3-C8 cycloalkyl means an cycloalkyl substituent, moiety or group containing 3, 4, 5, 6, 7 or 8 carbon atoms in a cyclic arrangement and $C_{3-6}$ cycloalkyl or C3-C6 cycloalkyl means an cycloalkyl substituent, moiety or group containing 3, 4, 5 or 6 carbon atoms in a cyclic arrangement. Cycloalkyl substituents, moieties or groups will typically have 3, 4, 5, 6, 7, 8, 9, 10, 11, 12, 13, 14, 15, 16, 17, 18, 19 or 20 carbon atoms in a cyclic arrangement that may contain exo or endo-cyclic double bonds or endo-cyclic triple bonds or a combination of both wherein the endo-cyclic double or triple bonds, or the combination of both, do not form a cyclic conjugated system of 4n+2 electrons (i.e., is not aromatic). A bicyclic ring system may share one (i.e., spiro ring system) or two carbon atoms and a tricyclic ring system may share a total of 2, 3 or 4 carbon atoms, typically 2 or 3. Unless otherwise specified, cycloalkyl substituents, moieties or groups can be substituted with saturated and/or unsaturated moieties and groups described for alkyl, alkenyl, alkynyl, aryl, arylalkyl, alkylaryl and the like and can contain one or more other cycloalkyl moieties. Thus, cycloalkyls may be saturated, or partially unsaturated. Cycloalkyls may be fused with an aromatic ring, wherein attachment to the aromatic ring is through two carbons of the cycloalkyl substituent, moiety or group to two adjacent carbons of the aromatic ring (i.e., two aromatic carbons comprise the cycloalkyl ring). Cycloalkyl substituents, moieties or groups having 3-10 carbons include cyclopropyl, cyclopentyl, cyclohexyl, adamantly and further include cyclobutyl, cyclopentenyl, cyclohexenyl, cycloheptyl and cyclooctyl. Cycloalkyl groups may be substituted or unsubstituted. Depending on the substituent structure, a cycloalkyl substituent can be a monoradical or a diradical (i.e., a cycloalkylene, also referred to as carbocyclo), such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like).

"Alkylamine" as used herein means a —N(C$_1$-C$_{20}$ alkyl)$_x$H$_y$ group, moiety or substituent having a radical nitrogen center, wherein x and y are x=1; y=1 or x=2; y=0. Alkylamine includes those —N(alkyl)$_x$H$_y$ groups wherein x=2 and y=0 and the alkyl groups taken together with the nitrogen atom to which they are attached form a cyclic ring system (i.e., the cyclic ring system is a nitrogen-containing heterocycle). Typically, alkylamine is related to parent alkyl or cycloalkyl in which its carbon radical center has been replaced with a nitrogen radical center.

"Heteroalkyl" as used herein means an alkyl group, moiety or substituent in which a skeletal carbon atom other than the radical center of an alkyl moiety is replaced with a heteroatom or groups of atoms, wherein at least one of the atoms in the group is a heteroatom (e.g., Ls as defined herein) that replaces the skeletal carbon atom. Those atoms or groups of atoms include by way of example and not limitation, oxygen, nitrogen, sulfur, phosphorus or combinations thereof. Heteroalkyl include aminoalkyl moieties such as $R^1R^2N$—$(C_1$-$C_{20}$ alkyl)-, which are exemplary $C_1$-$C_{20}$ heteroalkyls, wherein $R^1$ and $R^2$ are independently selected hydrogen or $C_1$-$C_{20}$ alkyl, typically $C_1$-$C_8$ alkyl, $C_1$-$C_6$ alkyl or $C_1$-$C_4$ alkyl, or taken together with the nitrogen heteroatom to which they are attached define a heterocycloalkyl and typically are $R^1R^2N$—$(C_1$-$C_8$ alkyl)-, $R^1R^2N$—$(C_1$-$C_6$ alkyl)- or $R^1R^2N$—$(C_1$-$C_4$ alkyl)-.

"Heteroalkylene" as used herein means an alkylene (i.e., alkanediyl) group, moiety or substituent in which one or more skeletal carbon atoms of an alkylene moiety are replaced with a atom (or atoms) other than carbon or hydrogen, or are replaced by groups of atoms, wherein at least one of the atoms in the group is other than carbon or hydrogen (e.g., a Ls as defined herein). Those atoms or groups of atoms include by way of example and not limitation, oxygen, nitrogen, sulfur, phosphorus or combinations thereof. Heteroalkylene includes $C_1$-$C_{20}$ heteroalkylene and typically are $C_1$-$C_8$ heteroalkylene, $C_1$-$C_6$ heteroalkylene or $C_1$-$C_4$ heteroalkylene. Exemplary heteroalkylenes include, but are not limited to, —$OCH_2$—, —$OCH(CH_3)$—, —$OC(CH_3)_2$—, —$OCH_2CH_2$—, —$CH_2O$—, —$CH(CH_3)O$—, —$C(CH_3)_2O$—, —$CH_2CH_2O$—, —$CH_2OCH_2$—, —$CH_2OCH_2CH_2$—, —$CH_2CH_2OCH_2$—, —$SCH_2$—, —$SCH(CH_3)$—, —$SC(CH_3)_2$—, —$SCH_2CH_2$—, —$CH_2S$—, —$CH(CH_3)S$—, —$C(CH_3)_2S$—, —$CH_2CH_2S$—, —$CH_2SCH_2$—, —$CH_2SCH_2CH_2$—, —$CH_2CH_2SCH_2$—, —$SO_2CH_2$—, —$SO_2CH(CH_3)$—, —$SO_2C(CH_3)_2$—, —$SO_2CH_2CH_2$—, —$CH_2SO_2$—, —$CH(CH_3)SO_2$—, —$C(CH_3)_2SO_2$—, —$CH_2CH_2SO_2$—, —$CH_2SO_2CH_2$—, —$CH_2SO_2CH_2CH_2$—, —$CH_2CH_2SO_2CH_2$—, —$NHCH_2$—, —$NHCH(CH_3)$—, —$NHC(CH_3)_2$—, —$NHCH_2CH_2$—, —$CH_2NH$—, $CH(CH_3)NH$—, —$C(CH_3)_2NH$—, —$CH_2CH_2NH$—, —$CH_2NHCH_2$—, —$CH_2NHCH_2CH_2$—, —$CH_2CH_2NHCH_2$—, and the like.

"Carboxylic acid bioisostere" as used herein means a functional group, moiety or substituent that exhibits similar physical, biological and/or chemical properties as a carboxylic acid moiety. By way of example and not limitation, carboxylic acid bioisosteres include,

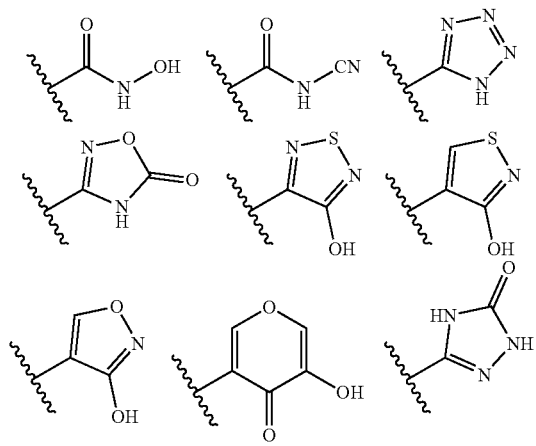

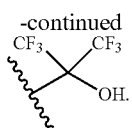

"Prodrug" as used herein refers to a moiety, substituent or group capable of biological cleavage to provide a biologically active substance. A large number of such groups are described in "Design of Prodrugs", Hans Bundgaard (Elsevier, N.Y., 1985, ISBN 0-444-80675-X) (Bundgaard) and will not be detailed here. In particular, Bundgaard, at pages 1-92, describes prodrugs and their biological cleavage reactions for a number of functional group types, the disclosures of which are incorporated by reference herein. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs at pages 62 to 70, the disclosures of which are also incorporated by reference herein. Prodrugs are additionally exemplified in certain instances by protecting groups as described herein.

"Alkenyl" as used herein means a substituent, moiety or group having a radical center and is comprised of one or more double bond functional groups (e.g., as in —CH═CH— or ═CH—), e.g., 1, 2, 3, 4, 5, 6 or more, typically 1, 2 or 3 double bond functional groups, and additionally comprises linked normal, secondary, tertiary or cyclic $sp^3$ carbon atoms, i.e., linear, branched, cyclic or any combination thereof unless the alkenyl moiety is vinyl (—CH═$CH_2$). An alkenyl moiety, group or substituent with multiple double bonds may have the double bond functional groups arranged contiguously (i.e., a 1,3-butadienyl moiety) or non-contiguously with one or more intervening saturated carbon atoms or a combination thereof, provided that a cyclic, contiguous arrangement of double bonds do not form a cyclically conjugated system of 4n+2 electrons (i.e., is not aromatic).

The number of carbon atoms in an alkenyl substituent, group or moiety can vary and typically is 1 to 50, e.g., 2-30, 2-20 or 2-10, more typically 2-8, 2-6 or 2-4, unless otherwise specified, e.g., $C_2$ 8 alkenyl or $C_2$-8 alkenyl means an alkenyl substituent, moiety or group containing 2, 3, 4, 5, 6, 7 or 8 carbon atoms in which at least one is an $sp^2$ carbon and $C_{2-6}$ alkenyl or $C_2$-6 alkenyl means an alkenyl substituent, moiety or group containing 2, 3, 4, 5 or 6 carbon atoms in which at least one is an $sp^2$ carbon. Alkenyl substituents, moieties or groups will typically have 2, 3, 4, 5, 6, 7, 8, 9, 10, 11, 12, 13, 14, 15, 16, 17, 18, 18 or 20 carbon atoms having one $sp^2$ carbon atom or two adjacent $sp^2$ carbon atoms.

When an alkenyl moiety, group or substituent is specified, species include, by way of example and not limitation, any of the alkyl or cycloalkyl, groups, moieties or substituents described herein that has one or more double bonds and further includes methylene (═$CH_2$), which is a $C_1$-alkylene, methylmethylene (═CH—$CH_3$), ethylmethylene (═CH—$CH_2$—$CH_3$), ═CH—$CH_2$—$CH_2$—$CH_3$, vinyl (—CH═$CH_2$), allyl, 1-methylvinyl, butenyl, iso-butenyl, 3-methyl-2-butenyl, 1-pentenyl, cyclopentenyl, 1-methylcyclopentenyl, 1-hexenyl, 3-hexenyl, cyclohexenyl and other linear, cyclic and branched chained all carbon containing moieties containing at least one double bond functional group.

When alkenyl is used as a substituent to a larger structure or moiety the alkenyl is single bonded or double bonded to the structure or moiety with which it is associated through a sp² carbon of an alkenyl functional group unless specified otherwise. In some aspects, an alkenyl substituent is related to parent alkene by removal of a hydrogen atom from one of its sp² carbons. In other aspects an alkenyl is related to a parent alkane by replacing one of its sp³ carbon atoms with a sp² carbon or by replacing two adjacent sp³ carbon atoms with two adjacent sp² carbon atoms in which one provides a radical center.

"Alkynyl" as used herein means a substituent, moiety or group that comprises one or more triple bonds (—C≡C—), e.g., 1, 2, 3, 4, 5, 6 or more, typically 1 or 2 triple bonds, optionally comprising 1, 2, 3, 4, 5, 6 or more double bonds, with the remaining bonds (if present) being single bonds and comprising linked normal, secondary, tertiary or cyclic carbon atoms, i.e., linear, branched, cyclic or any combination thereof, unless the alkynyl moiety is ethynyl. The number of carbon atoms in an alkynyl moiety or group can vary and typically is 2 to 50, e.g., 2-30, 2-20 or 2-10, more typically 2-8, 2-6 or 2-4, unless otherwise specified, e.g., $C_{28}$ alkynyl or C2-8 alkynyl means an alkynyl substituent, moiety or group containing 2, 3, 4, 5, 6, 7 or 8 carbon atoms in which at least two adjacent carbon atoms are sp carbon atoms. An alkynyl substituent, moiety or group will typically have 2, 3, 4, 5, 6, 7, 8, 9, 10, 11, 12, 13, 14, 15, 16, 17, 18, 19 or 20 carbon atoms in which two adjacent carbon atoms are sp carbon atoms. When an alkynyl substituent, moiety or group is specified, species include, by way of example and not limitation, any of the alkyl moieties, groups or substituents described herein that contains one or more triple bonds and further includes, ethynyl, propynyl, butynyl, iso-butynyl, 3-methyl-2-butynyl, 1-pentynyl, cyclopentynyl, 1-methyl-cyclopentynyl, 1-hexynyl, 3-hexynyl, cyclohexynyl and other linear, cyclic and branched chained all carbon containing moieties containing at least one triple bond. When an alkynyl is used as substituent to a larger structure or moiety the alkynyl is single bonded to the structure or moiety with which it is associated through one of the unsaturated carbons (i.e., a sp carbon) of the alkynyl functional group. In some aspects, an alkynyl substituent is related to parent terminal alkyne in which a hydrogen atom from its terminal sp carbon has been removed to provide a radical center.

"Aromatic" as used herein refers to a planar ring having a delocalized pi-electron system containing 4n+2 pi electrons, where n is an integer. Aromatic rings can be formed from five, six, seven, eight, nine, ten, or more than ten atoms. Aromatics are optionally substituted. The term "aromatic" includes both carbocylic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of aromatic carbon atoms) groups.

"Aryl" as used here means an aromatic ring system or a fused ring system with no ring heteroatoms comprising 1, 2, 3 or 4 to 6 rings, typically 1 to 3 rings, in which one of the aromatic carbons provides a radical center; wherein the rings are composed of only carbon atoms; and refers to a cyclically conjugated system of 4n+2 electrons (Hückel rule), typically 6, 10 or 14 electrons some of which may additionally participate in exocyclic conjugation [cross-conjugated (e.g., quinone)]. Aryl substituents, moieties or groups are typically formed by six, 10, or more than 10 carbon atoms, e.g., $C_6$-$C_{24}$ aryl, $C_6$-$C_{14}$ aryl and $C_6$-$C_{10}$ aryl. Aryl substituents, moieties or groups are optionally substituted. Optionally substituted aryl include aryl substituted with one or more halogens, typically —F or Cl, an O-linked substituent, typically —OH or —OCH₃, or some combination thereof. Exemplary aryls include $C_6$, $C_{10}$ and $C_{14}$ aryls such as phenyl, naphthalenyl and phenanthryl. Depending on the structure, an aryl moiety or group can be a monoradical or a diradical (i.e., an arylene group, also referred to as an arenediyl). Exemplary arylenes include, but are not limited to, phenyl-1,2-ene, phenyl-1,3-ene, and phenyl-1,4-ene. When aryl is used as a substituent to a larger structure or moiety, the aryl is single bonded to the structure or moiety with which it is associated through the radical aromatic carbon center of the aryl group. Typically, an aryl is related to a parent arene in which a hydrogen atom has been removed from one of the aromatic carbons of its aromatic ring system, and arylene is typically related to an aryl moiety through removal of another hydrogen atom from a different aromatic carbon.

"Arylalkylene" as used herein means a substituent, moiety or group where an aryl moiety is bonded to an alkylene moiety, i.e., -alkylene-aryl, where alkylene and aryl groups are as described above. Arylenealkyl includes —$C_1$-$C_{20}$ alkylene-($C_6$-$C_{24}$ aryl), —$C_1$-$C_8$ alkylene-($C_6$-$C_{14}$ aryl), —$C_1$-$C_6$ alkylene-($C_6$-$C_{10}$ aryl) or —$C_1$-$C_4$ alkylene-($C_6$-$C_{10}$ aryl), e.g., —$CH_2$—$C_6H_5$ or —$CH_2CH(CH_3)$—$C_6H_5$. When arylalkylene is used as a substituent to a larger structure or moiety, the alkylene moiety of the arylalkyl is single bonded to the structure or moiety with which it is associated through the radical sp³ carbon of the alkylene moiety. Heteroarylalkylene, arylheteroalkylene, and heteroarylheteroalkylene are likewise given by the definitions of heteroaryl and heteroalkylene as defined elsewhere and are included within the definition of arylalkylene unless otherwise indicated or implied by context.

"Alkylarylene" as used herein means a substituent, moiety or group where an alkyl moiety is bonded to an arylene moiety, i.e., -arylene-alkyl, where arylene and alkyl groups are as described above. Alkylarylene includes —$C_6$-$C_{24}$ arylene-($C_1$-$C_{20}$ alkyl), —$C_6$-$C_{14}$ arylene-($C_1$-$C_8$ alkyl), —$C_6$-$C_{10}$ arylene-($C_1$-$C_6$ alkyl) or —$C_6$-$C_{10}$ arylene-($C_1$-$C_4$ alkyl), e.g., —$C_6H_4$—$CH_3$ or —$C_6H_4$—$CH_2CH(CH_3)_2$. When alkylarylene is used as a substituent to a larger structure or moiety, the arylene moiety of the alkylaryl is attached to the structure or moiety with which it is associated through an aromatic radical carbon of the arylene moiety. Heteroalkylarylene alkylheteroarylene and heteroalkylheteroarylene are given by the definitions of heteroarylene and heteroalkyl as defined elsewhere and are included within the definition of alkylarylene unless otherwise indicated or implied by context.

"Substituted alkyl", "substituted cycloalkyl", "substituted alkenyl", "substituted alkynyl", substituted alkylarylene", "substituted arylalkylene", "substituted heterocycle", "substituted aryl", substituted heteroaryl or the like as used herein typically means an $C_1$-$C_{20}$ alkyl, $C_1$ or $C_2$-$C_{20}$ alkenyl, $C_2$-$C_{20}$ alkynyl, ($C_1$-$C_{20}$ alkyl)-$C_6$-$C_{24}$ arylene-, ($C_6$-$C_{24}$ aryl)-$C_1$-$C_{20}$ alkylene-, $C_3$-$C_{24}$ heterocycle, $C_6$-$C_{24}$ aryl, $C_5$-$C_{24}$ heteroaryl, or other substituent, group or moiety as defined or disclosed herein that has a moiety or group that replaces a hydrogen atom(s), or has a heteroatom or a group of non-carbon atom (e.g., an Ls as defined herein) that interrupts a carbon atom chain of an alkyl or alkyl-containing group or moiety as defined or disclosed herein. Alkenyl and alkynyl moieties that are substituents to a larger structure or moiety are optionally substituted by replacement of a carbon atom that is one or more carbon atoms removed from the double or triple bond functional group, or by replacement of a hydrogen atom where present of a sp² carbon or sp carbon atom of its alkene or alkyne functional group or by replacement of a hydrogen atom elsewhere in the carbon chain of the alkenyl or alkynyl moiety.

"Optionally substituted alkyl", "optionally substituted alkenyl", "optionally substituted alkynyl", "optionally substituted alkylarylene", "optionally substituted arylalkylene", "optionally substituted heterocycle", "optionally substituted aryl", "optionally substituted heteroaryl", "optionally substituted alkylheteroarylene", "optionally substituted heteroarylalkylene" and the like as used herein typically means a $C_1$-$C_{20}$ alkyl, $C_1$ or $C_2$-$C_{20}$ alkenyl, $C_2$-$C_{20}$ alkynyl, ($C_1$-$C_{20}$ alkyl)-$C_6$-$C_{24}$ arylene-, ($C_6$-$C_{24}$ aryl)-$C_1$-$C_{20}$ alkylene-, $C_3$-$C_{24}$ heterocycle, $C_6$-$C_{24}$ aryl, $C_5$-$C_{24}$ heteroaryl, ($C_1$-$C_{20}$ alkyl)-$C_5$-$C_{24}$ heteroarylene, ($C_5$-$C_{24}$ heteroaryl)-$C_1$-$C_{20}$ alkylene-, or other substituent, moiety or group as defined or disclosed herein that has a moiety(ies) or group(s) that optionally replaces a hydrogen atom(s), or for an alkyl or alkyl-containing moiety or group has an optional non-carbon atom or a group of non-carbon atoms (e.g., a Ls as defined herein) that interrupts a carbon atom chain the alkyl or alkyl-containing moiety or group (i.e., the optional non-carbon atom or group of non-carbon atoms replaces one or some of the sp$^3$ carbons of an alkyl or alkyl-containing moiety or group) as defined or disclosed herein. For a phenyl or phenylene moiety, the arrangement of any two substituents present on the aromatic ring can be ortho (o), meta (m), or para (p) to each other. An optionally substituted fluoroalkyl is an alkyl or cycloalkyl moiety, typically a linear alkyl, wherein one or more hydrogen atoms are replaced by fluorine and may contain other atoms other than carbon and fluorine.

A substituted or an optionally substituted group, moiety or substituent includes those having one or more additional group(s) that replace its hydrogen atom(s) that are independently selected from the group consisting of alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. By way of example and not limitation an optional substituent(s) may be a protecting group, halide, —CN, —NO$_2$, or LsRs, wherein each Ls is independently selected from a bond, —O—, —C(═O)—, —C(═O)O—, —S—, —S(═O)—, —S(═O)$_2$—, —NH—, —NHC(═O)—, —C(═O)NH—, —S(═O)$_2$NH—, —NHS(═O)$_2$—, —OC(═O)NH—, —NHC(═O)O—, or —(C$_1$-C$_{20}$ alkylene)-; and each Rs is selected from —H, C$_1$-C$_{20}$ alkyl, C$_1$-C$_{20}$ fluoroalkyl, C$_1$-C$_{20}$ heteroalkyl, C$_3$-C$_{20}$ cycloalkyl, C$_6$-C$_{24}$ aryl, C$_5$-C$_{24}$ heteroaryl, or C$_3$-C$_{20}$ heterocycloalkyl.

The protecting groups that form the protective derivatives of the above substituents may be found in sources such as Greene and Wuts, above. Other optional substituents include those selected from the group consisting of halogen, —CN, —NH$_2$, —OH, —N(CH$_3$)$_2$, C$_1$-C$_{20}$ alkyl, C$_1$-C$_{20}$ fluoroalkyl, C$_1$-C$_{20}$ heteroalkyl, C$_3$-C$_{20}$ cycloalkyl, C$_3$-C$_{20}$ heterocycloalkyl, C$_6$-C$_{24}$ aryl, C$_5$-C$_{24}$ heteroaryl, C$_1$-C$_{20}$ alkoxy, C$_6$-C$_{24}$ aryloxy, C$_1$-C$_{20}$ alkylthio, C$_6$-C$_{24}$ arylthio, C$_1$-C$_{20}$ alkylsulfoxide, C$_6$-C$_{24}$ arylsulfoxide, C$_1$-C$_{20}$ alkylsulfone, and C$_6$-C$_{24}$ arylsulfone, those selected from the group consisting of halogen, —CN, —NH$_2$, —OH, —NH(CH$_3$), —N(CH$_3$)$_2$, —CO$_2$H, —CO$_2$(C$_1$-C$_8$ alkyl), —C(═O)NH$_2$, —C(═O)NH(C$_1$-C$_8$ alkyl), —C(═O)N(C$_1$-C$_8$ alkyl)$_2$, —S(═O)$_2$NH$_2$, —S(═O)$_2$NH(C$_1$-C$_8$ alkyl), —S(═O)$_2$N(C$_1$-C$_8$ alkyl)$_2$, C$_1$-C$_8$ alkyl, C$_3$-C$_{10}$ cycloalkyl, C$_1$-C$_8$ fluoroalkyl, C$_3$-C$_{10}$ heteroalkyl, C$_1$-C$_8$ alkoxy, C$_1$-C$_8$ fluoroalkoxy, —S—(C$_1$-C$_8$ alkyl) and —S(═O)$_2$(C$_1$-C$_8$ alkyl), wherein C$_1$-C$_{20}$ alkyl or C$_1$-C$_8$ alkyl are independently selected, or those selected from the group consisting of halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$.

Typically, an optionally substituted, substituent, moiety or group is substituted with one or two of the preceding groups, or more typically with one of the preceding groups. An optional substituent on an aliphatic carbon atom (acyclic or cyclic or saturated or unsaturated carbon atoms, excluding aromatic carbon atoms) further includes oxo (═O) and its ketal and thioketal protecting groups.

"Heterocycle" or "heterocyclic" as used herein means substituent, moiety or group having a cycloalkyl or aryl ring system wherein one or more, typically 1, 2 or 3, but not all of the carbon atoms consisting of the ring system are replaced by a heteroatom, including, N, O, S, Se, B, Si, P, typically N, O or S, wherein two or more heteroatoms if present may be adjacent to each other or separated by one or more carbon atoms, typically 1-17 carbon atoms, 1-7 or 1-3 carbon atoms. Heterocycles includes heteroaromatic rings (also known as heteroaryls) and heterocycloalkyl rings (also known as heteroalicyclics) containing one to four heteroatoms in the ring(s), where each heteroatom in the ring(s) is typically selected from O, S and N, wherein each heterocyclic group typically has from 3 to 10 total atoms in the heterocyclic ring system(s) for a heterocycloalkyl ring system and 5-10 total atoms for a heteroaromatic ring system. Typically, a heterocyclic ring system of a heterocycle does not contain two adjacent O or S atoms. Heterocycles include C$_3$-C$_{20}$, C$_3$-C$_{14}$, C$_3$-C$_{10}$, C$_3$-C$_8$, C$_3$-C$_6$ or C$_3$-C$_5$ heterocycles for non-aromatic heterocycles in which the numerical indicator is the total number of atoms in the non-aromatic heterocyclic ring system including carbon atoms and heteroatoms and further include C$_5$-C$_{24}$, C$_5$-C$_{14}$, C$_5$-C$_{12}$, C$_5$-C$_{10}$, C$_5$-C$_8$ or C$_5$-C$_6$ heterocycles for aromatic heterocycles (i.e., heteroaryl) in which the numerical indicator is the total number of atoms in the aromatic heterocyclic ring system including carbon atoms and heteroatoms Non-aromatic heterocyclic substituents, moieties or groups (also known as heterocycloalkyls) have at least 3 atoms in their ring system in which at least one atom is a heteroatom and least one atom is a carbon atom in which the carbon atom(s) and heteroatom(s) do not form an aromatic ring system, and aromatic heterocyclic groups have at least 5 atoms in their ring system in which at least one atom is a heteroatom and least one atom is a carbon atom in which the carbon atom(s) and heteroatom(s) form an aromatic ring system, and include benzo-fused heteroaromatic ring systems. Heterocyclic substituents, moieties or groups with 3, 4, 5, 6 and 10 atoms include by way of example and not limitation aziridinyl, azetidinyl, thiazolyl, pyridyl and quinolinyl, respectively.

Nonaromatic heterocyclic substituents, moieties or groups include by way of example and not limitation pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Non-aromatic heterocycles may be substituted with one or two oxo (═O) moieties, including for example pyrrolidin-2-one.

Aromatic heterocycles (i.e., heteroaryls) include, by way of example and not limitation, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzo-thiophenyl, benzothiazolyl, benzoxazolyl, quinazolinyl, quinoxalinyl, naphthyridinyl, and furopyridinyl.

When heterocycle is used as a substituent to a larger structure or moiety the heterocycle is attached to the structure or moiety with which it is associated through a carbon atom or a heteroatom of the heterocycle, where such an attachment does not result in an unstable or disallowed formal oxidation state of that carbon or heteroatom. A heterocycle that is C-linked is bonded to a structure or another moiety or group through a carbon atom of the heterocycle and include moieties indicated as —C<heterocycle where C< represents a carbon atom in a heterocycle ring. A heterocycle that is N-linked is a nitrogen containing heterocycle that is bonded to a nitrogen of the heterocycle ring in which it resides and sometimes is described as —N<heterocycle where N< represents a nitrogen of the heterocycle. Thus, nitrogen-containing heterocyclic substituents may be C-linked or N-linked to the structure or moiety to which it is associated and includes by way of example and not limitation pyrrole substituents, which may be pyrrol-1-yl (N-linked) or pyrrol-3-yl (C-linked), imidazole substituents, which may be imidazol-1-yl or imidazol-3-yl (both N-linked) or imidazol-2-yl, imidazol-4-yl or imidazol-5-yl (all C-linked). Typically, a heterocycle is a $C_{3-20}$ non-aromatic heterocycle or a $C_5$-$C_{24}$ aromatic heterocycle (i.e., a heteroaryl), wherein the number indicator includes all of the atoms of the heterocycle whether that atom is a carbon atom or a heteroatom.

"Heteroaryl" as used herein means an aryl ring system wherein one or more, typically 1, 2 or 3, but not all of the carbon atoms comprising the aryl ring system are replaced by a heteroatom which is an atom other than carbon, including, N, O, S, Se, B, Si, P, typically, sulfur (—S—), oxygen (—O—) or nitrogen or a nitrogen-containing moiety (e.g., —NX—, wherein X is —H, a protecting group or $C_{1-6}$ optionally substituted alkyl, aryl or C-linked heterocycle), wherein the heteroatom participates in the conjugated system either through pi-bonding with an adjacent atom in the ring system or through a lone pair of electrons on the heteroatom and may be optionally substituted on one or more carbons or heteroatoms, or a combination of both, in a manner which retains the cyclically conjugated system.

Heterocycles and heteroaryls, include, by way of example and not limitation, heterocycles and heteroaryls described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. 1960, 82:5545-5473, particularly pp 5566-5573, which is incorporated by reference herein). Depending on the structure, a heterocycle or heteroaryl moiety or group can be a monoradical or a diradical (i.e. a heterocyclo or heteroarylene). Typically, a C-linked heterocycle is related to a parent heterocycloalkane or heteroarene by removal of a hydrogen atom form a carbon atom of a cyclic ring system comprising the heterocycloalkane or heteroarene and an N-linked heterocycle is typically related to a parent nitrogen-containing heterocycloalkane or heteroarenes by removal of a hydrogen atom or an electron from a nitrogen heteroatom of its nitrogen-containing ring system of which it is comprised. A heterocyclo or heteroarylene is typically related to a parent C-linked or N-linked heterocycle or heteroaryl by removal of a hydrogen atom from another atom, typically a carbon atom from the same or different ring system comprising the heterocycle or heteroaryl. Examples of heteroaryls include by way of example and not limitation pyridyl, thiazolyl, pyrimidinyl, furanyl, thienyl, pyrrolyl, pyrazolyl, purinyl, imidazolyl, benzofuranyl, indolyl, isoindolyl, quinolinyl, isoquinolinyl, benzimidazolyl, pyridazinyl, pyrazinyl, benzothiopyran, benzotriazine, isoxazolyl, pyrazolopyrimidinyl, quinoxalinyl, thiadiazolyl, triazolyl and the like. Heterocycles that are not heteroaryls include, by way of example and not limitation, tetrahydrothiophenyl, tetrahydrofuranyl, indolinyl, piperidinyl, pyrrolidinyl, 2-pyrrolidonyl, tetrahydroquinolinyl, tetrahydroisoquinolinyl, decahydroquinolinyl, octahydroisoquinolinyl, 2H-pyrrolyl, 3H-indolyl, 4H-quinolizinyl, imidazolidinyl, imidazolinyl, pyrazolidinyl, piperazinyl, quinuclidinyl, morpholinyl, oxazolidinyl and the like.

Other heteroaryls include, by way of example and not limitation, the following moieties:

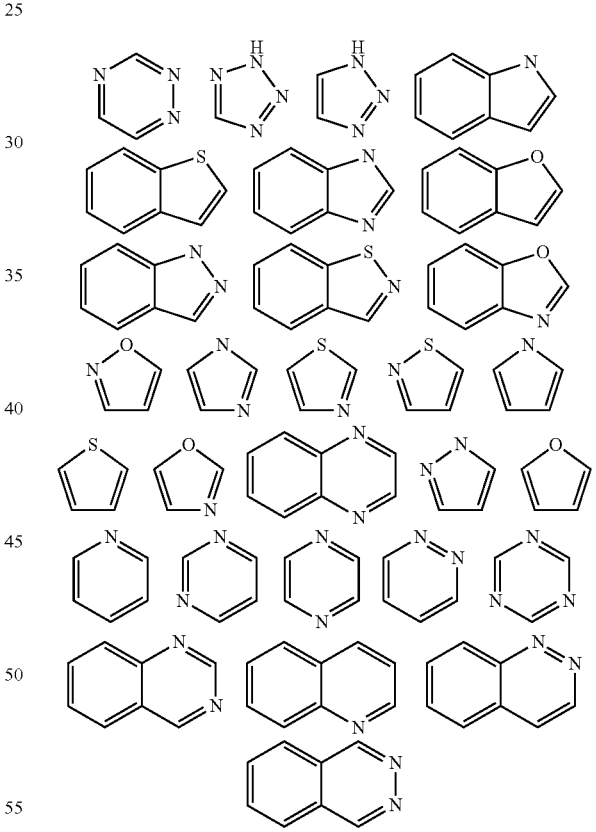

Monocyclic heteroaryls include, by way of example and not limitation, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Heteroaryls include those substituents, moieties or groups containing 0-3 N atoms, 1-3 N atoms or 0-3 N atoms, 0-1 O atoms and 0-1 S atoms. A heteroaryl may be monocyclic or bicyclic. The ring system of a heteroaryls ring typically contains 1-9 carbons. Monocyclic heteroaryls typically are, but are not limited to heteroaryls having 5 to 6 total number of atoms in its aromatic ring system in which at least one is a carbon atom, i.e., $C_5$ or $C_6$ heteroaryl, and are sometimes referred to as 5-membered or 6-membered heteroaryls. Bicyclic heteroaryls typically are, but are not limited to $C_8$-$C_{10}$ heteroaryls. Depending on the structure, a heteroaryl group or moiety can be a monoradical or a diradical (i.e., a heteroarylene group, also referred to as a heteroarenediyl).

"Heterocycloalkyl" or "heteroalicyclic" as used herein means a cycloalkyl group, moiety or substituent wherein at least on carbon of the cycloalkyl chain is replaced with a heteroatom selected from the group consisting of nitrogen, oxygen and sulfur. The heterocycloalkyl may be fused with an aryl or heteroaryl. Heterocycloalkyls, also referred to as non-aromatic heterocycles, include by way of example and not limitation those having the following structure wherein the radical center is present on a carbon atom or nitrogen heteroatom of the cyclic ring system.

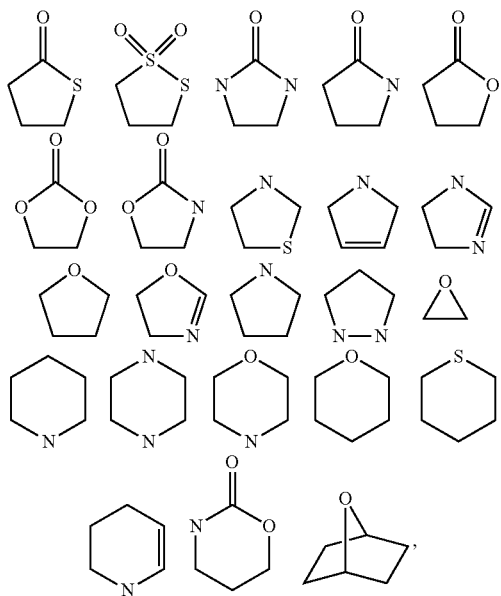

Heterocycloalkyl further includes, by way of example and not limitation, oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. Heteroalicyclics further includes all ring forms of carbohydrates, including but not limited to monosaccharides, disaccharides and oligosaccharides. Typically, a heterocycloalkyl is a $C_3$-$C_{20}$ heterocycloalkyl and includes $C_5$-$C_{14}$ or $C_5$-$C_{10}$ heterocycloalkyl, wherein the number indicates the total number of atom, whether carbon atoms or heteroatoms, in its ring system. A heterocycloalkyl contains at least one heteroatom and at least one carbon atom and may contain 0-2 N atoms, 0-2 O atoms or 0-1 S atoms or a combination thereof.

"Heteroarylalkylene" as used herein means a substituent, moiety or group where a heteroaryl moiety is bonded to an alkylene moiety, i.e., -alkylene-heteroaryl, where alkylene and heteroaryl groups are as described above. When heteroarylalkylene is used as a substituent to a structure the alkylene moiety of the heteroarylalkyl is attached to the structure with which it is associated through a sp³ radical carbon of the alkylene moiety and includes —$C_1$-$C_{20}$ alkylene-($C_5$-$C_{24}$ heteroaryl), —$C_1$-$C_8$ alkylene-($C_5$-$C_{14}$ heteroaryl), —$C_1$-$C_6$ alkylene-($C_5$-$C_{10}$ heteroaryl) or —$C_1$-$C_4$ alkylene-($C_5$-$C_{10}$ heteroaryl) substituents, moieties or groups such as —(CH$_2$)$_n$-$C_5$-$C_{10}$ heteroaryl where n is 1, 2, 3, 4, 5 or 6.

"Alkylheteroarylene" as used herein means a substituent, moiety or group where a heteroarylene moiety is bonded to an alkyl moiety, i.e., -heteroarylene-alkyl, where heteroarylene and alkyl groups are as described above. When alkyl-heteroarylene is used as a substituent to a structure the heteroaryl moiety of the alkylheteroarylene is attached to the structure with which it is associated through an radical aromatic carbon or heteroatom of the heteroarylene moiety, and includes —$C_5$-$C_{24}$ heteroarylene-($C_1$-$C_{20}$ alkyl), —$C_5$-$C_{14}$ heteroarylene-($C_1$-$C_8$ alkyl), —$C_5$-$C_{10}$ heteroarylene-($C_1$-$C_6$ alkyl) or —$C_5$-$C_{10}$ heteroarylene-($C_1$-$C_4$ alkyl).

"Halogen" or "halo" as used herein means fluorine, chlorine, bromine or iodine, and typically includes fluorine, chlorine or bromine, more typically fluorine or chlorine.

"Haloalkyl" as used herein means an alkyl substituent moiety or group in which one or more of its hydrogen atoms are replaced by one or more independently selected halide atoms. Haloalkyl includes $C_1$-$C_{20}$ haloalkyl, $C_1$-$C_8$ haloalkyl, $C_1$-$C_6$ haloalkyl or $C_1$-$C_4$ haloalkyl, wherein the number indicates the number of carbon atoms in the alkyl moiety. Exemplary but non-limiting $C_1$-$C_4$ haloalkyls are —CH$_2$Cl, CH$_2$Br, —CH$_2$I, —CHBrCl, —CHCl—CH$_2$Cl and —CHCl—CH$_2$I.

"Haloalkylene" as used herein means an alkylene substituent, moiety or group in which one or more of its hydrogen atoms are replaced by one or more halide atoms. Haloalkylene includes $C_1$-$C_{20}$ haloalkylenes, $C_1$-$C_8$ haloalkylenes, $C_1$-$C_6$ haloalkylenes or $C_1$-$C_4$ haloalkylenes.

"Fluoroalkyl" as used herein means an alkyl in which one or more of its hydrogen atoms are replaced by a fluorine atom. Fluoroalkyl includes $C_1$-$C_{20}$ fluoroalkyls, $C_1$-$C_8$ fluoroalkyls, $C_1$-$C_6$ fluoroalkyls or $C_1$-$C_4$ fluoroalkyls. Exemplary but non-limiting fluoroalkyls include —CH$_3$F, —CH$_2$F$_2$ and —CF$_3$ and perfluroalkyls.

"Fluoroalkylene" as used herein means an alkylene substituent, moiety or group in which one or more hydrogen atoms of an alkylene are replaced by a fluorine atom. Exemplary but non-limiting fluoroalkylene includes $C_1$-$C_{20}$ fluoroalkylenes, $C_1$-$C_8$ fluoroalkylenes, $C_1$-$C_6$ fluoroalkylenes or $C_1$-$C_4$ fluoroalkylenes.

"O-linked moiety", "O-linked group" and like terms as used herein refers to an oxygen-based group, moiety or substituent that is attached to another organic moiety or structure directly though an oxygen atom of the oxygen-based group, moiety or substituent. An O-linked group may be a monovalent O-linked moiety and includes but are not limited to moieties such as —OH, an ester, such as acetoxy, i.e., —O—C(=O)—CH$_3$, or acyloxy, i.e., —O—C(=O)—R, wherein R is —H, optionally substituted $C_1$-$C_{20}$ alkyl, optionally substituted $C_3$-$C_{20}$ cycloalkyl, optionally substituted $C_2$-$C_{20}$ alkenyl, optionally substituted $C_2$-$C_{20}$ alkynyl, optionally substituted $C_6$-$C_{24}$ aryl, optionally substituted $C_5$-$C_{20}$ heteroaryl or optionally substituted C-linked $C_3$-$C_{20}$ heterocycle as defined herein. When O-linked moiety is used as a substituent to a larger structure or moiety an oxygen atom of the O-linked moiety is directly attached to the structure or moiety with which it is associated.

Monovalent O-linked moieties further include ether and silyl ether moieties such as $C_1$-$C_{20}$ alkyloxy, $C_6$-$C_{24}$ aryloxy (Aryl-O—), phenoxy (Ph-O—), benzyloxy (Bn-O—), $C_5$-$C_{24}$ heteroaryloxy (Het-O—) and silyloxy, or are represented by R'O—, wherein R' is optionally substituted $C_1$-$C_{20}$ alkyl, $C_6$-$C_{24}$ aryl, phenyl, benzyl (—CH$_2$Ph), $C_5$-$C_{24}$ heteroaryl or silyl, i.e., $(R)_3Si$—, wherein each R independently is $C_1$-$C_{20}$ alkyl or $C_6$-$C_{24}$ aryl, optionally substituted. Other monovalent O-linked moieties are carbamates having the structure —O—C(=O)N(R)$_2$, wherein each R independently are —H, optionally substituted $C_1$-$C_{20}$ alkyl, optionally substituted $C_3$-$C_{20}$ cycloalkyl, optionally substituted $C_2$-$C_{20}$ alkenyl, optionally substituted $C_2$-$C_{20}$ alkynyl or another monovalent C-linked moiety as defined herein, or carbonates having the structure —O—C(=O)OR wherein R is optionally substituted $C_1$-$C_{20}$ alkyl or another monovalent C-linked moiety, and —OR$^{RP}$, wherein R$^{RP}$ is a protecting group, or an O-linked moiety may be divalent, i.e., =O or —OCH$_2$CH$_2$O—, as defined herein.

Divalent O-linked moieties include =O, or are moieties that comprise a cyclic ketal. Typically, cyclic ketals and cyclic thioketals comprise an optionally substituted alkylene moiety containing about 2-20 carbon atoms, typically 2 to 3, that connect the two heteroatoms of the ketal, and a carbon of another organic moiety, to which the heteroatoms are attached whereby a spiro ring system is defined. Typically, the alkyl moiety is a straight chain $C_2$-$C_6$ alkylene (i.e., —(CH$_2$)$_{2-6}$—), optionally substituted, or a branched $C_3$-$C_6$ alkylene, including structures such as —CH$_2$C(CH$_3$)—, —CH$_2$CH(CH$_3$)—, —CH$_2$—CH$_2$—, —[CH$_2$]$_{2,3}$—, —CH$_2$—[C—(C$_1$-C$_4$ alky)$_2$]$_{1, 2, 3}$—, —CH(C$_1$-C$_4$ alkyl)-[CH(C$_1$-C$_4$ alkyl)]$_{1, 2, 3}$— and —C(C$_1$-C$_4$ alkyl)$_2$-[CH(C$_1$-C$_4$ alkyl)]$_{1, 2, 3}$—, wherein $C_1$-$C_4$ alkyl are independently selected.

Divalent O-linked moieties that comprise a cyclic ketal typically have the structure —O—C(R)$_2$—C(R)$_2$—O—, wherein —C(R)$_2$—C(R)$_2$— is the optionally substituted $C_{2-6}$ alkylene, previously defined, and each R independently is —H or $C_1$-$C_4$ alkyl or two of R and the carbon(s) to which they are attached comprise a $C_3$-$C_6$ cycloalkyl moiety and the remaining R independently are —H or $C_1$-$C_4$ alkyl or two of R together on adjacent carbon atoms form an o-catechol, where the remaining R are replaced by a double bond of an optionally substituted arylene.

"C-linked moiety", "C-linked group" and like terms as used herein refers to a substituent, moiety or group that is attached to another organic moiety directly though a carbon atom of the C-linked moiety, group or substituent. A C-linked moiety may be monovalent, including but not limited to groups such as acyl, i.e., —C(=O)—R, wherein R is —H, optionally substituted $C_1$-$C_{20}$ alkyl, optionally substituted $C_3$-$C_{20}$ cycloalkyl, optionally substituted $C_2$-$C_{20}$ alkenyl, optionally substituted $C_2$-$C_{20}$ alkynyl, optionally substituted $C_6$-$C_{24}$ aryl, optionally substituted $C_5$-$C_{24}$ heteroaryl or optionally substituted $C_3$-$C_{20}$ or $C_5$-$C_{24}$ C-linked heterocycle or carboxylate, i.e., —C(=O)—OR, wherein R is —H, or its corresponding salt represented by —C(=O)—O, or is as previously defined for ester wherein R includes $C_1$-$C_{20}$ alkyl, $C_6$-$C_{24}$ aryl, a C-linked $C_5$-$C_{24}$ heteroaryl or a C-linked $C_3$-$C_{20}$ heterocycle or may be divalent, i.e., =C(R$^1$)$_2$, wherein each R$^1$ independently is —H, $C_6$-$C_{24}$ aryl, $C_3$-$C_{20}$ heterocycle, $C_5$-$C_{24}$ heteroaryl, optionally substituted $C_1$-$C_{20}$ alkyl, optionally substituted $C_3$-$C_{20}$ cycloalkyl, optionally substituted $C_2$-$C_{20}$ alkenyl, optionally substituted $C_2$-$C_{20}$ alkynyl or a monovalent O-linked moiety including —OH, —OR$^{PR}$, an O-linked ester, an ether, a carbonate and an O-linked carbamate. When a C-linked moiety is used as a substituent to a structure, a carbon atom of the C-linked moiety is directly attached to the structure with which it is associated through a sp$^3$, sp$^2$, sp or aromatic carbon of the C-linked moiety. Sometimes acyl is specifically excluded as a "monovalent C-linked substituent". In such instances the term "monovalent C-linked moiety" is to be understood as a monovalent C-linked moiety that is defined herein other than acyl.

"N-linked moiety", "N-linked group" and like terms as used herein refers to a nitrogen-based group, moiety or substituent that is attached to another organic moiety directly though a nitrogen atom of the nitrogen-based group, moiety or substituent. N-linked moieties include but not limited to groups such as —NO$_3^-$, —NO$_2$, —NR$^1$R$^2$, —N(R$^1$)C(=O)R$^3$ and —N(R$^1$)C(=O)—NHR$^3$, wherein R$^1$, R$^2$ and R$^3$ independently selected are —H or optionally substituted $C_1$-$C_{20}$ alkyl, —N(R$^1$)C(=O)—O—R$^3$, —N(R$^1$)S(=O)$_2$—R$^3$ and —N(R$^1$)S(=O)—R$^3$, wherein R$^1$ is —H or optionally substituted $C_1$-$C_{20}$ alkyl and R$^3$ is optionally substituted $C_1$-$C_{20}$ alkyl.

"S-linked moiety", "S-linked group" and like terms as used herein refers to an sulfur-based group, moiety or substituent that is attached to another organic moiety directly though a sulfur atom of the sulfur-based group, moiety or substituent. S-linked moieties or groups include, but are not limited to, —SH, —SO$_{32}$—, —S(O)$_q$R$^1$, —S(=O)$_2$N(R$^2$)$_2$ and —S(=O)N(R$^2$)$_2$, wherein q is 0, 1 or 2, wherein each R$^1$ is OH or optionally substituted $C_1$-$C_{20}$ alkyl and each R$^2$ is independently —H or $C_1$-$C_{20}$ alkyl.

"Protecting group" as used here means a moiety or group that prevents or reduces the ability of an atom or functional group to which it is attached from participating in unwanted reactions. Non-limiting example protecting groups include —OR$^{PR}$, wherein R$^{PR}$ is a protecting group for the oxygen atom found in a hydroxyl, while for —C(=O)—OR$^{PR}$, R$^{PR}$ may be a carboxylic acid protecting group; for —SR$^{PR}$, R$^{PR}$ may be a protecting group for sulfur in thiols; and for —NHR$^{PR}$ or —N(R$^{PR}$)$_2$—, at least one of R$^{PR}$ is a nitrogen atom protecting group for primary or secondary amines. Hydroxyl, amine, ketones and other reactive groups may require protection against reactions taking place elsewhere in the molecule. The protecting groups for oxygen, sulfur or nitrogen atoms are usually used to mitigate or prevent unwanted reactions with electrophilic compounds, such as acylating agents. Ketal moieties as described herein may serve as protecting groups for a ketone, which can be removed by chemical synthesis methods. Typically, ketal protecting groups are cyclic ketals, which are divalent O-linked moieties, typically having the structure of —O—CH$_2$—CH$_2$—CH$_2$—O— or —O—CH$_2$—CH$_2$—O— that forms a spiro ring (i.e., a cyclic ketal) with the carbon to which the heteroatoms of this divalent moiety are attached. The protecting groups for =O are usually used to alleviate or prevent unwanted reactions with nucleophilic compounds. Typical protecting groups for atoms or functional groups are given in Greene (1999), "Protective groups in organic synthesis, 3$^{rd}$ ed.", Wiley Interscience.

"Ester" as used herein means a substituent, moiety or group that contains a —C(=O)—O— structure (i.e., ester functional group) wherein the carbon atom of that structure is not directly connected to another heteroatom and is directly connected to —H or another carbon atom. Typically, esters comprise or consist of an organic moiety containing 1-50 carbon atoms, 1-20 carbon atoms, 1-8 carbon atoms or 1-6 carbon atoms and 0 to 10 independently selected heteroatoms (e.g., O, S, N, P, Si), typically 0-2 where the organic moiety is carbon bonded through the —C(=O)—O— structure and include ester moieties such as organic moiety-C(=O)—O— and —C(=O)—O— organic moiety. The organic moiety usually comprises one or more of any of the organic groups described herein, e.g., $C_1$-$C_{20}$ alkyl moieties, $C_2$-$C_{20}$ alkenyl moieties, $C_2$-$C_{20}$ alkynyl moieties, $C_6$-$C_{24}$ aryl moieties, $C_3$-$C_{20}$ heterocycles or substituted derivatives of any of these, e.g., comprising 1, 2, 3, 4 or more substituents, where each substituent is independently chosen, or is hydrogen. Exemplary, non-limiting substitutions for hydrogen atoms or carbon atoms in these organic groups are as described above for substituted $C_1$-$C_{20}$ alkyl and other substituted moieties and are independently chosen. The substitutions typically are those used to replace one or more carbon atoms of an alkyl or alkyl-containing moiety as described herein, (i.e., an $sp^3$ carbon is replaced with a non-carbon atom or a group of non-carbon atoms such as an Ls as defined herein) and/or typically have one or more hydrogen atoms replaced by a non-carbon atom such as halogen, —$NH_2$, —OH or =O.

Exemplary esters include by way of example and not limitation formate acetate, propionate, isopropionate, isobutyrate, butyrate, valerate, isovalerate, caproate, isocaproate, hexanoate, heptanoate, octanoate, phenylacetate esters or benzoate esters. When ester is used as a substituent of a larger structure or moiety the single bonded oxygen of the ester functional group is single bonded to the structure or moiety with which it is associated (i.e., the ester substituent has the structure of organic moiety-C(=O)O— or —OC(=O)R wherein R is as defined as a substituent for an O-linked moiety, or is hydrogen. When R is hydrogen or $C_1$-$C_{19}$ alkyl the carbonyl carbon is counted in its number identification. Thus a $C_1$ ester is —OC(=O)—H, a $C_2$ ester is —OC(=O)$CH_3$ and a $C_2$-$C_{20}$ alkyl ester is —OC(=O)—($C_1$-$C_{19}$ alkyl). An ester can be removed by chemical synthesis methods and sometimes may serve to form a prodrug of a compound whereby metabolism in cells or biological fluids are capable of removing the ester functional group through spontaneous hydrolysis or enzymatic action.

"Acetal", "thioacetal", "ketal", "thioketal" and the like as used herein means a moiety, group or substituent comprising or consisting of a carbon to which is bonded two of the same or different heteroatoms wherein the heteroatoms are independently selected S and O and are included within the definition of a divalent O-linked moiety as described elsewhere herein. For acetal the carbon of the acetal functional group has two single bonded oxygen atoms, a hydrogen atom and a single bonded carbon of an organic moiety. For ketal, the carbon of the ketal functional group has two single bonds to two oxygen atoms and two single bonds to two independently selected organic moieties where the organic moieties are as described herein for alkyl or optionally substituted alkyl group or the carbon of the ketal functional group is a carbon of a cyclic ring system. For thioacetals and thioketals one or both of the oxygen atoms in acetal or ketal, respectively, is replaced by sulfur. The oxygen or sulfur atoms in ketals and thioketals are sometimes linked by an optionally substituted alkyl moiety. Typically, the alkyl moiety is an optionally substituted $C_1$-$C_{20}$ alkyl or branched alkyl structure such as —C($CH_3$)$_2$—, —CH($CH_3$)—, —$CH_2$—, —$CH_2$—$CH_2$—, —C[($C_1$-$C_4$ alkyl)$_2$]$_{1, 2, 3}$— or —[CH($C_1$-$C_4$ alkyl)]$_{1, 2, 3}$—. Some of those moieties can serve as protecting groups for an aldehyde or ketone include, by way of example and not limitation, acetals for aldehydes and ketals for ketones that contain —O—$CH_2$—$CH_2$—$CH_2$—O— or —O—$CH_2$—$CH_2$—O— moieties so as to form a spiro ring with the carbonyl carbon. An acetal, thioacetal, ketal or thioketal and can be removed by chemical synthesis methods and sometimes may serve to form a prodrug of a compound whereby metabolism in cells or biological fluids are capable of degrading or removing the acetal, thioacetal, ketal or thioketal functional group through enzymatic oxidation.

"Ether" as used herein means an organic moiety, group or substituent that comprises or consists of 1, 2, 3, 4 or more —O— moieties, usually 1 or 2, wherein no two —O— moieties are immediately adjacent to each other (i.e., are not directly attached to each other to form a peroxide). Typically, ethers comprise an organic moiety containing 1-50 carbon atoms, 1-20 carbon atoms, 1-8 carbon atoms or 1-6 carbon atoms and 0 to 10 independently selected heteroatoms (e.g., O, S, N, P, Si), typically 0-2. An ether moiety, group or substituent includes organic moiety-O— wherein the organic moiety is as described herein for optionally substituted $C_1$-$C_{20}$ alkyl group. When ether is used as a substituent of a larger structure or moiety the oxygen of the ether functional group is single bonded to the structure or moiety with which it is associated. In that context the substituent it is sometimes designated as "alkoxy". Alkoxy includes $C_1$-$C_4$ ether substituents such as, by way of example and not limitation, methoxy, ethoxy, propoxy, isopropoxy and butoxy, wherein the numbering indicates the number of carbon atoms in the alkyl moiety of the ether. Ether further includes those substituents, moieties or groups that contain one (excluding ketal) or more —$OCH_2CH_2O$—, moieties in sequence (i.e., polyethylene or PEG moieties). An ether substituent can be removed by chemical synthesis methods and sometimes may serve to form a prodrug of a compound whereby metabolism in cells or biological fluids are capable of degrading or removing the ether functional group through enzymatic oxidation or in certain cases by hydrolysis under acidic conditions of the digestive system.

"Carbonate" as used here means a substituent, moiety or group that contains a —O—C(=O)—O— structure (i.e., carbonate functional group). Typically, carbonate groups as used herein comprise or consist of an organic moiety containing 1-50 carbon atoms, 1-20 carbon atoms, 1-8 carbon atoms or 1-6 carbon atoms and 0 to 10 independently selected heteroatoms (e.g., O, S, N, P, Si), typically 0-2, bonded through the —O—C(=O)—O— structure, e.g., organic moiety-O—C(=O)—O—. When carbonate is used as a substituent of a structure one of the singly bonded oxygen atoms of the carbonate functional group is single bonded to a structure with which it is associated while the other oxygen atom is single bonded to another organic moiety. A carbonate substituent can be removed by chemical synthesis methods and sometimes may serve to form a prodrug of a compound whereby metabolism in cells or biological fluids are capable of degrading or removing the carbonate functional group through spontaneous or enzymatic hydrolysis.

"Carbamate" or "urethane" as used here means a substituent, moiety or group that contains a —O—C(=O)N($R^{PR}$)—, —O—C(=O)N($R^{PR}$)$_2$, —O—C(=O)NH(optionally substituted $C_1$-$C_{20}$ alkyl) or —C(=O)N(optionally substituted $C_1$-$C_{20}$ alkyl)$_2$ structure (i.e., carbamate functional group) wherein each $R^{PR}$ and optionally substituted $C_1$-$C_{20}$ alkyl are independently selected with $R^{PR}$ independently selected from the group consisting of —H, a protecting group, an organic moiety as described herein for ester, substituted alkyl and optionally substituted alkyl. Typically, carbamate groups as used herein comprise or consist of an organic moiety containing 1-50 carbon atoms, 1-20 carbon atoms, 1-8 carbon atoms, or 1-6 carbon atoms and 0 to 10 independently selected heteroatoms (e.g., O, S, N, P, Si), typically 0-2, single bonded through the —O—C(=O)—N$R^{PR}$— structure, e.g., organic moiety-O—C(=O)—N($R^{PR}$)$_2$ or —O—C(=O)—N$R^{PR}$— organic moiety. When carbamate is used as a substituent to a structure the singly bonded oxygen (O-linked) or nitrogen (N-linked) of the carbamate functional group is single bonded to the structure with which it is associated. The linkage of the carbamate substituent is either explicitly stated (N- or O-linked) or implicit in the context to which this substituent is referred. A carbamate substituent can be removed by chemical synthesis methods and sometimes may serve to form a prodrug of a compound whereby metabolism in cells or biological fluids are capable of degrading or removing the carbamate functional group through enzymatic hydrolysis.

For any substituent group or moiety described by a given range of carbon atoms, the designated range means that any individual number of carbon atoms is described. Thus, reference to, e.g., "$C_1$-$C_4$ optionally substituted alkyl", "$C_2$-$C_6$ optionally substituted alkenyl" or "$C_3$-$C_8$ optionally substituted heterocycle" specifically means that 1, 2, 3 or 4 optionally substituted carbons atoms of alkyl moiety as defined herein is present or a 2, 3, 4, 5 or 6 optionally substituted carbons atoms of an alkenyl moiety as defined herein is present, or a cyclic ring system containing a total of 3, 4, 5, 6, 7 or 8 carbon atoms and heteroatoms comprising the heterocycle as defined herein is present. All such designations are expressly intended to disclose all of the individual carbon atom groups and thus "$C_1$-$C_4$ optionally substituted alkyl" includes, e.g., substituted or unsubstituted 2 carbon alkyl, substituted or unsubstituted 3 carbon alkyl, and substituted or unsubstituted 4 carbon alkyl, including all positional isomers and the like are disclosed and can be expressly referred to or named. For esters, carbonates and carbamates defined by a given range of carbon atoms, the designated range includes the carbonyl carbon of the respective functional group. Thus a $C_1$ ester refers to a formate ester and a $C_2$ ester refers to an acetate ester. The organic substituents, moieties and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions herein that results in those having a pentavalent carbon are specifically excluded.

"S6K-dependent", "S6K-mediated" or like terms as used herein means a disease, disorder or condition whose etiology, progression or persistence is effected by in whole or in part by signaling through one or more S6K subtypes, including by way of example and not limitation S6K1. S6K-dependent or S6K-mediated diseases and conditions include but not limited to proliferative diseases or conditions such as cancer, and neurological diseases such as Fragile X syndrome. Further S6K-dependent and S6K-mediated diseases include peripheral diseases relating to metabolism such as diabetes and non-productive cellular remodeling such as pulmonary fibrosis and non-alcoholic steatohepatitis (NASH).

"S6K selective agents", S6K selective compounds" and like terms as used herein means agents or compounds that interact with the S6K in preference to other kinases. Typically, that preference is manifested by 10-fold stronger binding affinity of the agent to S6K in comparison to other kinases as measured experimentally.

"Pharmaceutically-acceptable formulation" as used herein means a composition comprising an active pharmaceutical ingredient, such as a compound having the formula I-IX in addition to one or more pharmaceutically acceptable recipients or refers to a composition prepared from an active pharmaceutical ingredient and one or more pharmaceutically acceptable excipients, wherein the composition is suitable for administration to a subject, such as a human or an animal, in need thereof. For a pharmaceutically acceptable formulation to be suitable for administration to a human the formulation must have biological activity for treating or preventing a disease or condition disclosed herein or an expectation must exist that the formulation would have a desired activity towards an "intent to treat" disease or condition. Typically, the "intent to treat" disease or condition is a S6K-mediated condition or disease. More typically the disease or condition to be treated or prevented is a S6K-mediated disease or condition. A pharmaceutically acceptable formulation that is suitable for administration to an animal (i.e., a non-human mammal) does not necessarily require a biological activity for treating or preventing a disease or condition, and may be administered to the animal in order to evaluate a potential pharmacological or biological activity of a Formula I-IX compound. Those formulations must therefore be suitable for treating or preventing a disease or condition disclosed herein in an animal in need thereof or is suitable for evaluating a pharmacological or biological activity of a Formula I-IX compound. Compositions that are suitable only for use in vitro assays or which contain a vehicle, component or recipient in an amount not permitted in a drug product are specifically excluded from the definition of a pharmaceutically acceptable formulation.

The pharmaceutically-acceptable formulation may be comprised of, or be prepared from, one, two or more Formula I-IX compounds, typically one or two, and one or more pharmaceutically acceptable recipients. More typically, the formulations will consist essentially of or consist of a single Formula I-IX compound and one or more pharmaceutically acceptable excipients. Other formulations may be comprised of, consist essentially of, or consist of one, two or more Formula I-IX compounds and one two or more compounds in current use for treating S6K-mediated disease or condition disclosed herein and one or more pharmaceutically acceptable excipients. Typically, those formulations will consist essentially of or consist of a single Formula I-IX compound, a single compound in current use for treating a S6K-mediated disease or condition and one or more pharmaceutically acceptable excipients.

"Solid formulation" as used herein refers to a pharmaceutically acceptable formulation comprising at least one Formula I-IX compound and one or more pharmaceutically acceptable excipients in solid form(s) wherein the formulation is in a unit dosage form suitable for administration of a solid. The dosage units include tablets, capsules, caplets, gelcaps, suspensions and other dosage units typically associated with parenteral or enteral (oral) administration of a solid.

"Liquid formulation" as used herein refers to a pharmaceutically acceptable formulation wherein at least one Formula I-IX compound has been admixed or contacted with one or more pharmaceutically acceptable excipients, wherein at least one of the excipients is in non-solid state form in proportions required for a liquid formulation, i.e., such that a majority of the mass amount of the Formula I-IX compound(s) is dissolved into the non-solid excipient. Dosage units containing a liquid formulation include syrups, gels, ointments and other dosage units typically associated with parenteral or enteral administration of a pharmaceutical formulation to a subject in need thereof in liquid form.

"Suspension formulation" as used herein refers to a pharmaceutically acceptable formulation wherein at least one Formula I-IX compound has been admixed or contacted with two or more pharmaceutically acceptable excipients, wherein at least one of the excipients is a liquid and another is a surface active agent in proportions required for a suspension formulation, i.e., such that a majority of the mass amount of the Formula I-IX compound(s) is in the solid state from suspended in the liquid excipient. Dosage units containing a liquid formulation include syrups, gels, ointments and other dosage units typically associated with parenteral or enteral administration of a pharmaceutical formulation to a subject in need thereof in suspension form.

"Prevent", "preventing" and like terms as used herein takes on its normal and customary meaning in the medical arts and therefore does not require that each instance to which the term refers be avoided with certainty.

NUMBERED EMBODIMENTS

The following embodiments exemplify the invention and are not meant to limit the invention in any manner. In certain embodiments, the compounds presented herein possess one or more stereocenters and each center independently exists in either the R or S configuration. The methods and formulations described herein include the use of salts, in particular, pharmaceutically acceptable salts, of compounds having the structure of one of Formulas (I-IX), as well as active metabolites of these compounds having similar physiological activity relative to the parent compound. In some embodiments, the compounds exist as tautomers. Thus, all of those tautomers are included within the scope of the compounds presented herein. In specific embodiments, the compounds described herein will exist as salts, including pharmaceutically acceptable salts. The salt forms include inorganic addition salts such as $F^-$, $Cl^-$, $Br^-$, $I^-$ and sulfate salts and organic addition salts such as mesylate, besylate, tosylate, citrate, succinate, fumarate and malonate.

1. A compound of Formula I having the structure:

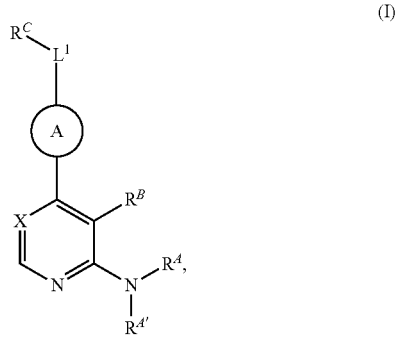

(I)

or a salt, including a pharmaceutically acceptable salt, or a prodrug thereof, wherein X is =N— or a carbon atom that is substituted or unsubstituted;

$R^A$ is —H, —CN, $C_1$-$C_4$alkyl, —C(O)$R^D$, —$SO_2R^D$;

$R^{A'}$ is —H, $C_1$-$C_4$alkyl, or —C(O)$R^D$;

$R^B$ is substituted phenyl or $C_5$-$C_6$ heteroaryl (Ar, or HetAr), either of which is unsubstituted or substituted by up to three $R^E$ independently of one another;

$L^1$ is a bond, or a $C_1$-$C_4$ unbranched alkylene, a $C_3$-$C_6$ cycloalkylene or a 3-6-membered heterocycloalkylene, either one of which is unsubstituted or substituted by one or two $R^F$ independently of one another and/or having one, two or three of its —$CH_2$— groups independently replaced by —O—, —NH—, or —CO— or, $L^1$ is a $C_3$-$C_7$ branched alkylene, which is unsubstituted or substituted by one or two $R^F$ independently of one another, and/or having one, two or three of its —$CH_2$— groups independently replaced by —O—, —NH—, or —CO— and/or having one of its —CH— groups replaced by —N—;

$R^C$ is a $C_6$ or $C_{10}$ aryl or $C_5$-$C_{10}$ heteroaryl, either of which is unsubstituted or substituted by up to three $R^G$ independently of one another;

Ring A is a pyrazole moiety having the structure of:

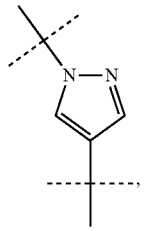

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;

$R^D$ is —H or an unsubstituted or substituted $C_1$-$C_4$ alkyl or an amino acid moiety;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$ alkyl, —S(O)$C_1$-$C_4$ alkyl, —$SO_2C_1$-$C_4$ alkyl, —$NH_2$, —NH$C_1$-$C_4$ alkyl, —N($C_1$-$C_4$ alkyl)$_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl)$_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$ alkyl, —$SO_2C_1$-$C_4$ alkyl, —N($C_1$-$C_4$ alkyl)$_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —$NH_2$, —$NMe_2$, —$CONH_2$, —CONHMe, —$CONMe_2$, —COOH, —$CH_3$ and —$CF_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —$SO_2C_1$-$C_4$alkyl, —$NH_2$, —NH$C_1$-$C_4$ alkyl, —N($C_1$-$C_4$ alkyl)$_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl)$_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —$SO_2C_1$-$C_4$alkyl, —N($C_1$-$C_4$ alkyl)$_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

wherein the remaining aromatic carbon atom(s) of the pyrimidine or pyridine ring of formula I is unsubstituted or independently substituted by $R^J$; and wherein each $R^J$, if present is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —NH$_2$, and —OH.

In certain embodiments of Formula I, X is =N—, or a carbon that is substituted or unsubstituted, $R^A$ is —H and $R^B$ is substituted aryl.

In preferred embodiments of Formula I, $R^A$ is —H, $R^B$ is substituted phenyl, $R^C$ is unsubstituted or substituted phenyl, Ring A is unsubstituted pyrazolyl and $L^1$ is —CH$_2$— or —CHCH$_2$NH$_2$—. $R^J$ is absent.

2. The compound of embodiment 1 wherein Ring A is unsubstituted.
3. The compound of embodiments 1 or 2 wherein $R^A$ is —H and X is =N— or =CH—.
4. The compound of embodiment 1, 2 or 3 wherein $R^B$ is substituted phenyl.
5. The compound of embodiment 4 wherein $R^E$ in $R^B$ is absent or one or two of $R^E$ is present and is halogen or $C_1$-$C_4$ alkoxy.
6. The compound of embodiment 5 wherein one and only one of $R^E$ in $R^B$ is present and is —Cl.
7. The compound of embodiment 6 wherein two of $R^E$ in $R^B$ is present and are independently —F or —OCH$_3$.
8. The compound of any one of embodiments 1 to 7 wherein $R^C$ is substituted phenyl.
9. The compound of embodiment 8 wherein $R^G$ in $R^B$ is —H or $C_1$-$C_4$ fluoroalkyl.
10. The compound of embodiment 9 wherein $R^G$ is —CF$_3$.
11. The compound of any one of embodiments 1 to 10 wherein $L^1$ is —CH($R^F$)—.
12. The compound of embodiment 11 wherein $R^F$ is replaced by —H or is —CH$_2$NH$_2$.
13. A compound of Formula II having the structure:

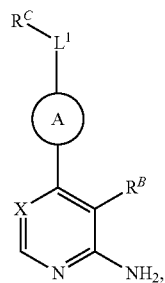

(II)

or a salt, including a pharmaceutically acceptable salt, or a prodrug thereof,
wherein X is =N— or a carbon atom that is substituted or unsubstituted;
$R^B$ is substituted phenyl or $C_5$-$C_6$ heteroaryl (Ar, or HetAr), either of which is unsubstituted or substituted by up to three $R^E$ independently of one another;

$L^1$ is a bond, or a $C_1$-$C_4$ unbranched alkylene, a $C_3$-$C_6$ cycloalkylene or a 3-6-membered heterocycloalkylene, either one of which is unsubstituted or substituted by one or two $R^F$ independently of one another and/or having one, two or three of its —CH$_2$— groups independently replaced by —O—, —NH—, or —CO— or, $L^1$ is a $C_3$-$C_7$ branched alkylene, which is unsubstituted or substituted by one or two $R^F$ independently of one another, and/or having one, two or three of its —CH$_2$— groups independently replaced by —O—, —NH—, or —CO— and/or having one of its —CH— groups replaced by —N—;

$R^C$ is a $C_6$ or $C_{10}$ aryl or $C_5$-$C_{10}$ heteroaryl, either of which is unsubstituted or substituted by up to three $R^G$ independently of one another, Ring A is a pyrazole moiety having the structure of:

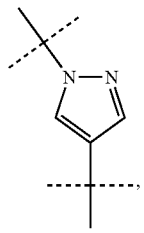

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$ alkyl, —S(O)$C_1$-$C_4$ alkyl, —SO$_2$$C_1$-$C_4$ alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$ alkyl, —SO$_2$$C_1$-$C_4$ alkyl, —N($C_1$-$C_4$ alkyl)$_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —NH$_2$, —NMe$_2$, —CONH$_2$, —CONHMe, —CONMe$_2$, —COOH, —CH$_3$ and —CF$_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$alkyl, —$SO_2C_1$-$C_4$alkyl, —$N(C_1$-$C_4$ alkyl)$_2$, —CN.

In certain embodiments of Formula II at least two adjacent $R^G$ are present that taken together define a substituted or unsubstituted $C_5$-$C_6$ carbocycle or heterocycle, and the remaining $R^G$, if present, is as previously defined;

wherein the remaining aromatic carbon atom(s) of the pyrimidine or pyridine ring of formula II is unsubstituted or independently substituted by $R^J$; and wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —S(O)$C_1$-$C_4$alkyl, —$SO_2C_1$-$C_4$alkyl, —$NH_2$, —$NHC_1$-$C_4$ alkyl, —$N(C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —$NH_2$, and —OH;

In certain embodiments of Formula II, $R^B$ is substituted aryl.

In preferred embodiments of Formula II, X is =N—, or =CH—, $R^B$ is substituted phenyl, $R^C$ is unsubstituted or substituted phenyl, Ring A is unsubstituted pyrazolyl and $L^1$ is —$CH_2$ or —$CHCH_2NH_2$. $R^J$ is absent.

14. A compound of Formula III having the structure:

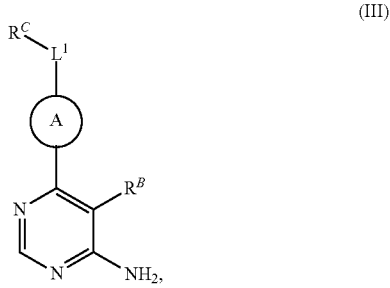

(III)

or a salt, including a pharmaceutically acceptable salt, or a prodrug thereof;

wherein $R^B$ is substituted phenyl or $C_5$-$C_6$ heteroaryl (Ar, or HetAr), either of which is unsubstituted or substituted by up to three $R^E$ independently of one another;

$L^1$ is a bond, or a $C_1$-$C_4$ unbranched alkylene, a $C_3$-$C_6$ cycloalkylene or a 3-6-membered heterocycloalkylene, either one of which is unsubstituted or substituted by one or two $R^F$ independently of one another and/or having one, two or three of its —$CH_2$— groups independently replaced by —O—, —NH—, or —CO— or, $L^1$ is a $C_3$-$C_7$ branched alkylene, which is unsubstituted or substituted by one or two $R^F$ independently of one another, and/or having one, two or three of its —$CH_2$— groups independently replaced by —O—, —NH—, or —CO— and/or having one of its —CH— groups replaced by —N—;

$R^C$ is a $C_6$ or $C_{10}$ aryl or $C_5$-$C_{10}$ heteroaryl, either of which is unsubstituted or substituted by up to three $R^G$ independently of one another, Ring A is a pyrazole moiety having the structure of:

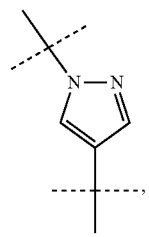

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —$OC_1$-$C_4$ fluoroalkyl, $C_1$-$C_{20}$ alkyl, $C_3$-$C_6$ cycloalkyl, $C_1$-$C_4$ fluoroalkyl, and halogen;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$ alkyl, —S(O)$C_1$-$C_4$ alkyl, —$SO_2C_1$-$C_4$ alkyl, —$NH_2$, —$NHC_1$-$C_4$ alkyl, —$N(C_1$-$C_4$ alkyl)$_2$, —$NO_2$, —CN, —OCN, —COOH, —COO($C_1$-$C_4$ alkyl), —$CONH_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$ alkyl, —$SO_2C_1$-$C_4$ alkyl, —$N(C_1$-$C_4$ alkyl)$_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —$NH_2$, —$NMe_2$, —$CONH_2$, —$CONHMe$, —$CONMe_2$, —COOH, —$CH_3$ and —$CF_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —S(O)$C_1$-$C_4$alkyl, —$SO_2C_1$-$C_4$alkyl, —$NH_2$, —$NHC_1$-$C_4$ alkyl, —$N(C_1$-$C_4$ alkyl)$_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl)$_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$alkyl, —$SO_2C_1$-$C_4$alkyl, —$N(C_1$-$C_4$ alkyl)$_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

wherein the remaining aromatic carbon atom(s) of the pyrimidine or pyridine ring of formula III is unsubstituted or independently substituted by $R^J$; and wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —S(O)$C_1$-$C_4$alkyl, —$SO_2C_1$-$C_4$alkyl, —$NH_2$, —$NHC_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —NH$_2$, and —OH;

In certain embodiments of Formula III, $R^B$ is substituted aryl.

In preferred embodiments of Formula III, $R^B$ is substituted phenyl, $R^C$ is unsubstituted or substituted phenyl, Ring A is unsubstituted pyrazolyl and $L^1$ is —CH$_2$ or —CHCH$_2$NH$_2$, and $R^J$ is absent.

15. A compound of Formula IV having the structure

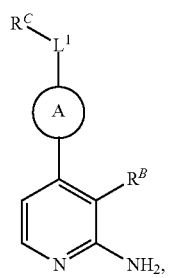

IV or a salt, including a pharmaceutically acceptable salt, or a prodrug thereof, wherein $R^B$ is substituted phenyl or $C_5$-$C_6$ heteroaryl (Ar, or HetAr), either of which is unsubstituted or substituted by up to three $R^E$ independently of one another;

$L^1$ is a bond, or a $C_1$-$C_4$ unbranched alkylene, a $C_3$-$C_6$ cycloalkylene or a 3-6-membered heterocycloalkylene, either one of which is unsubstituted or substituted by one or two $R^F$ independently of one another and/or having one, two or three of its —CH$_2$— groups independently replaced by —O—, —NH—, or —CO— or, $L^1$ is a $C_3$-$C_7$ branched alkylene, which is unsubstituted or substituted by one or two $R^F$ independently of one another, and/or having one, two or three of its —CH$_2$— groups independently replaced by —O—, —NH—, or —CO— and/or having one of its —CH— groups replaced by —N—;

$R^C$ is a $C_6$ or $C_{10}$ aryl or $C_5$-$C_{10}$ heteroaryl, either of which is unsubstituted or substituted by up to three $R^G$ independently of one another;

Ring A is a pyrazole moiety having the structure of:

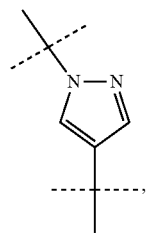

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$ alkyl, —S(O)$C_1$-$C_4$ alkyl, —SO$_2$$C_1$-$C_4$ alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$ alkyl, —SO$_2$$C_1$-$C_4$ alkyl, —N($C_1$-$C_4$ alkyl)$_2$, —CN.

In certain embodiments at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —NH$_2$, —NMe$_2$, —CONH$_2$, —CONHMe, —CONMe$_2$, —COOH, —CH$_3$ and —CF$_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —SO$_2$$C_1$-$C_4$alkyl, —N($C_1$-$C_4$ alkyl)$_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

wherein the remaining aromatic carbon atom(s) of the pyrimidine or pyridine ring of formula IV is unsubstituted or independently substituted by $R^J$; and wherein each $R^J$, if present is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —NH$_2$, and —OH.

In certain embodiments of Formula IV, $R^B$ is substituted aryl.

In preferred embodiments of Formula IV, $R^B$ is substituted phenyl, $R^C$ is substituted phenyl, Ring A is unsubstituted pyrazolyl and $L^1$ is —CH$_2$ or —CHCH$_2$NH$_2$, and $R^J$ is absent.

16. A compound of Formula V having the structure:

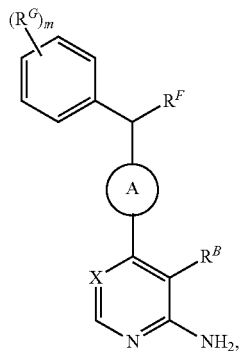

or a salt, including a pharmaceutically acceptable salt, or a prodrug thereof;
wherein X is =N— or a carbon atom that is substituted or unsubstituted;
$R^B$ is substituted phenyl or $C_5$-$C_6$ heteroaryl (Ar, or HetAr), either of which is unsubstituted or substituted by up to three $R^E$ independently of one another;
Ring A is a pyrazole moiety having the structure of:

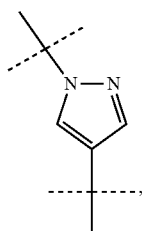

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;
each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$ alkyl, —S(O)$C_1$-$C_4$ alkyl, —SO$_2$$C_1$-$C_4$ alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$ alkyl, —SO$_2$$C_1$-$C_4$ alkyl, —N($C_1$-$C_4$ alkyl)$_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;
each $R^F$, if present, is independently selected from the group consisting of halogen, —OH, —CN, —NH$_2$, —NMe$_2$, —CONH$_2$, —CONHMe, —CONMe$_2$, —COOH, —CH$_3$ and —CF$_3$;
each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH ($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —SO$_2$$C_1$-$C_4$alkyl, —N($C_1$-$C_4$ alkyl)$_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;
subscript m is 1, 2 or 3;
wherein the remaining aromatic carbon atom(s) of the pyrimidine or pyridine ring of formula V is unsubstituted or independently substituted by $R^J$; and
wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —NH$_2$, and —OH.

In certain embodiments of Formula V, $R^B$ is substituted aryl.

In preferred embodiments of Formula V, X is =N— or =CH—, $R^B$ is substituted phenyl, Ring A is unsubstituted pyrazolyl and $R^F$ is replaced by —H or is —CH$_2$NH$_2$, $R^G$ is absent or is halogen or $C_1$-$C_4$ fluoroalkyl; and $R^J$ is absent.

17. A compound of Formula VI having the structure:

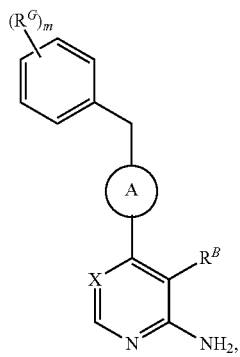

or a salt, including a pharmaceutically acceptable salt, or a prodrug thereof;
wherein X is =N— or a carbon atom that is substituted or unsubstituted;
$R^B$ is substituted phenyl or $C_5$-$C_6$ heteroaryl (Ar, or HetAr), either of which is unsubstituted or substituted by up to three $R^E$ independently of one another;

Ring A is a pyrazole moiety having the structure of:

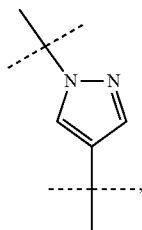

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —$OC_1$-$C_4$ fluoroalkyl, $C_1$-$C_{20}$ alkyl, $C_3$-$C_6$ cycloalkyl, $C_1$-$C_4$ fluoroalkyl, and halogen;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$ alkyl, —$S(O)C_1$-$C_4$ alkyl, —$SO_2C_1$-$C_4$ alkyl, —$NH_2$, —$NHC_1$-$C_4$ alkyl, —$N(C_1$-$C_4$ alkyl$)_2$, —$NO_2$, —CN, —OCN, —COOH, —COO($C_1$-$C_4$ alkyl), —$CONH_2$, —CONH($C_1$-$C_4$ alkyl), —CON($C_1$-$C_4$ alkyl$)_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$ alkyl, —$SO_2C_1$-$C_4$ alkyl, —$N(C_1$-$C_4$ alkyl$)_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —$S(O)C_1$-$C_4$alkyl, —$SO_2C_1$-$C_4$alkyl, —$NH_2$, —$NHC_1$-$C_4$ alkyl, —$N(C_1$-$C_4$ alkyl$)_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl$)_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$alkyl, —$SO_2C_1$-$C_4$alkyl, —$N(C_1$-$C_4$ alkyl$)_2$,—CN. In certain embodiments at least two adjacent $R^G$ are present that taken together define a substituted or unsubstituted $C_5$-$C_6$ carbocycle or heterocycle, and the remaining $R^G$, if present, is as previously defined;

subscript m is 1, 2 or 3;

wherein the remaining aromatic carbon atom(s) of the pyrimidine or pyridine ring of formula VI is unsubstituted or independently substituted by $R^J$; and wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —$S(O)C_1$-$C_4$alkyl, —$SO_2C_1$-$C_4$alkyl, —$NH_2$, —$NHC_1$-$C_4$ alkyl, —$N(C_1$-$C_4$ alkyl$)_2$, and —CN, or is selected from the group consisting of $C_1$-$C_4$ alkyl, $C_1$-$C_4$ fluoroalkyl, $C_1$-$C_4$ alkoxy, halogen, —CN, —$NH_2$, and —OH.

In certain embodiments of Formula VI, $R^B$ is substituted aryl.

In preferred embodiments of Formula VI, X is =N— or =CH—, $R^B$ is substituted phenyl and Ring A is unsubstituted pyrazolyl, $R^G$ is absent or is halogen or $C_1$-$C_4$ fluoroalkyl, and $R^J$ is absent.

18. A compound of Formula VII having the structure:

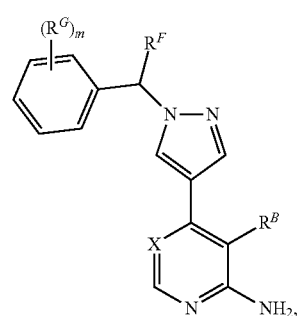

VII or a salt, including a pharmaceutically acceptable salt, or a prodrug thereof;

wherein X is =N— or a carbon atom that is substituted or unsubstituted;

$R^B$ is substituted phenyl or $C_5$-$C_6$ heteroaryl (Ar, or HetAr), either of which is unsubstituted or substituted by up to three $R^E$ independently of one another;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$ alkyl, —$S(O)C_1$-$C_4$ alkyl, —$SO_2C_1$-$C_4$ alkyl, —$NH_2$, —$NHC_1$-$C_4$ alkyl, —$N(C_1$-$C_4$ alkyl$)_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl$)_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$ alkyl, —$SO_2C_1$-$C_4$ alkyl, —$N(C_1$-$C_4$ alkyl$)_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —$NH_2$, —$NMe_2$, —$CONH_2$, —CONHMe, —$CONMe_2$, —COOH, —$CH_3$ and —$CF_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —$S(O)C_1$-$C_4$alkyl, —$SO_2C_1$-$C_4$alkyl, —$NH_2$, —$NHC_1$-$C_4$ alkyl, —$N(C_1$-$C_4$ alkyl$)_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl$)_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$alkyl, —$SO_2C_1$-$C_4$alkyl, —$N(C_1$-$C_4$ alkyl$)_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

subscript m is 1, 2 or 3;

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —$OC_1$-$C_4$ fluoroalkyl, $C_1$-$C_{20}$ alkyl, $C_3$-$C_6$ cycloalkyl, $C_1$-$C_4$ fluoroalkyl, and halogen;

wherein the remaining aromatic carbon atom(s) of the pyrimidine or pyridine ring of formula VII is unsubstituted or independently substituted by $R^J$; and wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —S(O)$C_1$-$C_4$alkyl, —$SO_2C_1$-$C_4$alkyl, —$NH_2$, —$NHC_1$-$C_4$ alkyl, —$N(C_1$-$C_4$ alkyl$)_2$, and —CN, or is selected from the group consisting of $C_1$-$C_4$ alkyl, $C_1$-$C_4$ fluoroalkyl, $C_1$-$C_4$ alkoxy, halogen, —CN, —$NH_2$, and —OH.

In certain embodiments of Formula VII, $R^B$ is substituted aryl.

In preferred embodiments of Formula VII, X is =N— or =CH—, $R^B$ is substituted phenyl, $R^F$ is replaced by —H or is —$CH_2NH_2$, subscript m is 1, $R^G$ is absent or is —$C_1$ or —$CF_3$, and $R^H$ and $R^J$ are absent.

19. A compound of Formula VIII having the structure:

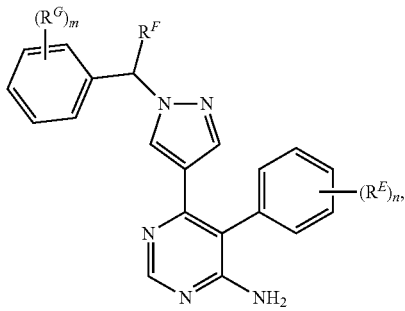

VIII or a salt, including a pharmaceutically acceptable salt, or a prodrug thereof;

wherein each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$ alkyl, —S(O)$C_1$-$C_4$ alkyl, —$SO_2C_1$-$C_4$ alkyl, —$NH_2$, —$NHC_1$-$C_4$ alkyl, —$N(C_1$-$C_4$ alkyl$)_2$, —$NO_2$, —CN, —OCN, —COOH, —COO($C_1$-$C_4$ alkyl), —$CONH_2$, —CONH($C_1$-$C_4$ alkyl), —CON($C_1$-$C_4$ alkyl$)_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$ alkyl, —$SO_2C_1$-$C_4$alkyl, —$N(C_1$-$C_4$ alkyl$)_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

subscript n is 1, 2 or 3;

each $R^F$, if present, is independently selected from the group consisting of halogen, —OH, —CN, —$NH_2$, —$NMe_2$, —$CONH_2$, —CONHMe, —$CONMe_2$, —COOH, —$CH_3$ and —$CF_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —S(O)$C_1$-$C_4$alkyl, —$SO_2C_1$-$C_4$alkyl, —$NH_2$, —$NHC_1$-$C_4$ alkyl, —$N(C_1$-$C_4$ alkyl$)_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl$)_2$, —NHCO($C_1$-$C_4$ alkyl), —NHCONH($C_1$-$C_4$ alkyl), —$NHCONH_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —$SC_1$-$C_4$alkyl, —$SO_2C_1$-$C_4$alkyl, —$N(C_1$-$C_4$ alkyl$)_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

subscript m is 1, 2 or 3;

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —$OC_1$-$C_4$ fluoroalkyl, $C_1$-$C_{20}$ alkyl, $C_3$-$C_6$ cycloalkyl, $C_1$-$C_4$ fluoroalkyl, and halogen;

wherein the remaining aromatic carbon atom(s) of the pyrimidine ring of formula VIII is unsubstituted or independently substituted by $R^J$; and wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —$SC_1$-$C_4$alkyl, —S(O)$C_1$-$C_4$alkyl, —$SO_2C_1$-$C_4$alkyl, —$NH_2$, —$NHC_1$-$C_4$ alkyl, —$N(C_1$-$C_4$ alkyl$)_2$, and —CN, or is selected from the group consisting of $C_1$-$C_4$ alkyl, $C_1$-$C_4$ fluoroalkyl, $C_1$-$C_4$ alkoxy, halogen, —CN, —$NH_2$, and —OH.

In preferred embodiments of Formula VIII, subscript n is 1 or 2, $R^E$ are independently halogen or —$OCH_3$, $R^F$ is replaced by —H or is —$CH_2NH_2$, subscript m is 1, $R^G$ is absent or is —$C_1$ or —$CF_3$; and $R^H$ and $R^J$ are absent.

20. A compound of Formula IX having the structure:

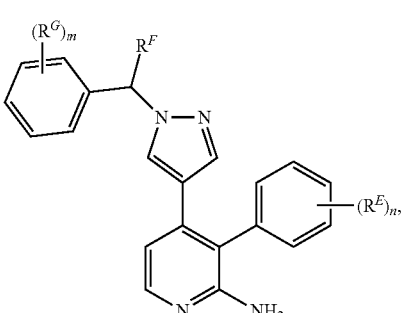

IX or a salt, including a pharmaceutically acceptable salt, or a prodrug thereof;

wherein each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$ alkyl, —S(O)$C_1$-$C_4$ alkyl, —SO$_2$$C_1$-$C_4$ alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$ alkyl, —SO$_2$$C_1$-$C_4$ alkyl, —N($C_1$-$C_4$ alkyl)$_2$, —CN. In certain embodiments at least two adjacent $R^E$ are present that taken together define a substituted or unsubstituted $C_5$-$C_6$ carbocycle or heterocycle, and the remaining $R^E$, if present, is as previously defined;

subscript n is 1, 2 or 3;

each $R^F$, if present, is independently selected from the group consisting of halogen, —OH, —CN, —NH$_2$, —NMe$_2$, —CONH$_2$, —CONHMe, —CONMe$_2$, —COOH, —CH$_3$ and —CF$_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, —NO$_2$, —CN, —OCN, —COOH, —COO($C_1$-$C_4$ alkyl), —CONH$_2$, —CONH($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCONH$_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —SO$_2$$C_1$-$C_4$alkyl, —N($C_1$-$C_4$ alkyl)$_2$, —CN. In certain embodiments at least two adjacent $R^G$ are present that taken together define a substituted or unsubstituted $C_5$-$C_6$ carbocycle or heterocycle, and the remaining $R^G$, if present, is as previously defined;

subscript m is 1, 2 or 3;

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;

wherein the remaining aromatic carbon atom(s) of the pyridine ring of formula IX is unsubstituted or independently substituted by $R^J$; and wherein each $R^J$, if present, is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —SO$_2$$C_1$-$C_4$alkyl, —NH$_2$, —NH$C_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —NH$_2$, and —OH;

each $R^H$ if present, is selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen.

In preferred embodiments of Formula X, subscript n is 1, $R^E$ is —Cl, $R^F$ is replaced by —H, subscript m is 1, $R^G$ is —CF$_3$, and $R^H$ and $R^1$ are absent.

21. A composition comprising, essentially consisting of or consisting of one or more compounds, or salt(s) thereof, preferably one, two or three, of Formula I-IX, and at least one excipient.

In preferred embodiments the composition comprises, consists essentially of, or consists of a compound of Formula I-IX and at least one excipient.

In more preferred embodiments the compositions is a pharmaceutically acceptable formulation comprising, consisting essentially of, or consisting of one and only one compound of Formula I-IX and at least one pharmaceutically acceptable excipient.

In some preferred embodiments the compositions is a pharmaceutically acceptable formulation comprising, consisting essentially of, or consisting of one compound of Formula I and at least one pharmaceutically acceptable excipient.

22. A compound of Formula I-IX or a pharmaceutically acceptable salt or prodrug thereof, wherein the activity of the compound to S6K is between about 100 μM and about 1 pM or less (but greater than 0).

23. The compound of embodiment 22 wherein the compound is a selective S6K inhibitor.

24. A compound of Formula I-IX or a pharmaceutically acceptable salt or prodrug thereof, wherein the compound is a selective S6K inhibitor.

25. The compound of any one of embodiments 22, 23 or 24 wherein the compound or pharmaceutically acceptable salt thereof is a selective S6K inhibitor wherein the activity (i.e., IC$_{50}$) of the S6K inhibitor compound is between about 10 μM and 1 pM or less (but greater than 0).

26. The compound of any one of embodiments 21-25 wherein the compound is 6-(1-Benzyl-1H-pyrazol-4-yl)-5-(p-chlorophenyl)-4-pyrimidinylamine, 5-(p-Chlorophenyl)-6-(1-methyl-1H-pyrazol-4-yl)-4-pyrimidinylamine, 5-(p-Chlorophenyl)-6-(1-{1-[m-(trifluoromethyl)phenyl]ethyl}-1H-pyrazol-4-yl)-4-pyrimidinylamine, 5-(p-Chlorophenyl)-6-(1-{[p-(trifluoromethyl)phenyl]methyl}-1H-pyrazol-4-yl)-4-pyrimidinylamine, (R,S)-2-{4-[6-Amino-5-(p-chlorophenyl)-4-pyrimidinyl]-1H-pyrazol-1-yl}-2-phenylethanol, (R,S)-6-[1-(2-Amino-1-phenylethyl)-1H-pyrazol-4-yl]-5-(p-chlorophenyl)-4-pyrimidinamine, 5-(p-Chlorophenyl)-6-[1-(1-phenylethenyl)-1H-pyrazol-4-yl]-4-pyrimidinylamine, (R,S)-{4-[6-Amino-5-(p-chlorophenyl)-4-pyrimidinyl]-1H-pyrazol-1-yl}phenylacetamide, (R,S)—N,N-Dimethyl{4-[6-amino-5-(p-chlorophenyl)-4-pyrimidinyl]-1H-pyrazol-1-yl}phenylacetamide, 5-(p-Chlorophenyl)-6-(1-phenyl-1H-pyrazol-4-yl)-4-pyrimidinylamine, 5-(p-Chlorophenyl)-6-[1-(o-tolyl)-1H-pyrazol-4-yl]-4-pyrimidinylamine, 5-(p-Chlorophenyl)-6-[1-(m-chlorophenyl)-1H-pyrazol-4-yl]-4-pyrimidinylamine, 5-(p-Chlorophenyl)-6-{1-[m-(trifluoromethyl)phenyl]-1H-pyrazol-4-yl}-4-pyrimidinylamine, 5-(p-Chlorophenyl)-6-[1-(tetrahydro-2H-pyran-2-yl)-1H-pyrazol-4-yl]-4-pyrimidinylamine, 5-(p-Chlorophenyl)-6-{1-[(m-fluorophenyl)methyl]-1H-pyrazol-4-yl}-4-pyrimidinylamine, 5-(p-Chlorophenyl)-6-{1-[(p-chlorophenyl)methyl]-1H-pyrazol-4-yl}-4-pyrimidinylamine, 5-(p-Chlorophenyl)-6-(1-{[o-(trifluoromethyl)phenyl]methyl}-1H-pyrazol-4-yl)-4- pyrimidinylamine, 5-(p-Chlorophenyl)-6-{1-[(p-fluorophenyl)methyl]-1H-pyrazol-4-yl}-4-pyrimidinylamine, 5-(p-Chlorophenyl)-6-{1-[(2,4-difluorophenyl)methyl]-1H-pyrazol-4-yl}-4-pyrimidinylamine, 5-(p-Chlorophenyl)-6-{1-[(p-trifluoromethoxyphenyl)methyl]-1H-pyrazol-4-yl}-4-pyrimidinylamine, 5-(p-Chlorophenyl)-6-{1-[(o-fluorophenyl)methyl]-1H-pyrazol-4-yl}-4-pyrimidinylamine, {1-[6-Amino-5-(p-chlorophenyl)-4-pyrimidinyl]-1H-pyrazol-4-yl}phenylmethanone, 6-(4-Benzyl-1H-pyrazol-1-yl)-5-(p-chlorophenyl)-4-pyrimidinylamine, 5-(p-Methoxyphenyl)-6-(1-{[p-(trifluoromethyl)phenyl]methyl}-1H-pyrazol-4-yl)-4-pyrimidinylamine, 5-(p-Fluorophenyl)-6-(1-{[p-(trifluoromethyl)phenyl]methyl}-1H-pyrazol-4-yl)-4-pyrimidinylamine, 5-[p-(Methylsulfonyl)phenyl]-6-(1-{[p-(trifluoromethyl)phenyl]methyl}-1H-pyrazol-4-yl)-4-pyrimidinylamine, 5-(4-Chloro-3-fluorophenyl)-6-(1-{[p-(trifluoromethyl)phenyl]methyl}-1H-pyrazol-4-yl)-4-pyrimidinylamine, 5-(3,4-Dichlorophenyl)-6-(1-{[p-(trifluoromethyl)phenyl]methyl}-1H-pyrazol-4-yl)-4-pyrimidinylamine, 5-(4-Chloro-3-methoxyphenyl)-6-(1-{[p-(trifluoromethyl)phenyl]methyl}-1H-pyrazol-4-yl)-4-pyrimidinylamine, 5-(3-Chloro-4-methoxyphenyl)-6-(1-{[p-(trifluoromethyl)phenyl]methyl}-1H-pyrazol-4-yl)-4-pyrimidinylamine, 5-(3,4-Difluorophenyl)-6-(1-{[p-(trifluoromethyl)phenyl]methyl}-1H-pyrazol-4-yl)-4-pyrimidinylamine, 5-(3-Fluoro-4-methoxyphenyl)-6-(1-{[p-(trifluoromethyl)phenyl]methyl}-1H-pyrazol-4-yl)-4-pyrimidinylamine, 5-(4-Fluoro-3-methoxyphenyl)-6-(1-{[p-(trifluoromethyl)phenyl]methyl}-1H-pyrazol-4-yl)-4-pyrimidinylamine, 5-(p-Trifluoromethoxyphenyl)-6-(1-{[p-(trifluoromethyl)phenyl]methyl}-1H-pyrazol-4-yl)-4-pyrimidinylamine, 5-(2,2-Difluoro-2H-1,3-benzodioxol-5-yl)-6-(1-{[p-(trifluoromethyl)phenyl]methyl}-1H-pyrazol-4-yl)-4-pyrimidinylamine, 4-(1-{[p-(Trifluoromethyl)phenyl]methyl}-1H-pyrazol-4-yl)-2-pyridylamine, 5-Chloro-4-(1-{[p-(trifluoromethyl)phenyl]methyl}-1H-pyrazol-4-yl)-2-pyridylamine, 3-(p-Methoxyphenyl)-4-(1-{[p-(trifluoromethyl)phenyl]methyl}-1H-pyrazol-4-yl)-2-pyridylamine, 3-(p-Chlorophenyl)-4-(1-{[p-(trifluoromethyl)phenyl]methyl}-1H-pyrazol-4-yl)-2-pyridylamine, 5-(4-Chloro-3-fluorophenyl)-6-(1-{[p-(trifluoromethyl)phenyl]methyl}-1H-pyrazol-4-yl)-4-pyrimidinylamine, 5-(3-Fluoro-4-methoxyphenyl)-6-(1-{[p-(trifluoromethyl)phenyl]methyl}-1H-pyrazol-4-yl)-4-pyrimidinylamine, 5-(1H-Pyrazol-4-yl)-6-(1-{[p-(trifluoromethyl)phenyl]methyl}-1H-pyrazol-4-yl)-4-pyrimidinylamine, or a salt thereof.

27. The compound of any one of embodiments 21-25 where the compound is 6-(1-Benzyl-3-methyl-1H-pyrazol-4-yl)-5-(p-chlorophenyl)-4-pyrimidinylamine, 5-(p-Chlorophenyl)-6-(3-methyl-1-{[p-(trifluoromethyl)phenyl]methyl}-1H-pyrazol-4-yl)-4-pyrimidinylamine, 6-[1-(2-Amino-1-phenylethyl)-3-methyl-1H-pyrazol-4-yl]-5-(p-chlorophenyl)-4-pyrimidinamine, 6-(1-{2-Amino-1-[p-(trifluoromethyl)phenyl]ethyl}-3-methyl-1H-pyrazol-4-yl)-5-(p-chlorophenyl)-4-pyrimidinamine, 4-(1-Benzyl-3-methyl-1H-pyrazol-4-yl)-3-(p-chlorophenyl)-2-pyridylamine, 3-(p-Chlorophenyl)-4-(3-methyl-1-{[p-(trifluoromethyl)phenyl]methyl}-1H-pyrazol-4-yl)-2-pyridylamine, 4-[1-(2-Amino-1-phenylethyl)-3-methyl-1H-pyrazol-4-yl]-3-(p-chlorophenyl)-2-pyridinamine, 4-(1-{2-Amino-1-[p-(trifluoromethyl)phenyl]ethyl}-3-methyl-1H-pyrazol-4-yl)-3-(p-chlorophenyl)-2-pyridinamine, 6-(1-Benzyl-3,5-dimethyl-1H-pyrazol-4-yl)-5-(p-chlorophenyl)-4-pyrimidinylamine, 5-(p-Chlorophenyl)-6-(3,5-dimethyl-1-{[p-(trifluoromethyl)phenyl]methyl}-1H-pyrazol-4-yl)-4-pyrimidinylamine, 6-[1-(2-Amino-1-phenylethyl)-3,5-dimethyl-1H-pyrazol-4-yl]-5-(p-chlorophenyl)-4-pyrimidinamine, 6-(1-{2-Amino-1-[p-(trifluoromethyl)phenyl]ethyl}-3,5-dimethyl-1H-pyrazol-4-yl)-5-(p-chlorophenyl)-4-pyrimidinamine, 4-(1-Benzyl-3,5-dimethyl-1H-pyrazol-4-yl)-3-(p-chlorophenyl)-2-pyridylamine, 3-(p-Chlorophenyl)-4-(3,5-dimethyl-1-{[p-(trifluoromethyl)phenyl]methyl}-1H-pyrazol-4-yl)-2-pyridylamine, 4-[1-(2-Amino-1-phenylethyl)-3,5-dimethyl-1H-pyrazol-4-yl]-3-(p-chlorophenyl)-2-pyridinamine, 4-(1-{2-Amino-1-[p-(trifluoromethyl)phenyl]ethyl}-3,5-dimethyl-1H-pyrazol-4-yl)-3-(p-chlorophenyl)-2-pyridinamine, {4-[6-Amino-5-(p-chlorophenyl)-4-pyrimidinyl]-1-benzyl-1H-pyrazol-3-yl}methanol, {4-[6-Amino-5-(p-chlorophenyl)-4-pyrimidinyl]-1-{[p-(trifluoromethyl)phenyl]methyl}-1H-pyrazol-3-yl}methanol, {4-[6-Amino-5-(p-chlorophenyl)-4-pyrimidinyl]-1-(2-amino-1-phenylethyl)-1H-pyrazol-3-yl}methanol, {4-[6-Amino-5-(p-chlorophenyl)-4-pyrimidinyl]-1-{2-amino-1-[p-(trifluoromethyl)phenyl]ethyl}-1H-pyrazol-3-yl}methanol, {4-[2-Amino-3-(p-chlorophenyl)-4-pyridyl]-1-benzyl-1H-pyrazol-3-yl}methanol, {4-[2-Amino-3-(p-chlorophenyl)-4-pyridyl]-1-{[p-(trifluoromethyl)phenyl]methyl}-1H-pyrazol-3-yl}methanol, {4-[2-Amino-3-(p-chlorophenyl)-4-pyridyl]-1-(2-amino-1-phenylethyl)-1H-pyrazol-3-yl}methanol, {4-[2-Amino-3-(p-chlorophenyl)-4-pyridyl]-1-{2-amino-1-[p-(trifluoromethyl)phenyl]ethyl}-1H-pyrazol-3-yl}methanol, 6-(1-Benzyl-3-fluoro-1H-pyrazol-4-yl)-5-(p-chlorophenyl)-4-pyrimidinylamine, 5-(p-Chlorophenyl)-6-(3-fluoro-1-{[p-(trifluoromethyl)phenyl]methyl}-1H-pyrazol-4-yl)-4-pyrimidinylamine, 6-[1-(2-Amino-1-phenylethyl)-3-fluoro-1H-pyrazol-4-yl]-5-(p-chlorophenyl)-4-pyrimidinamine, 6-(1-{2-Amino-1-[p-(trifluoromethyl)phenyl]ethyl}-3-fluoro-1H-pyrazol-4-yl)-5-(p-chlorophenyl)-4-pyrimidinamine, 4-(1-Benzyl-3-fluoro-1H-pyrazol-4-yl)-3-(p-chlorophenyl)-2-pyridylamine, 3-(p-Chlorophenyl)-4-(3-fluoro-1-{[p-(trifluoromethyl)phenyl]methyl}-1H-pyrazol-4-yl)-2-pyridylamine, 4-[1-(2-Amino-1-phenylethyl)-3-fluoro-1H-pyrazol-4-yl]-3-(p-chlorophenyl)-2-pyridinamine, 4-(1-{2-Amino-1-[p-(trifluoromethyl)phenyl]ethyl}-3-fluoro-1H-pyrazol-4-yl)-3-(p-chlorophenyl)-2-pyridinamine, 6-[1-Benzyl-3-(trifluoromethyl)-1H-pyrazol-4-yl]-5-(p-chlorophenyl)-4-pyrimidinylamine, 5-(p-Chlorophenyl)-6-[3-(trifluoromethyl)-1-{[p-(trifluoromethyl)phenyl]methyl}-1H-pyrazol-4-yl]-4-pyrimidinylamine, 6-[1-(2-Amino-1-phenylethyl)-3-(trifluoromethyl)-1H-pyrazol-4-yl]-5-(p-chlorophenyl)-4-pyrimidinamine, 6-(1-{2-Amino-1-[p-(trifluoromethyl)phenyl]ethyl}-3-(trifluoromethyl)-1H-pyrazol-4-yl)-5-(p-chlorophenyl)-4-pyrimidinamine, 4-[1-Benzyl-3-(trifluoromethyl)-1H-pyrazol-4-yl]-3-(p-chlorophenyl)-2-pyridylamine, 3-(p-Chlorophenyl)-4-[3-(trifluoromethyl)-1-{[p-(trifluoromethyl)phenyl]methyl}-1H-pyrazol-4-yl]-2-pyridylamine, 4-[1-(2-Amino-1-phenylethyl)-3-(trifluoromethyl)-1H-pyrazol-4-yl]-3-(p-chlorophenyl)-2-pyridinamine, 4-(1-{2-Amino-1 I-[p-(trifluoromethyl)phenyl]ethyl}-3-(trifluoromethyl)-1H-pyrazol-4-yl)-3-(p-chlorophenyl)-2-pyridinamine, or a salt thereof.

28. The compound of any one of embodiments 21-25 where the compound is (2S)-2-{4-[6-Amino-5-(p-chlorophenyl)-4-pyrimidinyl]-1H-pyrazol-1-yl}-2-phenylethanol, (2R)-2-{4-[6-Amino-5-(p-chlorophenyl)-4-pyrimidinyl]-1H-pyrazol-1-yl}-2-phenylethanol, (2S)-2-{4-[6-Amino-5-(p-chlorophenyl)-4-pyrimidinyl]-1H-pyrazol-1-yl}-2-[p-(trifluoromethyl)phenyl]ethanol, (2R)-2-{4-[6-Amino-5-(p-chlorophenyl)-4-pyrimidinyl]-1H-pyrazol-1-yl}-2-[p-(trifluoromethyl)phenyl]ethanol, (2S)-2-{4-[6-Amino-5-(p-chlorophenyl)-4-pyrimidinyl]-1H-pyrazol-1-yl}-2-phenylethanamine, (2R)-2-{4-[6-Amino-5-(p-chlorophenyl)-4-pyrimidinyl]-1H-pyrazol-1-yl}-2-phenylethanamine, (2S)-2-{4-[6-Amino-5-(p-chlorophenyl)-4-pyrimidinyl]-1H-pyrazol-1-yl}-2-[p-(trifluoromethyl)phenyl]ethanamine, (2R)-2-{4-[6-Amino-5-(p-chlorophenyl)-4-pyrimidinyl]-1H-pyrazol-1-yl}-2-[p-(trifluoromethyl)phenyl]ethanamine, (2S)-2-{4-[6-Amino-5-(p-chlorophenyl)-4-pyrimidinyl]-1H-pyrazol-1-yl}-1-(dimethylamino)-2-phenylethane, (2R)-2-{4-[6-Amino-5-(p-chlorophenyl)-4-pyrimidinyl]-1H-pyrazol-1-yl}-1-(dimethylamino)-2-phenylethane, (2S)-2-{4-[6-Amino-5-(p-chlorophenyl)-4-pyrimidinyl]-1H-pyrazol-1-yl}-1-(dimethylamino)-2-[p-(trifluoromethyl)phenyl]ethane, (2R)-2-{4-[6-Amino-5-(p-chlorophenyl)-4-pyrimidinyl]-1H-pyrazol-1-yl}-1-(dimethylamino)-2-[p-(trifluoromethyl)phenyl]ethane, (2S)-2-{4-[6-Amino-5-(1H-pyrazol-4-yl)-4-pyrimidinyl]-1H-pyrazol-1-yl}-1-(dimethylamino)-2-[p-(trifluoromethyl)phenyl]ethane, (R)-2-{4-[6-Amino-5-(1H-pyrazol-4-yl)-4-pyrimidinyl]-1H-pyrazol-1-yl}-1-(dimethylamino)-2-[p-(trifluoromethyl)phenyl]ethane, (2S)-{4-[6-Amino-5-(p-chlorophenyl)-4-pyrimidinyl]-1H-pyrazol-1-yl}[p-(trifluoromethyl)phenyl]acetic acid, (2R)-{4-[6-Amino-5-(p-chlorophenyl)-4-pyrimidinyl]-1H-pyrazol-1-yl}[p-(trifluoromethyl)phenyl]acetic acid, (2S)-{4-[6-Amino-5-(p-chlorophenyl)-4-pyrimidinyl]-1H-pyrazol-1-yl}[p-(trifluoromethyl)phenyl]acetamide, (2R)-{4-[6-Amino-5-(p-chlorophenyl)-4-pyrimidinyl]-1H-pyrazol-1-yl}[p-(trifluoromethyl)phenyl]acetamide, 3-(1H-Pyrazol-4-yl)-4-(1-{[p-(trifluoromethyl)phenyl]methyl}-1H-pyrazol-4-yl)-2-pyridylamine, (S)-2-{4-[2-Amino-3-(p-chlorophenyl)-4-pyridyl]-1H-pyrazol-1-yl}-2-[p-(trifluoromethyl)phenyl]ethanol, (R)-2-{4-[2-Amino-3-(p-chlorophenyl)-4-pyridyl]-1H-pyrazol-1-yl}-2-[p-(trifluoromethyl)phenyl]ethanol, 4-(1-{(S)-2-Amino-1-[p-(trifluoromethyl)phenyl]ethyl}-1H-pyrazol-4-yl)-3-(p-chlorophenyl)-2-pyridinamine, 4-(1-{(R)-2-Amino-1-[p-(trifluoromethyl)phenyl]ethyl}-1H-pyrazol-4-yl)-3-(p-chlorophenyl)-2-pyridinamine, 4-(1-{(S)-2-(Dimethylamino)-1-[p-(trifluoromethyl)phenyl]ethyl}-1H-pyrazol-4-yl)-3-(p-chlorophenyl)-2-pyridinamine, 4-(1-{(R)-2-(Dimethylamino)-1-[p-(trifluoromethyl)phenyl]ethyl}-1H-pyrazol-4-yl)-3-(p-chlorophenyl)-2-pyridinamine, (S)-{4-[2-Amino-3-(p-chlorophenyl)-4-pyridyl]-1H-pyrazol-1-yl}[p-(trifluoromethyl)phenyl]acetic acid, (R)-{4-[2-Amino-3-(p-chlorophenyl)-4-pyridyl]-1H-pyrazol-1-yl}[p-(trifluoromethyl)phenyl]acetic acid, (S)-{4-[2-Amino-3-(p-chlorophenyl)-4-pyridyl]-1H-pyrazol-1-yl}[p-(trifluoromethyl)phenyl]acetamide, (R)-{4-[2-Amino-3-(p-chlorophenyl)-4-pyridyl]-1H-pyrazol-1-yl}[p-(trifluoromethyl)phenyl]acetamide, or a salt thereof.

29. A pharmaceutically acceptable formulation comprising, consisting essentially of, or consisting of a compound of Table 1 or a pharmaceutically acceptable salt thereof, and at least one pharmaceutically acceptable excipient.

30. A method comprising administering an effective amount of a Formula I-IX compound having a S6K-dependent or S6K-mediated disease or condition.

31. The method of embodiment 30 wherein the compound is selected from Table 1, or a salt thereof.

32. A method comprising administering an effective amount of a Formula I-IX compound, or a pharmaceutically acceptable salt thereof, to a subject having a S6K-mediated disease or condition wherein the compound is that of embodiment 31.

33. The method of any one of embodiments 30-32 wherein the S6K-dependent or S6K-mediated disease or condition is a cancer.

34. The method of embodiment 33 wherein the cancer is ovarian cancer, breast cancer or triple negative breast cancer.

35. The method of any one of embodiments 30-32 wherein the S6K-dependent or S6K-mediated disease or condition is a fibrotic disease, including idiopathic fibrosis (IPF) or non-alcoholic steatohepatitis (NASH).

36. The method of any one of embodiment 30-32 wherein the S6K-dependent or S6K-mediated disease or condition is selected from the group consisting of diabetes and diabetic complications.

37. The method of any one of embodiments 30-32 wherein the S6K-dependent or S6K-mediated disease or condition is an autism spectrum disorder.

38. The method of any one of embodiments 30-32 wherein the S6K-dependent or S6K-mediated disease or condition is Fragile X syndrome.

39. The method of any one of embodiments 30-38 wherein the subject is a human.

40. Use of a compound of any one of embodiments 1-28, or a pharmaceutically acceptable salt thereof, in preparation of a medicament for treating a S6K-dependent disease or condition.

41. A medicament for treating a subject in need thereof with a S6K-dependent disease or condition, the medicament comprising a compound of any one of claims 1-28, or a pharmaceutically acceptable salt thereof.

The compounds of Table 1 are exemplary of the invention but not limiting, wherein compounds 47-116 are prepared according to the appropriately modified procedures of the examples for preparation of compounds 1-47.

TABLE 1

| Example | Compound name |
|---|---|
| 1 | 6-(1-Benzyl-1H-pyrazol-4-yl)-5-(p-chlorophenyl)-4-pyrimidinylamine |
| 2 | 5-(p-Chlorophenyl)-6-(1-methyl-1H-pyrazol-4-yl)-4-pyrimidinylamine |
| 3 | 5-(p-Chlorophenyl)-6-(1-{1-[m-(trifluoromethyl)phenyl]ethyl}-1H-pyrazol-4-yl)-4-pyrimidinylamine |

TABLE 1-continued

| Example | Compound name |
|---|---|
| 4 | 5-(p-Chlorophenyl)-6-(1-{[p-(trifluoromethyl)phenyl]methyl}-1H-pyrazol-4-yl)-4-pyrimidinylamine |
| 5 | (R,S)-2-{4-[6-Amino-5-(p-chlorophenyl)-4-pyrimidinyl]-1H-pyrazol-1-yl}-2-phenylethanol |
| 6 | (R,S)-6-[1-(2-Amino-1-phenylethyl)-1H-pyrazol-4-yl]-5-(p-chlorophenyl)-4-pyrimidinamine |
| 7 | 5-(p-Chlorophenyl)-6-[1-(1-phenylethenyl)-1H-pyrazol-4-yl]-4-pyrimidinylamine |
| 8 | (R,S)-{4-[6-Amino-5-(p-chlorophenyl)-4-pyrimidinyl]-1H-pyrazol-1-yl}phenylacetamide |
| 9 | (R,S)-N,N-Dimethyl{4-[6-amino-5-(p-chlorophenyl)-4-pyrimidinyl]-1H-pyrazol-1-yl}phenylacetamide |
| 10 | 5-(p-Chlorophenyl)-6-(1-phenyl-1H-pyrazol-4-yl)-4-pyrimidinylamine |
| 11 | 5-(p-Chlorophenyl)-6-[1-(o-tolyl)-1H-pyrazol-4-yl]-4-pyrimidinylamine |
| 12 | 5-(p-Chlorophenyl)-6-[1-(m-chlorophenyl)-1H-pyrazol-4-yl]-4-pyrimidinylamine |
| 13 | 5-(p-Chlorophenyl)-6-{1-[m-(trifluoromethyl)phenyl]-1H-pyrazol-4-yl}-4-pyrimidinylamine |
| 14 | 5-(p-Chlorophenyl)-6-[1-(tetrahydro-2H-pyran-2-yl)-1H-pyrazol-4-yl]-4-pyrimidinylamine |
| 15 | 5-(p-Chlorophenyl)-6-{1-[(m-fluorophenyl)methyl]-1H-pyrazol-4-yl}-4-pyrimidinylamine |
| 16 | 5-(p-Chlorophenyl)-6-{1-[(p-chlorophenyl)methyl]-1H-pyrazol-4-yl}-4-pyrimidinylamine |
| 17 | 5-(p-Chlorophenyl)-6-(1-{[o-(trifluoromethyl)phenyl]methyl}-1H-pyrazol-4-yl)-4-pyrimidinylamine |
| 18 | 5-(p-Chlorophenyl)-6-{1-[(p-fluorophenyl)methyl]-1H-pyrazol-4-yl}-4-pyrimidinylamine |
| 19 | 5-(p-Chlorophenyl)-6-{1-[(2,4-difluorophenyl)methyl]-1H-pyrazol-4-yl}-4-pyrimidinylamine |
| 20 | 5-(p-Chlorophenyl)-6-{1-[(p-trifluoromethoxyphenyl)methyl]-1H-pyrazol-4-yl}-4-pyrimidinylamine |
| 21 | 5-(p-Chlorophenyl)-6-{1-[(o-fluorophenyl)methyl]-1H-pyrazol-4-yl}-4-pyrimidinylamine |
| 22 | {1-[6-Amino-5-(p-chlorophenyl)-4-pyrimidinyl]-1H-pyrazol-4-yl}phenylmethanone |
| 23 | 6-(4-Benzyl-1H-pyrazol-1-yl)-5-(p-chlorophenyl)-4-pyrimidinylamine |
| 24 | 5-(p-Methoxyphenyl)-6-(1-{[p-(trifluoromethyl)phenyl]methyl}-1H-pyrazol-4-yl)-4-pyrimidinylamine |
| 25 | 5-(p-Fluorophenyl)-6-(1-{[p-(trifluoromethyl)phenyl]methyl}-1H-pyrazol-4-yl)-4-pyrimidinylamine |
| 26 | 5-[p-(Methylsulfonyl)phenyl]-6-(1-{[p-(trifluoromethyl)phenyl]methyl}-1H-pyrazol-4-yl)-4-pyrimidinylamine |
| 27 | 5-(4-Chloro-3-fluorophenyl)-6-(1-{[p-(trifluoromethyl)phenyl]methyl}-1H-pyrazol-4-yl)-4-pyrimidinylamine |
| 28 | 5-(3,4-Dichlorophenyl)-6-(1-{[p-(trifluoromethyl)phenyl]methyl}-1H-pyrazol-4-yl)-4-pyrimidinylamine |
| 29 | 5-(4-Chloro-3-methoxyphenyl)-6-(1-{[p-(trifluoromethyl)phenyl]methyl}-1H-pyrazol-4-yl)-4-pyrimidinylamine |
| 30 | 5-(3-Chloro-4-methoxyphenyl)-6-(1-{[p-(trifluoromethyl)phenyl]methyl}-1H-pyrazol-4-yl)-4-pyrimidinylamine |
| 31 | 5-(3,4-Difluorophenyl)-6-(1-{[p-(trifluoromethyl)phenyl]methyl}-1H-pyrazol-4-yl)-4-pyrimidinylamine |
| 32 | 5-(3-Fluoro-4-methoxyphenyl)-6-(1-{[p-(trifluoromethyl)phenyl]methyl}-1H-pyrazol-4-yl)-4-pyrimidinylamine |
| 33 | 5-(4-Fluoro-3-methoxyphenyl)-6-(1-{[p-(trifluoromethyl)phenyl]methyl}-1H-pyrazol-4-yl)-4-pyrimidinylamine |
| 34 | 5-(p-Trifluoromethoxyphenyl)-6-(1-{[p-(trifluoromethyl)phenyl]methyl}-1H-pyrazol-4-yl)-4-pyrimidinylamine |
| 35 | 5-(2,2-Difluoro-2H-1,3-benzodioxol-5-yl)-6-(1-{[p-(trifluoromethyl)phenyl]methyl}-1H-pyrazol-4-yl)-4-pyrimidinylamine |
| 36 | 4-(1-{[p-(Trifluoromethyl)phenyl]methyl}-1H-pyrazol-4-yl)-2-pyridylamine |
| 37 | 5-Chloro-4-(1-{[p-(trifluoromethyl)phenyl]methyl}-1H-pyrazol-4-yl)-2-pyridylamine |
| 38 | 3-(p-Methoxyphenyl)-4-(1-{[p-(trifluoromethyl)phenyl]methyl}-1H-pyrazol-4-yl)-2-pyridylamine |
| 39 | 3-(p-Chlorophenyl)-4-(1-{[p-(trifluoromethyl)phenyl]methyl}-1H-pyrazol-4-yl)-2-pyridylamine |
| 40 | 5-(4-Chloro-3-fluorophenyl)-6-(1-{[p-(trifluoromethyl)phenyl]methyl}-1H-pyrazol-4-yl)-4-pyrimidinylamine |
| 41 | 5-(3-Fluoro-4-methoxyphenyl)-6-(1-{[p-(trifluoromethyl)phenyl]methyl}-1H-pyrazol-4-yl)-4-pyrimidinylamine |
| 42 | 5-(1H-Pyrazol-4-yl)-6-(1-{[p-(trifluoromethyl)phenyl]methyl}-1H-pyrazol-4-yl)-4-pyrimidinylamine |
| 43 | N-[5-(p-Chlorophenyl)-6-(1-{[p-(trifluoromethyl)phenyl]methyl}-1H-pyrazol-4-yl)-4-pyrimidinyl]acetamide (43) |
| 44 | N-Acetyl-N-[5-(p-chlorophenyl)-6-(1-{[p-(trifluoromethyl)phenyl]methyl}-1H-pyrazol-4-yl)-4-pyrimidinyl]acetamide |
| 45 | (Methylsulfonyl)[5-(p-chlorophenyl)-6-(1-{[p-(trifluoromethyl)phenyl]methyl}-1H-pyrazol-4-yl)-4-pyrimidinyl]amine |
| 46 | N,N-Dimethyl[5-(p-chlorophenyl)-6-(1-{[p-(trifluoromethyl)phenyl]methyl}-1H-pyrazol-4-yl)-4-pyrimidinyl]amine |
| 47 | N-Methyl[5-(p-chlorophenyl)-6-(1-{[p-(trifluoromethyl)phenyl]methyl}-1H-pyrazol-4-yl)-4-pyrimidinyl]amine |
| 48 | 6-(1-Benzyl-3-methyl-1H-pyrazol-4-yl)-5-(p-chlorophenyl)-4-pyrimidinylamine |
| 49 | 5-(p-Chlorophenyl)-6-(3-methyl-1-{[p-(trifluoromethyl)phenyl]methyl}-1H-pyrazol-4-yl)-4-pyrimidinylamine |
| 50 | 6-[1-(2-Amino-1-phenylethyl)-3-methyl-1H-pyrazol-4-yl]-5-(p-chlorophenyl)-4-pyrimidinamine |

TABLE 1-continued

| Example | Compound name |
|---|---|
| 51 | 6-(1-{2-Amino-1-[p-(trifluoromethyl)phenyl]ethyl}-3-methyl-1H-pyrazol-4-yl)-5-(p-chlorophenyl)-4-pyrimidinamine |
| 52 | 4-(1-Benzyl-3-methyl-1H-pyrazol-4-yl)-3-(p-chlorophenyl)-2-pyridylamine |
| 53 | 3-(p-Chlorophenyl)-4-(3-methyl-1-{[p-(trifluoromethyl)phenyl]methyl}-1H-pyrazol-4-yl)-2-pyridylamine |
| 54 | 4-[1-(2-Amino-1-phenylethyl)-3-methyl-1H-pyrazol-4-yl]-3-(p-chlorophenyl)-2-pyridinamine |
| 55 | 4-(1-{2-Amino-1-[p-(trifluoromethyl)phenyl]ethyl}-3-methyl-1H-pyrazol-4-yl)-3-(p-chlorophenyl)-2-pyridinamine |
| 56 | 6-(1-Benzyl-3,5-dimethyl-1H-pyrazol-4-yl)-5-(p-chlorophenyl)-4-pyrimidinylamine |
| 57 | 5-(p-Chlorophenyl)-6-(3,5-dimethyl-1-{[p-(trifluoromethyl)phenyl]methyl}-1H-pyrazol-4-yl)-4-pyrimidinylamine |
| 58 | 6-[1-(2-Amino-1-phenylethyl)-3,5-dimethyl-1H-pyrazol-4-yl]-5-(p-chlorophenyl)-4-pyrimidinamine |
| 59 | 6-(1-{2-Amino-1-[p-(trifluoromethyl)phenyl]ethyl}-3,5-dimethyl-1H-pyrazol-4-yl)-5-(p-chlorophenyl)-4-pyrimidinamine |
| 60 | 4-(1-Benzyl-3,5-dimethyl-1H-pyrazol-4-yl)-3-(p-chlorophenyl)-2-pyridylamine |
| 61 | 3-(p-Chlorophenyl)-4-(3,5-dimethyl-1-{[p-(trifluoromethyl)phenyl]methyl}-1H-pyrazol-4-yl)-2-pyridylamine |
| 62 | 4-[1-(2-Amino-1-phenylethyl)-3,5-dimethyl-1H-pyrazol-4-yl]-3-(p-chlorophenyl)-2-pyridinamine |
| 63 | 4-(1-{2-Amino-1-[p-(trifluoromethyl)phenyl]ethyl}-3,5-dimethyl-1H-pyrazol-4-yl)-3-(p-chlorophenyl)-2-pyridinamine |
| 64 | {4-[6-Amino-5-(p-chlorophenyl)-4-pyrimidinyl]-1-benzyl-1H-pyrazol-3-yl}methanol |
| 65 | {4-[6-Amino-5-(p-chlorophenyl)-4-pyrimidinyl]-1-{[p-(trifluoromethyl)phenyl]methyl}-1H-pyrazol-3-yl}methanol |
| 66 | {4-[6-Amino-5-(p-chlorophenyl)-4-pyrimidinyl]-1-(2-amino-1-phenylethyl)-1H-pyrazol-3-yl}methanol |
| 67 | {4-[6-Amino-5-(p-chlorophenyl)-4-pyrimidinyl]-1-{2-amino-1-[p-(trifluoromethyl)phenyl]ethyl}-1H-pyrazol-3-yl}methanol |
| 68 | {4-[2-Amino-3-(p-chlorophenyl)-4-pyridyl]-1-benzyl-1H-pyrazol-3-yl}methanol |
| 69 | {4-[2-Amino-3-(p-chlorophenyl)-4-pyridyl]-1-{[p-(trifluoromethyl)phenyl]methyl}-1H-pyrazol-3-yl}methanol |
| 70 | {4-[2-Amino-3-(p-chlorophenyl)-4-pyridyl]-1-(2-amino-1-phenylethyl)-1H-pyrazol-3-yl}methanol |
| 71 | {4-[2-Amino-3-(p-chlorophenyl)-4-pyridyl]-1-{2-amino-1-[p-(trifluoromethyl)phenyl]ethyl}-1H-pyrazol-3-yl}methanol |
| 72 | 6-(1-Benzyl-3-fluoro-1H-pyrazol-4-yl)-5-(p-chlorophenyl)-4-pyrimidinylamine |
| 73 | 5-(p-Chlorophenyl)-6-(3-fluoro-1-{[p-(trifluoromethyl)phenyl]methyl}-1H-pyrazol-4-yl)-4-pyrimidinylamine |
| 74 | 6-[1-(2-Amino-1-phenylethyl)-3-fluoro-1H-pyrazol-4-yl]-5-(p-chlorophenyl)-4-pyrimidinamine |
| 75 | 6-(1-{2-Amino-1-[p-(trifluoromethyl)phenyl]ethyl}-3-fluoro-1H-pyrazol-4-yl)-5-(p-chlorophenyl)-4-pyrimidinamine |
| 76 | 4-(1-Benzyl-3-fluoro-1H-pyrazol-4-yl)-3-(p-chlorophenyl)-2-pyridylamine |
| 77 | 3-(p-Chlorophenyl)-4-(3-fluoro-1-{[p-(trifluoromethyl)phenyl]methyl}-1H-pyrazol-4-yl)-2-pyridylamine |
| 78 | 4-[1-(2-Amino-1-phenylethyl)-3-fluoro-1H-pyrazol-4-yl]-3-(p-chlorophenyl)-2-pyridinamine |
| 79 | 4-(1-{2-Amino-1-[p-(trifluoromethyl)phenyl]ethyl}-3-fluoro-1H-pyrazol-4-yl)-3-(p-chlorophenyl)-2-pyridinamine |
| 80 | 6-[1-Benzyl-3-(trifluoromethyl)-1H-pyrazol-4-yl]-5-(p-chlorophenyl)-4-pyrimidinylamine |
| 81 | 5-(p-Chlorophenyl)-6-[3-(trifluoromethyl)-1-{[p-(trifluoromethyl)phenyl]methyl}-1H-pyrazol-4-yl]-4-pyrimidinylamine |
| 82 | 6-[1-(2-Amino-1-phenylethyl)-3-(trifluoromethyl)-1H-pyrazol-4-yl]-5-(p-chlorophenyl)-4-pyrimidinamine |
| 83 | 6-(1-{2-Amino-1-[p-(trifluoromethyl)phenyl]ethyl}-3-(trifluoromethyl)-1H-pyrazol-4-yl)-5-(p-chlorophenyl)-4-pyrimidinamine |
| 84 | 4-[1-Benzyl-3-(trifluoromethyl)-1H-pyrazol-4-yl]-3-(p-chlorophenyl)-2-pyridylamine |
| 85 | 3-(p-Chlorophenyl)-4-[3-(trifluoromethyl)-1-{[p-(trifluoromethyl)phenyl]methyl}-1H-pyrazol-4-yl]-2-pyridylamine |
| 86 | 4-[1-(2-Amino-1-phenylethyl)-3-(trifluoromethyl)-1H-pyrazol-4-yl]-3-(p-chlorophenyl)-2-pyridinamine |
| 87 | 4-(1-{2-Amino-1-[p-(trifluoromethyl)phenyl]ethyl}-3-(trifluoromethyl)-1H-pyrazol-4-yl)-3-(p-chlorophenyl)-2-pyridinamine |
| 88 | (2S)-2-{4-[6-Amino-5-(p-chlorophenyl)-4-pyrimidinyl]-1H-pyrazol-1-yl}-2-phenylethanol |
| 89 | (2R)-2-{4-[6-Amino-5-(p-chlorophenyl)-4-pyrimidinyl]-1H-pyrazol-1-yl}-2-phenylethanol |
| 90 | (2S)-2-{4-[6-Amino-5-(p-chlorophenyl)-4-pyrimidinyl]-1H-pyrazol-1-yl}-2-[p-(trifluoromethyl)phenyl]ethanol |
| 91 | (2R)-2-{4-[6-Amino-5-(p-chlorophenyl)-4-pyrimidinyl]-1H-pyrazol-1-yl}-2-[p-(trifluoromethyl)phenyl]ethanol |
| 92 | (2S)-2-{4-[6-Amino-5-(p-chlorophenyl)-4-pyrimidinyl]-1H-pyrazol-1-yl}-2-phenylethanamine |
| 93 | (2R)-2-{4-[6-Amino-5-(p-chlorophenyl)-4-pyrimidinyl]-1H-pyrazol-1-yl}-2-phenylethanamine |
| 94 | (2S)-2-{4-[6-Amino-5-(p-chlorophenyl)-4-pyrimidinyl]-1H-pyrazol-1-yl}-2-[p-(trifluoromethyl)phenyl]ethanamine |

TABLE 1-continued

| Example | Compound name |
|---|---|
| 95 | (2R)-2-{4-[6-Amino-5-(p-chlorophenyl)-4-pyrimidinyl]-1H-pyrazol-1-yl}-2-[p-(trifluoromethyl)phenyl]ethanamine |
| 96 | (2S)-2-{4-[6-Amino-5-(p-chlorophenyl)-4-pyrimidinyl]-1H-pyrazol-1-yl}-1-(dimethylamino)-2-phenylethane |
| 97 | (2R)-2-{4-[6-Amino-5-(p-chlorophenyl)-4-pyrimidinyl]-1H-pyrazol-1-yl}-1-(dimethylamino)-2-phenylethane |
| 98 | (2S)-2-{4-[6-Amino-5-(p-chlorophenyl)-4-pyrimidinyl]-1H-pyrazol-1-yl}-1-(dimethylamino)-2-[p-(trifluoromethyl)phenyl]ethane |
| 99 | (2R)-2-{4-[6-Amino-5-(p-chlorophenyl)-4-pyrimidinyl]-1H-pyrazol-1-yl}-1-(dimethylamino)-2-[p-(trifluoromethyl)phenyl]ethane |
| 100 | (2S)-2-{4-[6-Amino-5-(1H-pyrazol-4-yl)-4-pyrimidinyl]-1H-pyrazol-1-yl}-1-(dimethylamino)-2-[p-(trifluoromethyl)phenyl]ethane |
| 101 | (R)-2-{4-[6-Amino-5-(1H-pyrazol-4-yl)-4-pyrimidinyl]-1H-pyrazol-1-yl}-1-(dimethylamino)-2-[p-(trifluoromethyl)phenyl]ethane |
| 102 | (2S)-{4-[6-Amino-5-(p-chlorophenyl)-4-pyrimidinyl]-1H-pyrazol-1-yl}[p-(trifluoromethyl)phenyl]acetic acid |
| 103 | (2R)-{4-[6-Amino-5-(p-chlorophenyl)-4-pyrimidinyl]-1H-pyrazol-1-yl}[p-(trifluoromethyl)phenyl]acetic acid |
| 104 | (2S)-{4-[6-Amino-5-(p-chlorophenyl)-4-pyrimidinyl]-1H-pyrazol-1-yl}[p-(trifluoromethyl)phenyl]acetamide |
| 105 | (2R)-{4-[6-Amino-5-(p-chlorophenyl)-4-pyrimidinyl]-1H-pyrazol-1-yl}[p-(trifluoromethyl)phenyl]acetamide |
| 106 | 3-(1H-Pyrazol-4-yl)-4-(1-{[p-(trifluoromethyl)phenyl]methyl}-1H-pyrazol-4-yl)-2-pyridylamine |
| 107 | (S)-2-{4-[2-Amino-3-(p-chlorophenyl)-4-pyridyl]-1H-pyrazol-1-yl}-2-[p-(trifluoromethyl)phenyl]ethanol |
| 108 | (R)-2-{4-[2-Amino-3-(p-chlorophenyl)-4-pyridyl]-1H-pyrazol-1-yl}-2-[p-(trifluoromethyl)phenyl]ethanol |
| 109 | 4-(1-{(S)-2-Amino-1-[p-(trifluoromethyl)phenyl]ethyl}-1H-pyrazol-4-yl)-3-(p-chlorophenyl)-2-pyridinamine |
| 110 | 4-(1-{(R)-2-Amino-1-[p-(trifluoromethyl)phenyl]ethyl}-1H-pyrazol-4-yl)-3-(p-chlorophenyl)-2-pyridinamine |
| 111 | 4-(1-{(S)-2-(Dimethylamino)-1-[p-(trifluoromethyl)phenyl]ethyl}-1H-pyrazol-4-yl)-3-(p-chlorophenyl)-2-pyridinamine |
| 112 | 4-(1-{(R)-2-(Dimethylamino)-1-[p-(trifluoromethyl)phenyl]ethyl}-1H-pyrazol-4-yl)-3-(p-chlorophenyl)-2-pyridinamine |
| 113 | (S)-{4-[2-Amino-3-(p-chlorophenyl)-4-pyridyl]-1H-pyrazol-1-yl}[p-(trifluoromethyl)phenyl]acetic acid |
| 114 | (R)-{4-[2-Amino-3-(p-chlorophenyl)-4-pyridyl]-1H-pyrazol-1-yl}[p-(trifluoromethyl)phenyl]acetic acid |
| 115 | (S)-{4-[2-Amino-3-(p-chlorophenyl)-4-pyridyl]-1H-pyrazol-1-yl}[p-(trifluoromethyl)phenyl]acetamide |
| 116 | (R)-{4-[2-Amino-3-(p-chlorophenyl)-4-pyridyl]-1H-pyrazol-1-yl}[p-(trifluoromethyl)phenyl]acetamide |

Compound 42-116 are predicted to have that activity based upon structure activity relationships for compounds 1-42 which are or have been tested for S6K inhibition activity and metabolism considerations. That is, compounds that do not have or have insufficient S6K inhibitory activity for one or more aspects of the invention acquire that activity when acted upon by metabolic processes in vivo. Those processes include a combination or one or more Phase I metabolic processes such as oxidation by one or more flavin mono-oxidase, cytochrome P40 enzymes, reduction or oxidation by one or more oxidoreductase enzymes or nonspecific hydrolysis or hydrolytic processes mediated by one or more esterase, protease or lipase enzymes, or Phase II metabolic processes such as glucuronidation or sulfation or a combination of Phase I and Phase II processes.

EXAMPLES

HPLC Methods

HPLC traces for examples synthesized were recorded using a HPLC consisting of Shimadzu or Agilent HPLC pumps, degasser and UV detector, equipped with an Agilent 1100 series auto-sampler. A MS detector (APCI) PE Sciex API 150 EX was incorporated for purposes of recording mass spectral data. HPLC/mass traces were obtained using one of two chromatographic methods:

Method 1: Column SunFire™ (Waters) C18, size 2.1 mm×50 mm;
Solvent A: 0.05% TFA in water, Solvent B: 0.05% TFA in acetonitrile;
Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Method 2: Column Aquasil™ (Thermo) C18, size 2.1 mm×50 mm; particle size 5μ. Solvent A: 0.05% TFA in water, Solvent B: 0.05% TFA in acetonitrile;
Flow rate—0.3 mL/min; Gradient: 10% B to 95% B in 2.4 min, hold at 95% B for 6.25 min and 95% B to 10% B in 0.2 min, hold at 10% B for 1.5 min.; UV detector—channel 1=220 nm, channel 2=254 nm.

Example 1. 6-(1-Benzyl-1H-pyrazol-4-yl)-5-(p-chlorophenyl)-4-pyrimidinylamine (1)

Step 1: Dimethyl (p-chlorophenyl)malonate

Dimethyl carbonate (45.00 g, 500 mmol) was dissolved in THF (100 mL) under stirring and an inert atmosphere of $N_2$, and treated portionwise with NaH (8.00 g of a 60% dispersion in oil, 200 mmol). The resulting suspension was stirred at room temperature for 1 hour. Methyl (p-chlorophenyl)

acetate (18.46 g, 100 mmol) dissolved in THF (80 mL) was added to the mixture via a dropping funnel over 30 minutes. The resulting mixture was then heated to reflux for 2.5 hours. The reaction was cooled to room temperature and carefully quenched by dropwise addition of saturated $NH_4Cl$ aqueous solution (50 mL), followed by addition of water (200 mL). The product was extracted with EtOAc (2×300 mL). The combined organic layer was washed with brine, dried over anhydrous $MgSO_4$, filtered and concentrated in vacuo. The crude product was obtained as a yellow oil, which was used in the next step without further purification. Yield=24.26 g (100 mmol, quantitative).

Step 2: 5-(p-Chlorophenyl)-4,6-pyrimidinediol

A round bottom flask equipped with magnetic stirring, a dropping funnel and inert atmosphere inlet was charged with NaOMe (65 mL of a 30% w/v solution in MeOH, 350 mmol) and cooled to 0° C. A solution of dimethyl (p-chlorophenyl) malonate (example 1, step 1, 24.26 g, 100 mmol) in MeOH (500 mL) was added slowly over 30 minutes. The reaction mixture was then allowed to reach room temperature over 2 hours, after which time formamidine acetate (13.60 g, 130 mmol) was added portionwise. The reaction mixture was stirred overnight at rt and all solvents were removed in vacuo. The remaining solids were suspended in $H_2O$ (100 mL) and cooled to 0° C. Mixture was treated with 2 M HCl aqueous solution (300 mL). The resulting suspension was treated with sufficient 2 N NaOH aqueous solution to bring the solution's pH to ~4. The precipitates were filtered, rinsed with $H_2O$ and air-dried. The product was obtained as an off-white solid. Yield=16.90 g (76 mmol, 76%). HPLC/MS (ESI) m/z 222.9-225.4 ($M^+ + H^+$). Method 1 retention time=0.4 min.

Step 3: 4,6-Dichloro-5-(p-chlorophenyl)pyrimidine 5-(p-Chlorophenyl)-4,6-pyrimidinediol (example 1, step 2, 16.80 g, 75.7 mmol) was treated with $POCl_3$ (84.7 mL, 908.4 mmol) followed by careful addition of N,N-dimethylaniline (21.1 mL, 171.1 mmol). The resulting mixture was heated to 130° C. for 3 hours, cooled to rt and then slowly poured onto ice/water with stirring. After all ice melted, the solids were removed by filtration, rinsed with $H_2O$ and air-dried. The product was obtained as a tan solid. Yield=17.34 g (67 mmol, 89%). HPLC/MS (ESI) m/z 258.8, 261.0, 263.2 ($M^+ + H^+$). Method 1 retention time=3.20 min.

Step 4: 6-Chloro-5-(p-chlorophenyl)-4-pyrimidinylamine

A mixture containing 4,6-dichloro-5-(p-chlorophenyl)pyrimidine (example 1, step 3, 17.20 g, 66.7 mmol) in 1,4-dioxane (140 mL) and aqueous $NH_4OH$ (70 mL) was heated to 80° C. for 4 hours in a pressure vessel. LCMS indicated reaction completed. Reaction cooled to rt, then transferred to a separatory funnel. The product was extracted with EtOAc (3×150 mL) and the combined organic layers was washed with $H_2O$ and brine, dried over anhydrous $MgSO_4$, filtered and evaporated. The crude product was crystallized in boiling EtOH (155 mL), which afforded the pure product as white crystals upon cooling. Yield=12.69 g (53.4 mmol, 79%). HPLC/MS (ESI) m/z 240.0, 242.0, 243.9 ($M^+ + H^+$). Method 1 retention time=2.62 min.

Step 5: 6-(1-Benzyl-1H-pyrazol-4-yl)-5-(p-chlorophenyl)-4-pyrimidinylamine (1)

6-Chloro-5-(p-chlorophenyl)-4-pyrimidinylamine (example 1, step 4, 50 mg, 0.21 mmol) and (1-benzyl-1H-pyrazol-4-yl)boronic acid (64 mg, 0.32 mmol) were dissolved in a 2:1 v/v mixture of toluene/EtOH (2.1 mL) and treated with 2M $Na_2CO_3$ aqueous solution (0.7 mL). The resulting mixture was degassed under $N_2$ for 10 minutes. $Pd[Ph_3P]_4$ (12 mg, 0.011 mmol) was added and the resulting mixture was stirred at 90° C. for 16 hours. After cooling, the reaction was transferred to a separatory funnel, extracted with EtOAc (50 mL) and washed with $H_2O$ and brine. The organic layer was separated, dried over anhydrous $MgSO_4$, filtered and evaporated. The crude residue was purified by silica gel chromatography, eluting with a hexanes/EtOAc gradient. The product was obtained as a white solid. Yield=17 mg (0.047 mmol, 22%). HPLC/MS (ESI) m/z 362.4 ($M^+ + H^+$). Method 1 retention time=2.55 min.

Example 2. 5-(p-Chlorophenyl)-6-(1-methyl-1H-pyrazol-4-yl)-4-pyrimidinylamine (2)

This compound was prepared according to the method reported for example 1, step 5 using the following reagents: 6-chloro-5-(p-chlorophenyl)-4-pyrimidinylamine (example 1, step 4, 24 mg, 0.1 mmol), 1-methyl-1H-pyrazole-4-boronic acid pinacol ester (20 mg, 0.15 mmol), 1,4-dioxane (0.5 mL), water (0.03 mL), $K_3PO_4$ (64 mg, 0.3 mmol), $Pd[Ph_3P]_4$ (5 mg, 0.004 mmol). Purification by preparative TLC plate on silica-gel (20×20 cm), eluting with acetone/$CH_2Cl_2$ (3:7 v/v). Product is a white solid. Yield=10 mg (0.035 mmol, 35%). HPLC/MS (ESI) m/z 286.3 ($M^+ + H^+$). Method 1 retention time=1.88 min.

Example 3. (±)-5-(p-Chlorophenyl)-6-(1-{1-[m-(trifluoromethyl)phenyl]ethyl}-1H-pyrazol-4-yl)-4-pyrimidinylamine (3)

Step 1: (±)-4-Bromo-1-{1-[m-(trifluoromethyl)phenyl]ethyl}-1H-pyrazole

A stirring mixture of 4-bromo-1H-pyrazole (639 mg, 4.35 mmol), DMF (10 mL) and $Cs_2CO_3$ (1.42 g, 4.35 mmol) was treated with m-(1-bromoethyl)-(trifluoromethyl)-benzene (1.00 g, 3.95 mmol). The reaction was stirred at room temperature for 48 hours. The reaction was treated with $H_2O$ (100 mL) and the product was extracted with EtOAc (100 mL). The organic layer was washed with $H_2O$, 1M HCl aqueous and brine, dried over anhydrous $MgSO_4$, filtered and evaporated. The product was obtained as a colorless oil. Yield=1.31 g (4.11 mmol, quantitative). HPLC/MS (ESI) m/z 319.1 ($M^+ + H^+$). Method 1 retention time=3.29 min.

Step 2: (±)-4,4,5,5-Tetramethyl-2-(1-{1-[m-(trifluoromethyl)phenyl]ethyl}-1H-pyrazol-4-yl)-1,3,2-dioxaborolane A mixture of (±)-4-bromo-1-{1-[m-(trifluoromethyl)phenyl]ethyl}-1H-pyrazole (1.31 g, 4.11 mmol), bis(pinacolato)diboron (1.58 g, 6.18 mmol), KOAc (1.22 g, 12.4 mmol) and 1,4-dioxane (11 mL) was degassed under $N_2$ for 10 minutes at room temperature. $Pd(dppf)Cl_2 \cdot CH_2Cl_2$ (337 mg, 0.41 mmol) was added and the mixture was heated to 90° C. for 16 hours. The reaction was cooled to room temperature, filtered through a pad of CELITE and rinsed with EtOAc. The filtrates were washed with $H_2O$, 0.1M HCl aqueous and brine, dried over anhydrous $MgSO_4$, filtered and evaporated. The residue was purified by silica-gel chromatography eluting with a hexanes/EtOAc gradient. The pure product was obtained as a colorless oil. Yield=450 mg (1.23 mmol, 30%). HPLC/MS (ESI) m/z 367.2 (M$^+$+H$^+$). Method 1 retention time=3.17 min.

Step 3: (±)-5-(p-Chlorophenyl)-6-(1-{1-[m-(trifluoromethyl)phenyl]ethyl}-1H-pyrazol-4-yl)-4-pyrimidinylamine (3)

This compound was prepared according to the method reported for example 1, step 5 using the following reagents: 6-chloro-5-(p-chlorophenyl)-4-pyrimidinylamine (example 1, step 4, 91 mg, 0.38 mmol), (±)-4,4,5,5-tetramethyl-2-(1-{1-[m-(trifluoromethyl)phenyl]ethyl}-1H-pyrazol-4-yl)-1,3,2-dioxaborolane (example 3, step 2, 210 mg, 0.57 mmol), 2:1 v/v mixture of toluene/EtOH (15 mL), 2M Na$_2$CO$_3$ aqueous solution (5 mL) and Pd[Ph$_3$P]$_4$ (22 mg, 0.019 mmol). Purification by silica-gel chromatography eluting with a hexanes/EtOAc gradient gave the pure product as a white solid. Yield=83 mg (0.19 mmol, 49%). HPLC/MS (ESI) m/z 444.5 (M$^+$+H$^+$). Method 1 retention time=2.70 min.

Example 4. 5-(p-Chlorophenyl)-6-(1-{[p-(trifluoromethyl)phenyl]methyl}-1H-pyrazol-4-yl)-4-pyrimidinylamine (4)

Step 1: 4-Bromo-1-{[p-(trifluoromethyl)phenyl]methyl}-1H-pyrazole

This compound was prepared according to the method reported for example 3, step 1 using the following reagents: 4-bromo-1H-pyrazole (1.47 g, 10.0 mmol), DMF (20 mL), Cs$_2$CO$_3$ (3.26 g, 10.0 mmol) and 4-(trifluoromethyl)-benzyl bromide (2.18 g, 9.1 mmol). Purification by silica-gel chromatography eluting with a hexanes/EtOAc gradient gave the pure product as a white solid. Yield=1.89 g (6.2 mmol, 68%). HPLC/MS (ESI) m/z 305.2 (M$^+$+H$^+$). Method 1 retention time=3.11 min.

Step 2: 4,4,5,5-Tetramethyl-2-(1-{[p-(trifluoromethyl)phenyl]methyl}-1H-pyrazol-4-yl)-1,3,2-dioxaborolane This compound was prepared according to the method reported for example 3, step 2 using the following reagents: 4-bromo-1-{[p-(trifluoromethyl)phenyl]methyl}-1H-pyrazole (1.73 g, 5.70 mmol), bis(pinacolato)diboron (2.20 g, 8.55 mmol), KOAc (1.68 g, 17.10 mmol), 1,4-dioxane (15 mL) and Pd(dppf)Cl$_2$·CH$_2$Cl$_2$ (466 mg, 0.57 mmol). Purification by silica-gel chromatography eluting with a hexanes/EtOAc gradient gave the pure product as a white solid. Yield=497 mg (1.41 mmol, 25%). HPLC/MS (ESI) m/z 353.4 (M$^+$+H$^+$). Method 1 retention time=3.07 min.

Step 3: 5-(p-Chlorophenyl)-6-(1-{[p-(trifluoromethyl)phenyl]methyl}-1H-pyrazol-4-yl)-4-pyrimidinylamine (4)

This compound was prepared according to the method reported for example 1, step 5 using the following reagents: 6-chloro-5-(p-chlorophenyl)-4-pyrimidinylamine (example 1, step 4, 91 mg, 0.38 mmol), 4,4,5,5-tetramethyl-2-(1-{[p-(trifluoromethyl)phenyl]methyl}-1H-pyrazol-4-yl)-1,3,2-dioxaborolane (example 4, step 2, 203 mg, 0.57 mmol), 2:1 v/v mixture of toluene/EtOH (15 mL), 2M Na$_2$CO$_3$ aqueous solution (5 mL) and Pd[Ph$_3$P]$_4$ (22 mg, 0.019 mmol). Purification by silica-gel chromatography eluting with a CH$_2$Cl$_2$/EtOAc gradient gave the pure product as a white solid. Yield=58 mg (0.14 mmol, 36%). HPLC/MS (ESI) m/z 430.1 (M$^+$+H$^+$). Method 1 retention time=2.66 min.

Example 5. (±)-2-{4-[6-Amino-5-(p-chlorophenyl)-4-pyrimidinyl]-1H-pyrazol-1-yl}-2-phenylethanol (5)

Step 1: (±)-2-(4-Bromo-1H-pyrazol-1-yl)-2-phenylethanol

A mixture of styrene oxide (12.9 g, 10.7 mmol), 4-bromo-1H-pyrazole (15.7 g, 10.7 mmol) and Y(NO$_3$)$_3$·6H$_2$O (0.102 g, 0.268 mmol) was stirred for 20 hours at 23° C. The crude product was purified by silica-gel column chromatography, eluting with hexanes/EtOAc mixture, from 5% to 30% of EtOAc, to provide the title compound as a colorless oil (2.46 g, 9.21 mmol, 86%). HPLC/MS (ESI) m/z 269.1 (M$^+$+H$^+$). Method 1 retention time=2.71 min.

Step 2: (±)-2-Phenyl-2-[4-(4,4,5,5-tetramethyl-1,3,2-dioxaborolan-2-yl)-1H-pyrazol-1-yl]ethanol This compound was prepared according to the method reported for example 3, step 2 using the following reagents: (±)-2-(4-bromo-1H-pyrazol-1-yl)-2-phenylethanol (example 5, step 1, 0.534 g, 2.00 mmol), bis(pinacolato)diboron (1.52 g, 6.00 mmol), KOAc (0.589 g, 6.00 mmol), 1,4-dioxane (10 mL) and Pd(dppf)Cl$_2$·CH$_2$Cl$_2$ (0.163 g, 0.200 mmol). Purification by silica-gel chromatography eluting with a hexanes/EtOAc gradient gave the pure product as a light yellow oil. Yield=0.441 g (1.40 mmol, 70%). HPLC/MS (ESI) m/z 315.5 (M$^+$+H$^+$). Method 1 retention time=2.56 min.

Step 3: (±)-2-{4-[6-Amino-5-(p-chlorophenyl)-4-pyrimidinyl]-1H-pyrazol-1-yl}-2-phenylethanol (5)

This compound was prepared according to the method reported for example 1, step 5 using the following reagents: 6-chloro-5-(p-chlorophenyl)-4-pyrimidinylamine (example 1, step 4, 0.288 g, 1.20 mmol), (±)-2-phenyl-2-[4-(4,4,5,5-tetramethyl-1,3,2-dioxaborolan-2-yl)-1H-pyrazol-1-yl]ethanol (example 5, step 2, 0.441 g, 1.40 mmol), 1,4-dioxane (3.5 mL), 2M Na$_2$CO$_3$ aqueous solution (3.60 mmol, 1.80 mL) and Pd[Ph$_3$P]$_4$ (0.138 g, 0.120 mmol). Purification by reverse phase column chromatography (C-18, CH$_3$CN:H$_2$O, 25% to 90% of CH$_3$CN, modified with TFA) gradient gave the pure product as a colorless oil. Yield=0.397 g (1.01 mmol, 72%). HPLC/MS (ESI) m/z 392.3 (M$^+$+H$^+$). Method 1 retention time=2.45 min.

Example 6. (±)-6-[1-(2-Amino-1-phenylethyl)-1H-pyrazol-4-yl]-5-(p-chlorophenyl)-4-pyrimidinamine (6)

Step 1: (±)-5-(p-Chlorophenyl)-6-{1-[2-(methylsulfonyloxy)-1-phenylethyl]-1H-pyrazol-4-yl}-4-pyrimidinylamine A solution of (±)-2-{4-[6-amino-5-(p-chlorophenyl)-4-pyrimidinyl]-1H-pyrazol-1-yl}-2-phenylethanol (example 5, 100 mg, 0.25 mmol) in CH$_2$Cl$_2$ (2.5 mL) was treated with Et$_3$N (38 mg, 0.37 mmol) under N$_2$ and this mixture was cooled to 0° C. with an ice/water bath. A solution of methanesulfonyl chloride (39 mg, 0.34 mmol) in CH$_2$Cl$_2$ (1 mL) was added dropwise and the resulting mixture was stirred for 2 hours and then warmed to room temperature and stirred for an additional 2 hours. The reaction was quenched with H$_2$O and the product was extracted with CH$_2$Cl$_2$. The organics were dried over anhydrous MgSO$_4$, filtered and evaporated. The crude product was obtained as a white semi-solid and was used in the next step without further purification. Yield=123 mg (0.26 mmol, ~quant.).

Step 2: (±)-6-[1-(2-Azido-1-phenylethyl)-1H-pyrazol-4-yl]-5-(p-chlorophenyl)-4-pyrimidinylamine A mixture containing (±)-5-(p-chlorophenyl)-6-{1-[2-(methylsulfonyloxy)-1-phenylethyl]-1H-pyrazol-4-yl}-4-pyrimidinylamine (example 6, step 1, 77 mg, 0.163 mmol), NaN$_3$ (32 mg, 0.489 mmol) and DMF (3 mL) was stirred at room temperature for 1 hour and then heated to 80° C. for 5 hours. After cooling to room temperature, the reaction was quenched with H$_2$O and the product was extracted with CH$_2$Cl$_2$. The organics were dried over anhydrous MgSO$_4$, filtered and evaporated. The crude product was obtained as a yellow semi-solid and was used in the next step without further purification. Yield=64 mg (0.154 mmol, 94%).

Step 3: (±)-6-[1-(2-Amino-1-phenylethyl)-1H-pyrazol-4-yl]-5-(p-chlorophenyl)-4-pyrimidinamine (6)

A solution of (±)-6-[1-(2-azido-1-phenylethyl)-1H-pyrazol-4-yl]-5-(p-chlorophenyl)-4-pyrimidinylamine (example 6, step 2, 64 mg, 0.154 mmol) in THF (2 mL) was treated with Ph$_3$P (81 mg, 0.307 mmol) and the resulting mixture was stirred at room temperature for 3 hours under N$_2$. H$_2$O (0.4 mL) was added and the mixture was stirred for an additional 24 hours. The reaction mixture was purified directly by reverse phase column chromatography (C-18, CH$_3$CN:H$_2$O, 15% to 75% of CH$_3$CN, modified with TFA) gradient gave the pure product as a colorless oil. Yield=12 mg (0.03 mmol, 19%). HPLC/MS (ESI) m/z 391.1 (M$^+$+H$^+$). Method 1 retention time=2.30 min.

Example 7. 5-(p-Chlorophenyl)-6-[1-(1-phenylethenyl)-1H-pyrazol-4-yl]-4-pyrimidinylamine (7)

A mixture containing (±)-5-(p-chlorophenyl)-6-{1-[2-(methylsulfonyloxy)-1-phenylethyl]-1H-pyrazol-4-yl}-4-pyrimidinylamine (example 6, step 1, 46 mg, 0.1 mmol), dimethylamine hydrochloride (10 mg, 0.125 mmol) and K$_2$CO$_3$ (35 mg, 0.250 mml) in DMF (2.5 mL) was stirred at 80° C. for 2 hours under a N$_2$ atmosphere. The reaction mixture was then cooled to room temperature and stirred for 16 hours. The reaction mixture was purified directly by reverse phase column chromatography (C-18, CH$_3$CN:H$_2$O, 15% to 75% of CH$_3$CN, modified with TFA) gradient gave the pure product as a white solid. Yield=15 mg (0.04 mmol, 40%). HPLC/MS (ESI) m/z 374.1 (M$^+$+H$^+$). Method 1 retention time=2.69 min.

Example 8. (±)-{4-[6-Amino-5-(p-chlorophenyl)-4-pyrimidinyl]-1H-pyrazol-1-yl}phenylacetamide (8)

Step 1: (±)-Ethyl (4-bromo-1H-pyrazol-1-yl)phenylacetate

A solution containing 4-bromo-1H-pyrazole (1.62 g, 11.0 mmol), (±)-ethyl chlorophenylacetate (1.72 mL, 10.0 mmol) in DMF (20 mL) was treated with Cs$_2$CO$_3$ (3.58 g, 11.0 mmol) and the resulting mixture was stirred at room temperature for 2 hours. The reaction was diluted with H$_2$O (100 mL) and the product was extracted with EtOAc (100 mL). The organic layer was washed with 1 N aqueous HCl solution and brine, dried over anhydrous MgSO$_4$, filtered and evaporated. The crude product was purified by silica-gel column chromatography, eluting with hexanes/EtOAc mixture to provide the title compound as a white solid (2.46 g, 7.96 mmol, 80%).

Step 2: (±)-(4-Bromo-1H-pyrazol-1-yl)phenylacetic acid (±)-Ethyl (4-bromo-1H-pyrazol-1-yl)phenylacetate (example 8, step 1, 400 mg, 1.29 mmol) was dissolved in THF (6.5 mL) and treated with a 1M aqueous LiOH solution (6.5 mL). The resulting mixture was stirred at room temperature for 3 hours. The reaction was quenched with 1N aqueous HCl solution and the product was extracted with EtOAc. The organics were dried over anhydrous MgSO$_4$, filtered and evaporated. The product was obtained as a white solid. Yield=362 mg (1.29 mmol, quantitative).

Step 3: (±)-(4-Bromo-1H-pyrazol-1-yl)phenylacetamide

A solution containing (±)-(4-bromo-1H-pyrazol-1-yl)phenylacetic acid (example 8, step 2, 169 mg, 0.6 mmol) and diisopropylethylamine (430 mL, 2.4 mmol) in DMF (3 mL) was treated with NH$_4$Cl (64 mg, 1.2 mmol) and HATU (297 mg, 0.78 mmol). The resulting mixture was stirred at room temperature overnight. Next morning, the reaction was diluted with EtOAc, washed with H$_2$O, saturated NaHCO$_3$ aqueous and brine. The organics were dried over anhydrous MgSO$_4$, filtered and evaporated. The crude material was triturated with CH$_2$Cl$_2$. The product was obtained as a white solid. Yield=146 mg (0.52 mmol, 87%).

Step 4: (±)-Phenyl[4-(4,4,5,5-tetramethyl-1,3,2-dioxaborolan-2-yl)-1H-pyrazol-1-yl]acetamide This compound was prepared according to the method reported for example 3, step 2 using the following reagents: (±)-(4-bromo-1H-pyrazol-1-yl)phenylacetamide (example 8, step 3, 146 mg, 0.52 mmol), bis(pinacolato)diboron (330 mg, 1.30 mmol), KOAc (115 mg, 1.17 mmol), 1,4-dioxane (5.2 mL) and Pd(dppf)Cl$_2$ (20 mg, 0.026 mmol). Purification by silica-gel chromatography eluting with a hexanes/EtOAc gradient gave the pure product as a tan oil. Yield=200 mg (0.52 mmol, ~quant.).

Step 5: (±)-{4-[6-Amino-5-(p-chlorophenyl)-4-pyrimidinyl]-1H-pyrazol-1-yl}phenylacetamide (8)

This compound was prepared according to the method reported for example 1, step 5 using the following reagents: 6-chloro-5-(p-chlorophenyl)-4-pyrimidinylamine (example 1, step 4, 120 mg, 0.5 mmol), (±)-phenyl[4-(4,4,5,5-tetramethyl-1,3,2-dioxaborolan-2-yl)-1H-pyrazol-1-yl]acetamide (example 8, step 4, 170 mg, 0.52 mmol), 2:1 v/v Toluene/EtOH mixture (5 mL), 2M Na$_2$CO$_3$ aqueous (1.6 mL), Pd[Ph$_3$P]$_4$ (30 mg, 0.025 mmol). Purification by preparative TLC plate on silica-gel (20×20 cm), eluting with EtOAc/MeOH (95:5 v/v). Product is a white solid. Yield=20 mg (0.05 mmol, 10%). HPLC/MS (ESI) m/z 405.4 (M$^+$+H$^+$). Method 1 retention time=2.21 min.

Example 9. (±)-N,N-Dimethyl{4-[6-amino-5-(p-chlorophenyl)-4-pyrimidinyl]-1H-pyrazol-1-yl}phenylacetamide (9)

Step 1: (±)-N,N-Dimethyl(4-bromo-1H-pyrazol-1-yl)phenylacetamide

This compound was prepared according to the method reported for example 8, step 3 using the following reagents: (±)-(4-bromo-1H-pyrazol-1-yl)phenylacetic acid (example 8, step 2, 169 mg, 0.6 mmol), dimethylamine hydrochloride (98 mg, 1.2 mmol), DMF (3 mL), diisopropylethylamine (430 mL, 2.4 mmol) and HATU (297 mg, 0.78 mmol). The product was obtained as yellow solid. Yield=185 mg (0.6 mmol, quant.). HPLC/MS (ESI) m/z 310.5 ($M^+ + H^+$). Method 1 retention time=2.81 min.

Step 2: (±)-N,N-Dimethylphenyl[4-(4,4,5,5-tetramethyl-1,3,2-dioxaborolan-2-yl)-1H-pyrazol-1-yl]acetamide This compound was prepared according to the method reported for example 3, step 2 using the following reagents: (±)-N,N-dimethyl(4-bromo-1H-pyrazol-1-yl)phenylacetamide (example 9, step 1, 232 mg, 0.75 mmol), bis(pinacolato)diboron (478 mg, 1.88 mmol), KOAc (166 mg, 1.69 mmol), 1,4-dioxane (7 mL) and Pd(dppf)Cl$_2$·CH$_2$Cl$_2$ (31 mg, 0.038 mmol). Purification by silica-gel chromatography eluting with a hexanes/EtOAc gradient gave the pure product as a yellow oil. Yield=138 mg (0.39 mmol, 52%). HPLC/MS (ESI) m/z 356.6 ($M^+ + H^+$). Method 1 retention time=2.80 min.

Step 3: (±)-N,N-Dimethyl{4-[6-amino-5-(p-chlorophenyl)-4-pyrimidinyl]-1H-pyrazol-1-yl}phenylacetamide (9)

This compound was prepared according to the method reported for example 1, step 5 using the following reagents: 6-chloro-5-(p-chlorophenyl)-4-pyrimidinylamine (example 1, step 4, 93 mg, 0.389 mmol), (±)-N,N-dimethylphenyl[4-(4,4,5,5-tetramethyl-1,3,2-dioxaborolan-2-yl)-1H-pyrazol-1-yl]acetamide (example 9, step 2, 138 mg, 0.389 mmol), 2:1 v/v Toluene/EtOH mixture (4 mL), 2M Na$_2$CO$_3$ aqueous (1.3 mL), Pd[Ph$_3$P]$_4$ (22 mg, 0.0195 mmol). Purification by preparative TLC plate on silica-gel (20×20 cm), eluting with EtOAc. Product is a white solid. Yield=9 mg (0.02 mmol, 5%). HPLC/MS (ESI) m/z 433.1 ($M^+ + H^+$). Method 1 retention time=2.38 min.

Example 10. 5-(p-Chlorophenyl)-6-(1-phenyl-1H-pyrazol-4-yl)-4-pyrimidinylamine (10)

Step 1: 4,4,5,5-Tetramethyl-2-(1-phenyl-1H-pyrazol-4-yl)-1,3,2-dioxaborolane

This compound was prepared according to the method reported for example 3, step 2 using the following reagents: 4-bromo-1-phenyl-1H-pyrazole (1.0 g, 4.48 mmol), bis(pinacolato)diboron (2.85 g, 11.20 mmol), KOAc (1.1 g, 11.20 mmol), 1,4-dioxane (8.8 mL) and Pd(dppf)Cl$_2$·CH$_2$Cl$_2$ (36 mg, 0.045 mmol). Purification by silica-gel chromatography eluting with a hexanes/EtOAc gradient gave the pure product as an oil. Yield=550 mg (2.04 mmol, 45%).

Step 2: 5-(p-Chlorophenyl)-6-(1-phenyl-1H-pyrazol-4-yl)-4-pyrimidinylamine (10)

This compound was prepared according to the method reported for example 1, step 5 using the following reagents: 6-chloro-5-(p-chlorophenyl)-4-pyrimidinylamine (example 1, step 4, 100 mg, 0.416 mmol), 4,4,5,5-tetramethyl-2-(1-phenyl-1H-pyrazol-4-yl)-1,3,2-dioxaborolane (example 10, step 1, 146 mg, 0.541 mmol), 1,4-dioxane (4 mL), Na$_2$CO$_3$ (132 mg, 1.25 mmol), H$_2$O (4 mL), Pd(dppf)Cl$_2$·CH$_2$Cl$_2$ (34 mg, 0.041 mmol). Purification by preparative TLC plate on silica-gel (20×20 cm), eluting with CH$_2$Cl$_2$/MeOH (94:6 v/v) mixture. Product is a white solid. Yield=25 mg (0.072 mmol, 17%). HPLC/MS (ESI) m/z 348.2 ($M^+ + H^+$). Method 1 retention time=2.53 min.

Example 11. 5-(p-Chlorophenyl)-6-[1-(o-tolyl)-1H-pyrazol-4-yl]-4-pyrimidinylamine (11)

Step 1: 4,4,5,5-Tetramethyl-2-[1-(o-tolyl)-1H-pyrazol-4-yl]-1,3,2-dioxaborolane

This compound was prepared according to the method reported for example 3, step 2 using the following reagents: 4-bromo-1-(o-tolyl)-1H-pyrazole (1.0 g, 4.22 mmol), bis(pinacolato)diboron (2.67 g, 10.54 mmol), KOAc (1.03 g, 10.33 mmol), 1,4-dioxane (8.4 mL) and Pd(dppf)Cl$_2$·CH$_2$Cl$_2$ (34 mg, 0.042 mmol). Purification by silica-gel chromatography eluting with a hexanes/EtOAc gradient gave the pure product as an oil. Yield=579 mg (2.04 mmol, 48%).

Step 2: 5-(p-Chlorophenyl)-6-[1-(o-tolyl)-1H-pyrazol-4-yl]-4-pyrimidinylamine (11)

This compound was prepared according to the method reported for example 1, step 5 using the following reagents: 6-chloro-5-(p-chlorophenyl)-4-pyrimidinylamine (example 1, step 4, 100 mg, 0.416 mmol), 4,4,5,5-tetramethyl-2-[1-(o-tolyl)-1H-pyrazol-4-yl]-1,3,2-dioxaborolane (example 11, step 1, 153 mg, 0.541 mmol), 1,4-dioxane (4 mL), Na$_2$CO$_3$ (132 mg, 1.25 mmol), H$_2$O (4 mL), Pd(dppf)Cl$_2$·CH$_2$Cl$_2$ (34 mg, 0.041 mmol). Purification by preparative TLC plate on silica-gel (20×20 cm), eluting with CH$_2$Cl$_2$/MeOH (94:6 v/v) mixture. Product is a white solid. Yield=30 mg (0.083 mmol, 20%). HPLC/MS (ESI) m/z 362.2 ($M^+ + H^+$). Method 1 retention time=2.53 min.

Example 12. 5-(p-Chlorophenyl)-6-[1-(m-chlorophenyl)-1H-pyrazol-4-yl]-4-pyrimidinylamine (12)

Step 1: 2-[1-(m-Chlorophenyl)-1H-pyrazol-4-yl]-4,4,5,5-tetramethyl-1,3,2-dioxaborolane This compound was prepared according to the method reported for example 3, step 2 using the following reagents: 4-bromo-1-(m-chlorophenyl)-1H-pyrazole (1.0 g, 3.88 mmol), bis(pinacolato)diboron (2.46 g, 9.71 mmol), KOAc (951 mg, 9.71 mmol), 1,4-dioxane (8 mL) and Pd(dppf)Cl$_2$·CH$_2$Cl$_2$ (32 mg, 0.038 mmol). Purification by silica-gel chromatography eluting with a hexanes/EtOAc gradient gave the pure product as an oil. Yield=620 mg (2.04 mmol, 53%).

Step 2: 5-(p-Chlorophenyl)-6-[1-(m-chlorophenyl)-1H-pyrazol-4-yl]-4-pyrimidinylamine (12)

This compound was prepared according to the method reported for example 1, step 5 using the following reagents: 6-chloro-5-(p-chlorophenyl)-4-pyrimidinylamine (example 1, step 4, 100 mg, 0.416 mmol), 2-[1-(m-chlorophenyl)-1H-pyrazol-4-yl]-4,4,5,5-tetramethyl-1,3,2-dioxaborolane (example 12, step 1, 164 mg, 0.541 mmol), 1,4-dioxane (4 mL), $Na_2CO_3$ (132 mg, 1.25 mmol), $H_2O$ (4 mL), Pd(dppf)$Cl_2 \cdot CH_2Cl_2$ (34 mg, 0.041 mmol). Purification by preparative TLC plate on silica-gel (20×20 cm), eluting with $CH_2Cl_2$/MeOH (94:6 v/v) mixture. Product is a white solid. Yield=79 mg (0.21 mmol, 50%). HPLC/MS (ESI) m/z 382.4 ($M^+ +H^+$). Method 1 retention time=2.82 min.

Example 13. 5-(p-Chlorophenyl)-6-{1-[m-(trifluoromethyl)phenyl]-1H-pyrazol-4-yl}-4-pyrimidinylamine (13)

Step 1: 4,4,5,5-Tetramethyl-2-{1-[m-(trifluoromethyl)phenyl]-1H-pyrazol-4-yl}-1,3,2-dioxaborolane This compound was prepared according to the method reported for example 3, step 2 using the following reagents: 4-bromo-1-[m-(trifluoromethyl)phenyl]-1H-pyrazole (1.0 g, 3.44 mmol), bis(pinacolato)diboron (2.18 g, 8.59 mmol), KOAc (841 mg, 8.59 mmol), 1,4-dioxane (8 mL) and Pd(dppf)$Cl_2 \cdot CH_2Cl_2$ (28 mg, 0.034 mmol). Purification by silica-gel chromatography eluting with a hexanes/EtOAc gradient gave the pure product as an oil. Yield=889 mg (2.63 mmol, 76%).

Step 2: 5-(p-Chlorophenyl)-6-{1-[m-(trifluoromethyl)phenyl]-1H-pyrazol-4-yl}-4-pyrimidinylamine (13)

This compound was prepared according to the method reported for example 1, step 5 using the following reagents: 6-chloro-5-(p-chlorophenyl)-4-pyrimidinylamine (example 1, step 4, 100 mg, 0.416 mmol), 4,4,5,5-tetramethyl-2-{1-[m-(trifluoromethyl)phenyl]-1H-pyrazol-4-yl}-1,3,2-dioxaborolane (example 13, step 1, 182 mg, 0.541 mmol), 1,4-dioxane (4 mL), $Na_2CO_3$ (132 mg, 1.25 mmol), $H_2O$ (4 mL), Pd(dppf)$Cl_2 \cdot CH_2Cl_2$ (34 mg, 0.041 mmol). Purification by preparative TLC plate on silica-gel (20×20 cm), eluting with $CH_2Cl_2$/MeOH (94:6 v/v) mixture. Product is a white solid. Yield=43 mg (0.104 mmol, 25%). HPLC/MS (ESI) m/z 416.6 ($M^+ +H^+$). Method 1 retention time=2.82 min.

Example 14. 5-(p-Chlorophenyl)-6-[1-(tetrahydro-2H-pyran-2-yl)-1H-pyrazol-4-yl]-4-pyrimidinylamine (14)

This compound was prepared according to the method reported for example 1, step 5 using the following reagents: 6-chloro-5-(p-chlorophenyl)-4-pyrimidinylamine (example 1, step 4, 821 mg, 3.42 mmol), 1-(2-tetrahydropyranyl)-1H-pyrazole-4-boronic acid, pinacol ester (1.11 g, 4.00 mmol), 1,4-dioxane (11 mL), 2M $Na_2CO_3$ aqueous (5.2 mL), Pd[$Ph_3P$]$_4$ (395 mg, 0.342 mmol). Purification by silica-gel chromatography, eluting with a hexanes/EtOAc gradient. Product is a light yellow solid. Yield=800 mg (2.25 mmol, 65%). HPLC/MS (ESI) m/z 356.6 ($M^+ +H^+$). Method 1 retention time=2.08 min.

Example 15. 5-(p-Chlorophenyl)-6-{1-[(m-fluorophenyl)methyl]-1H-pyrazol-4-yl}-4-pyrimidinylamine (15)

Step 1: 5-(p-Chlorophenyl)-6-(1H-pyrazol-4-yl)-4-pyrimidinylamine

A solution of 5-(p-chlorophenyl)-6-[1-(tetrahydro-2H-pyran-2-yl)-1H-pyrazol-4-yl]-4-pyrimidinylamine (example 14, 771 mg, 2.16 mmol) in $CH_2Cl_2$ (11 mL) was treated with trifluoroacetic acid (11 mL) at room temperature. After overnight stirring, the volatiles were removed in vacuo and the crude was dissolved in EtOAC (50 mL), washed with saturated $NaHCO_3$ aqueous and brine. The organics were dried over anhydrous $MgSO_4$, filtered and evaporated. The crude product was obtained as a yellow foam and was used in the next step without further purification. Yield=828 mg (>100%). HPLC/MS (ESI) m/z 272.4 ($M^+ +H^+$). Method 1 retention time=1.32 min.

Step 2: 5-(p-Chlorophenyl)-6-{1-[(m-fluorophenyl)methyl]-1H-pyrazol-4-yl}-4-pyrimidinylamine (15)

A stirring suspension containing 5-(p-chlorophenyl)-6-(1H-pyrazol-4-yl)-4-pyrimidinylamine (example 15, step 1, 68 mg, 0.25 mg) and $K_2CO_3$ (104 mg, 0.75 mmol) in DMF (2.5 mL) was treated with 3-fluorobenzyl bromide (57 mg, 0.30 mmol). The resulting mixture was kept at room temperature for 1 hour and then heated to 70° C. for 2 hours. The reaction was cooled to room temperature, diluted with EtOAc (50 mL), treated with $H_2O$ and transferred to a separatory funnel. The organic layer was separated, washed with 1N HCl aqueous and brine. The organics were dried over anhydrous $MgSO_4$, filtered and evaporated. Purification by preparative TLC plate on silica-gel (20×20 cm), eluting with EtOAc. Yield=8 mg (0.02 mmol, 8%). HPLC/MS (ESI) m/z 380.4 ($M^+ +H^+$). Method 1 retention time=2.23 min.

Example 16. 5-(p-Chlorophenyl)-6-{1-[(p-chlorophenyl)methyl]-1H-pyrazol-4-yl}-4-pyrimidinylamine (16)

This compound was prepared according to the method reported for example 15, step 2 using the following reagents: 5-(p-chlorophenyl)-6-(1H-pyrazol-4-yl)-4-pyrimidinylamine (example 15, step 1, 101 mg, 0.37 mg), $K_2CO_3$ (153 mg, 1.11 mmol), DMF (3.7 mL), 4-chlorobenzyl bromide (115 mg, 0.56 mmol). Yield=11 mg (0.028 mmol, 8%). HPLC/MS (ESI) m/z 396.4 ($M^+ +H^+$). Method 1 retention time=2.41 min.

Example 17. 5-(p-Chlorophenyl)-6-(1-{[o-(trifluoromethyl)phenyl]methyl}-1H-pyrazol-4-yl)-4-pyrimidinylamine (17)

This compound was prepared according to the method reported for example 15, step 2 using the following reagents: 5-(p-chlorophenyl)-6-(1H-pyrazol-4-yl)-4-pyrimidinylamine (example 15, step 1, 101 mg, 0.37 mg), $K_2CO_3$ (153 mg, 1.11 mmol), DMF (3.7 mL), 2-trifluoromethylbenzyl bromide (134 mg, 0.56 mmol). Yield=35 mg (0.081 mmol, 22%). HPLC/MS (ESI) m/z 430.4 ($M^+ +H^+$). Method 1 retention time=2.44 min.

Example 18. 5-(p-Chlorophenyl)-6-{1-[(p-fluorophenyl)methyl]-1H-pyrazol-4-yl}-4-pyrimidinylamine (18)

This compound was prepared according to the method reported for example 15, step 2 using the following reagents: 5-(p-chlorophenyl)-6-(1H-pyrazol-4-yl)-4-pyrimidinylamine (example 15, step 1, 101 mg, 0.37 mg), $K_2CO_3$ (153 mg, 1.11 mmol), DMF (3.7 mL), 4-fluorobenzyl bromide (70 mL, 0.56 mmol). Yield=22 mg (0.058 mmol, 16%). HPLC/MS (ESI) m/z 380.5 (M$^+$+H$^+$). Method 1 retention time=2.56 min.

Example 19. 5-(p-Chlorophenyl)-6-{1-[(2,4-difluorophenyl)methyl]-1H-pyrazol-4-yl}-4-pyrimidinylamine (19)

This compound was prepared according to the method reported for example 15, step 2 using the following reagents: 5-(p-chlorophenyl)-6-(1H-pyrazol-4-yl)-4-pyrimidinylamine (example 15, step 1, 101 mg, 0.37 mg), K$_2$CO$_3$ (153 mg, 1.11 mmol), DMF (3.7 mL), 2,4-difluorobenzyl bromide (77 mL, 0.56 mmol). Yield=22 mg (0.055 mmol, 15%). HPLC/MS (ESI) m/z 398.5 (M$^+$+H$^+$). Method 1 retention time=2.34 min.

Example 20. 5-(p-Chlorophenyl)-6-{1-[(p-trifluoromethoxyphenyl)methyl]-1H-pyrazol-4-yl}-4-pyrimidinylamine (20)

This compound was prepared according to the method reported for example 15, step 2 using the following reagents: 5-(p-chlorophenyl)-6-(1H-pyrazol-4-yl)-4-pyrimidinylamine (example 15, step 1, 101 mg, 0.37 mg), K$_2$CO$_3$ (153 mg, 1.11 mmol), DMF (3.7 mL), 4-methoxybenzyl bromide (90 mL, 0.56 mmol). Yield=23 mg (0.052 mmol, 14%). HPLC/MS (ESI) m/z 446.6 (M$^+$+H$^+$). Method 1 retention time=2.52 min.

Example 21. 5-(p-Chlorophenyl)-6-{1-[(o-fluorophenyl)methyl]-1H-pyrazol-4-yl}-4-pyrimidinylamine (21)

This compound was prepared according to the method reported for example 15, step 2 using the following reagents: 5-(p-chlorophenyl)-6-(1H-pyrazol-4-yl)-4-pyrimidinylamine (example 15, step 1, 101 mg, 0.37 mg), K$_2$CO$_3$ (153 mg, 1.11 mmol), DMF (3.7 mL), 2-fluorobenzyl bromide (67 mL, 0.56 mmol). Yield=17 mg (0.045 mmol, 12%). HPLC/MS (ESI) m/z 380.5 (M$^+$+H$^+$). Method 1 retention time=2.49 min.

Example 22. {1-[6-Amino-5-(p-chlorophenyl)-4-pyrimidinyl]-1H-pyrazol-4-yl}phenylmethanone (22)

Step 1: Phenyl(1H-pyrazol-4-yl)methanone

A solution of 4-bromo-1H-pyrazole (1.91 g, 13.0 mmol) in anhydrous THF (52 mL), under N$_2$, was cooled to −78° C. with stirring. n-BuLi (14.6 mL of a 2.0M solution in hexanes, 29.3 mmol) was added dropwise via syringe. The resulting mixture was stirred for 1 hour at −78° C., then warmed to room temperature and stirred for 2 hours. The reaction mixture was cooled to −78° C. and treated with ethyl benzoate (2.44 g, 16.2 mmol) dropwise. This mixture was stirred overnight and allowed to reach room temperature. The reaction was quenched with addition of saturated aqueous NH$_4$Cl solution carefully. The product was extracted with EtOAc, the organic layer was separated, washed with 1N HCl aqueous and brine. The organics were dried over anhydrous MgSO$_4$, filtered and evaporated. The crude product was obtained as a light yellow semi-solid. Yield=3.4 g. This material was used in the next step without further purification.

Step 2: {1-[6-Amino-5-(p-chlorophenyl)-4-pyrimidinyl]-1H-pyrazol-4-yl}phenylmethanone (22)

6-Chloro-5-(p-chlorophenyl)-4-pyrimidinylamine (example 1, step 4, 690 mg, 2.90 mmol) and phenyl(1H-pyrazol-4-yl)methanone (example 22, step 1, 500 mg, 2.90 mmol) were dissolved in NMP (7 mL) and treated with diisopropylethylamine (750 mg, 5.8 mmol). The resulting solution was heated to 130° C. for 16 hours with stirring. The reaction was cooled and directly purified by reverse phase column chromatography (C-18, CH$_3$CN:H$_2$O, 15% to 75% of CH$_3$CN, modified with TFA) gradient gave the pure product as a light yellow solid. Yield=13 mg (0.035 mmol, 1%). HPLC/MS (ESI) m/z 376.1 (M$^+$+H$^+$). Method 1 retention time=2.65 min.

Example 23. 6-(4-Benzyl-1H-pyrazol-1-yl)-5-(p-chlorophenyl)-4-pyrimidinylamine (23)

Step 1: 6-(4-Bromo-1H-pyrazol-1-yl)-5-(p-chlorophenyl)-4-pyrimidinylamine

6-Chloro-5-(p-chlorophenyl)-4-pyrimidinylamine (example 1, step 4, 1.2 g, 5.0 mmol) and 4-bromo-1H-pyrazole (735 mg, 5.0 mmol) were dissolved in DMF (15 mL) and treated with Cs$_2$CO$_3$ (3.25 mg, 10.0 mmol). The resulting solution was heated to 80° C. for 16 hours with stirring. The reaction was quenched with addition of saturated aqueous NH$_4$Cl solution. The product was extracted with EtOAc, the organic layer was separated, washed with 1N HCl aqueous and brine. The organics were dried over anhydrous MgSO$_4$, filtered and evaporated. The crude product was obtained as an orange solid. Yield=4.0 g. This material was used in the next step without further purification. HPLC/MS (ESI) m/z 352.3 (M$^+$+H$^+$). Method 1 retention time=2.57 min.

Step 2: 6-(4-Benzyl-1H-pyrazol-1-yl)-5-(p-chlorophenyl)-4-pyrimidinylamine (23)

This compound was prepared according to the method reported for example 1, step 5 using the following reagents: 6-(4-bromo-1H-pyrazol-1-yl)-5-(p-chlorophenyl)-4-pyrimidinylamine (example 23, step 1, 350 mg, 1.0 mmol), 2-benzyl-4,4,5,5-tetramethyl-1,3,2-dioxaborolane (327 mg, 1.5 mmol), 1,4-dioxane (5 mL), 2M Na$_2$CO$_3$ aqueous (1.8 mL), Pd(dppf)Cl$_2$·CH$_2$Cl$_2$ (41 mg, 0.05 mmol). Purification by reverse phase column chromatography (C-18, CH$_3$CN: H$_2$O, 15% to 75% of CH$_3$CN, modified with TFA) gradient gave the pure product as a white solid. Yield=24 mg (0.066 mmol, 7%). HPLC/MS (ESI) m/z 362.1 (M$^+$+H$^+$). Method 1 retention time=2.80 min.

Example 24. 5-(p-Methoxyphenyl)-6-(1-{[p-(trifluoromethyl)phenyl]methyl}-1H-pyrazol-4-yl)-4-pyrimidinylamine (24)

Step 1: 4-(5-Bromo-6-chloro-4-pyrimidinyl)-1-{[p-(trifluoromethyl)phenyl]methyl}-1H-pyrazole This compound was prepared according to the method reported for example 1, step 5 using the following reagents: 5-bromo-4,6-dichloropyrimidine (273 mg, 1.2 mmol), 4,4,5,5-tetramethyl-2-(1-{[p-(trifluoromethyl)phenyl]methyl}-1H-pyrazol-4-yl)-1,3,2-dioxaborolane (example 4, step 2, 352 mg, 1.0 mmol), 1,4-dioxane (3.3 mL), 2M Na$_2$CO$_3$ aqueous solution (1.5 mL) and Pd[Ph$_3$P]$_4$ (116 mg, 0.1 mmol). Purification by silica-gel chromatography eluting with a hexanes/EtOAc gradient gave the pure product as a yellow oil. Yield=142 mg (0.34 mmol, 34%). HPLC/MS (ESI) m/z 417.2, 419.4 (M$^+$+H$^+$). Method 1 retention time=3.27 min.

Step 2: 5-Bromo-6-(1-{[p-(trifluoromethyl)phenyl]methyl}-1H-pyrazol-4-yl)-4-pyrimidinylamine A solution of 4-(5-bromo-6-chloro-4-pyrimidinyl)-1-{[p-(trifluoromethyl)phenyl]methyl}-1H-pyrazole (example 24, step 1, 142 mg, 0.34 mmol) in iPrOH (1.7 mL) was treated with aqueous NH$_4$OH solution (1.7 mL) and the resulting mixture was heated to 100° C. for 2 hours. The reaction mixture was cooled, diluted with H$_2$O and the product was extracted with EtOAc. The organic layer was separated, washed with 1N HCl aqueous and brine, dried over anhydrous MgSO$_4$, filtered and evaporated. The product was obtained as a white solid and used in the next step without further purification. Yield=123 mg (0.31 mmol, 91%). HPLC/MS (ESI) m/z 400.2 (M$^+$+H$^+$). Method 1 retention time=2.44 min.

Step 3: 5-(p-Methoxyphenyl)-6-(1-{[p-(trifluoromethyl)phenyl]methyl}-1H-pyrazol-4-yl)-4-pyrimidinylamine (24)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 60 mg, 0.152 mmol), 4-methoxyphenyl boronic acid (35 mg, 0.228 mmol), 1,4-dioxane (1.5 mL), 2M Na$_2$CO$_3$ aqueous solution (0.3 mL) and Pd[Ph$_3$P]$_4$ (18 mg, 0.0152 mmol). Purification by preparative TLC plate on silica-gel (20×20 cm), eluting with EtOAc. Yield=13 mg (0.03 mmol, 20%). HPLC/MS (ESI) m/z 426.5 (M$^+$+H$^+$). Method 1 retention time=2.41 min.

Example 25. 5-(p-Fluorophenyl)-6-(1-{[p-(trifluoromethyl)phenyl]methyl}-1H-pyrazol-4-yl)-4-pyrimidinylamine (25)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 60 mg, 0.152 mmol), 4-fluorophenyl boronic acid (32 mg, 0.228 mmol), 1,4-dioxane (1.5 mL), 2M Na$_2$CO$_3$ aqueous solution (0.3 mL) and Pd[Ph$_3$P]$_4$ (18 mg, 0.0152 mmol). Purification by preparative TLC plate on silica-gel (20×20 cm), eluting with EtOAc. Yield=18 mg (0.044 mmol, 29%). HPLC/MS (ESI) m/z 414.6 (M$^+$+H$^+$). Method 1 retention time=2.41 min.

Example 26. 5-[p-(Methylsulfonyl)phenyl]-6-(1-{[p-(trifluoromethyl)phenyl]methyl}-1H-pyrazol-4-yl)-4-pyrimidinylamine (26)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 4-methylsulfonylphenylboronic acid (76 mg, 0.38 mmol), 1,4-dioxane (1.3 mL), 2M Na$_2$CO$_3$ aqueous solution (0.44 mL) and Pd[Ph$_3$P]$_4$ (15 mg, 0.0127 mmol). Purification by silica gel chromatography, eluting with a hexanes/EtOAc gradient gave the product as a white solid. Yield=25 mg (0.053 mmol, 21%). HPLC/MS (ESI) m/z 474.4 (M$^+$+H$^+$). Method 1 retention time=2.26 min.

Example 27. 5-(4-Chloro-3-fluorophenyl)-6-(1-{[p-(trifluoromethyl)phenyl]methyl}-1H-pyrazol-4-yl)-4-pyrimidinylamine (27)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 3-fluoro-4-chlorophenylboronic acid (66 mg, 0.38 mmol), 1,4-dioxane (1.3 mL), 2M Na$_2$CO$_3$ aqueous solution (0.44 mL) and Pd[Ph$_3$P]$_4$ (15 mg, 0.0127 mmol). Purification by silica gel chromatography, eluting with a hexanes/EtOAc gradient gave the product as a white solid. Yield=33 mg (0.074 mmol, 29%). HPLC/MS (ESI) m/z 448.3 (M$^+$+H$^+$). Method 1 retention time=2.38 min.

Example 28. 5-(3,4-Dichlorophenyl)-6-(1-{[p-(trifluoromethyl)phenyl]methyl}-1H-pyrazol-4-yl)-4-pyrimidinylamine (28)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 3,4-dichlorophenylboronic acid (73 mg, 0.38 mmol), 1,4-dioxane (1.3 mL), 2M Na$_2$CO$_3$ aqueous solution (0.44 mL) and Pd[Ph$_3$P]$_4$ (15 mg, 0.0127 mmol). Purification by silica gel chromatography, eluting with a hexanes/EtOAc gradient gave the product as a white solid. Yield=38 mg (0.082 mmol, 32%). HPLC/MS (ESI) m/z 464.3 (M$^+$+H$^+$). Method 1 retention time=2.43 min.

Example 29. 5-(4-Chloro-3-methoxyphenyl)-6-(1-{[p-(trifluoromethyl)phenyl]methyl}-1H-pyrazol-4-yl)-4-pyrimidinylamine (29)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 3-methoxy-4-chlorophenylboronic acid (71 mg, 0.38 mmol), 1,4-dioxane (1.3 mL), 2M Na$_2$CO$_3$ aqueous solution (0.44 mL) and Pd[Ph$_3$P]$_4$ (15 mg, 0.0127 mmol). Purification by silica gel chromatography, eluting with a hexanes/EtOAc gradient gave the product as a white solid. Yield=72 mg (0.157 mmol, 62%). HPLC/MS (ESI) m/z 460.5 (M$^+$+H$^+$). Method 1 retention time=2.37 min.

Example 30. 5-(3-Chloro-4-methoxyphenyl)-6-(1-{[p-(trifluoromethyl)phenyl]methyl}-1H-pyrazol-4-yl)-4-pyrimidinylamine (30)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 4-methoxy-3-chlorophenylboronic acid (71 mg, 0.38 mmol), 1,4-dioxane (1.3 mL), 2M Na$_2$CO$_3$ aqueous solution (0.44 mL) and Pd[Ph$_3$P]$_4$ (15 mg, 0.0127 mmol). Purification by silica gel chromatography, eluting with a hexanes/EtOAc gradient gave the product as a white solid. Yield=42 mg (0.092 mmol, 36%). HPLC/MS (ESI) m/z 460.4 (M$^+$+H$^+$). Method 1 retention time=2.31 min.

Example 31. 5-(3,4-Difluorophenyl)-6-(1-{[p-(trifluoromethyl)phenyl]methyl}-1H-pyrazol-4-yl)-4-pyrimidinylamine (31)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 3,4-difluorophenylboronic acid (60 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=65 mg (0.151 mmol, 60%). HPLC/MS (ESI) m/z 432.4 ($M^+ + H^+$). Method 1 retention time=2.28 min.

Example 32. 5-(3-Fluoro-4-methoxyphenyl)-6-(1-{[p-(trifluoromethyl)phenyl]methyl}-1H-pyrazol-4-yl)-4-pyrimidinylamine (32)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 4-methoxy-3-fluorophenylboronic acid (65 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=39 mg (0.088 mmol, 35%). HPLC/MS (ESI) m/z 444.7 ($M^+ + H^+$). Method 1 retention time=2.23 min.

Example 33. 5-(4-Fluoro-3-methoxyphenyl)-6-(1-{[p-(trifluoromethyl)phenyl]methyl}-1H-pyrazol-4-yl)-4-pyrimidinylamine (33)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 3-methoxy-4-fluorophenylboronic acid (65 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=38 mg (0.086 mmol, 34%). HPLC/MS (ESI) m/z 444.5 ($M^+ + H^+$). Method 1 retention time=2.28 min.

Example 34. 5-(p-Trifluoromethoxyphenyl)-6-(1-{[p-(trifluoromethyl)phenyl]methyl}-1H-pyrazol-4-yl)-4-pyrimidinylamine (34)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 4-trifluoromethoxyphenylboronic acid (78 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=59 mg (0.123 mmol, 49%). HPLC/MS (ESI) m/z 480.2 ($M^+ + H^+$). Method 1 retention time=2.46 min.

Example 35. 5-(2,2-Difluoro-2H-1,3-benzodioxol-5-yl)-6-(1-{[p-(trifluoromethyl)phenyl]methyl}-1H-pyrazol-4-yl)-4-pyrimidinylamine (35)

Step 1: 2-(2,2-Difluoro-2H-1,3-benzodioxol-5-yl)-4,4,5,5-tetramethyl-1,3,2-dioxaborolane This compound was prepared according to the method reported for example 3, step 2 using the following reagents: 5-bromo-2,2-difluoro-2H-1,3-benzodioxole (236 mg, 1.0 mmol), bis(pinacolato)diboron (762 mg, 3.0 mmol), KOAc (294 mg, 3.0 mmol), 1,4-dioxane (5 mL), Pd(dppf)$Cl_2 \cdot CH_2Cl_2$ (82 mg, 0.1 mmol). Purification by silica gel chromatography, eluting with a hexanes/EtOAc gradient gave the product as a yellow oil. Yield=260 mg (0.92 mmol, 92%). HPLC/MS (ESI) m/z 285.5 ($M^+ + H^+$). Method 1 retention time=3.32 min.

Step 2: This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 2-(2,2-difluoro-2H-1,3-benzodioxol-5-yl)-4,4,5,5-tetramethyl-1,3,2-dioxaborolane (example 35, step 1, 108 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=66 mg (0.139 mmol, 55%). HPLC/MS (ESI) m/z 476.3 ($M^+ + H^+$). Method 1 retention time=2.41 min.

Example 36. 4-(1-{[p-(Trifluoromethyl)phenyl]methyl}-1H-pyrazol-4-yl)-2-pyridylamine (36)

This compound was prepared according to the method reported for example 1, step 5 using the following reagents: 4-chloro-2-pyridylamine (129 mg, 1.0 mmol), 4,4,5,5-tetramethyl-2-(1-{[p-(trifluoromethyl)phenyl]methyl}-1H-pyrazol-4-yl)-1,3,2-dioxaborolane (example 4, step 2, 528 mg, 1.5 mmol), 1,4-dioxane (5 mL), 2M $Na_2CO_3$ aqueous solution (1.75 mL) and $Pd[Ph_3P]_4$ (58 mg, 0.05 mmol). Purification by silica gel chromatography, eluting with a hexanes/EtOAc gradient gave the product as a white solid. Yield=43 mg (0.137 mmol, 14%). HPLC/MS (ESI) m/z 319.3 ($M^+ + H^+$). Method 1 retention time=2.12 min.

Example 37. 5-Chloro-4-(1-{[p-(trifluoromethyl)phenyl]methyl}-1H-pyrazol-4-yl)-2-pyridylamine (37)

This compound was prepared according to the method reported for example 1, step 5 using the following reagents: 4,5-dichloro-2-pyridylamine (815 mg, 5.0 mmol), 4,4,5,5-tetramethyl-2-(1-{[p-(trifluoromethyl)phenyl]methyl}-1H-pyrazol-4-yl)-1,3,2-dioxaborolane (example 4, step 2, 2.64 g, 7.5 mmol), 1,4-dioxane (25 mL), 2M $Na_2CO_3$ aqueous solution (8.8 mL) and $Pd[Ph_3P]_4$ (289 mg, 0.25 mmol). Purification by silica gel chromatography, eluting with a hexanes/EtOAc gradient gave the product as a beige solid. Yield=1.13 g (3.21 mmol, 64%). HPLC/MS (ESI) m/z 353.3 ($M^+ + H^+$). Method 1 retention time=2.21 min.

Example 38. 3-(p-Methoxyphenyl)-4-(1-{[p-(trifluoromethyl)phenyl]methyl}-1H-pyrazol-4-yl)-2-pyridylamine (38)

Step 1:
4-Chloro-3-(p-methoxyphenyl)-2-pyridylamine

This compound was prepared according to the method reported for example 1, step 5 using the following reagents:

3-bromo-4-chloro-2-pyridylamine (208 mg, 1.0 mmol), 4-methoxyphenyl boronic acid (167 mg, 1.1 mmol), 1,4-dioxane (5 mL), 2M $Na_2CO_3$ aqueous solution (1.75 mL) and $Pd[Ph_3P]_4$ (58 mg, 0.05 mmol). Purification by silica gel chromatography, eluting with a hexanes/EtOAc gradient gave the product as a white solid. Yield=176 mg (0.75 mmol, 75%). HPLC/MS (ESI) m/z 235.3 ($M^+$+$H^+$). Method 1 retention time=1.74 min.

Step 2: -(p-Methoxyphenyl)-4-(1-{[p-(trifluoromethyl)phenyl]methyl}-1H-pyrazol-4-yl)-2-pyridylamine (38)

This compound was prepared according to the method reported for example 1, step 5 using the following reagents: 4-chloro-3-(p-methoxyphenyl)-2-pyridylamine (example 38, step 1, 70 mg, 0.3 mmol), 4,4,5,5-tetramethyl-2-(1-{[p-(trifluoromethyl)phenyl]methyl}-1H-pyrazol-4-yl)-1,3,2-dioxaborolane (example 4, step 2, 158 mg, 0.45 mmol), 1,4-dioxane (1.5 mL), 2M $Na_2CO_3$ aqueous solution (0.53 mL) and $Pd[Ph_3P]_4$ (17 mg, 0.015 mmol). Purification by silica gel chromatography, eluting with a hexanes/EtOAc gradient gave the product as a film. Yield=11 mg (0.026 mmol, 9%). HPLC/MS (ESI) m/z 425.3 ($M^+$+$H^+$). Method 1 retention time=2.30 min.

Example 39. 3-(p-Chlorophenyl)-4-(1-{[p-(trifluoromethyl)phenyl]methyl}-1H-pyrazol-4-yl)-2-pyridylamine (39)

Step 1: 4-Chloro-3-(p-chlorophenyl)-2-pyridylamine

This compound was prepared according to the method reported for example 1, step 5 using the following reagents: 3-bromo-4-chloro-2-pyridylamine (208 mg, 1.0 mmol), 4-chlorophenyl boronic acid (172 mg, 1.1 mmol), 1,4-dioxane (5 mL), 2M $Na_2CO_3$ aqueous solution (1.75 mL) and $Pd[Ph_3P]_4$ (58 mg, 0.05 mmol). Purification by silica gel chromatography, eluting with a hexanes/EtOAc gradient gave the product as a white solid. Yield=167 mg (0.70 mmol, 70%). HPLC/MS (ESI) m/z 239.2 ($M^+$+$H^+$). Method 1 retention time=1.93 min.

Step 2: 3-(p-Chlorophenyl)-4-(1-{[p-(trifluoromethyl)phenyl]methyl}-1H-pyrazol-4-yl)-2-pyridylamine (39)

This compound was prepared according to the method reported for example 1, step 5 using the following reagents: 4-chloro-3-(p-chlorophenyl)-2-pyridylamine (example 39, step 1, 167 mg, 0.7 mmol), 4,4,5,5-tetramethyl-2-(1-{[p-(trifluoromethyl)phenyl]methyl}-1H-pyrazol-4-yl)-1,3,2-dioxaborolane (example 4, step 2, 370 mg, 1.05 mmol), 1,4-dioxane (3.5 mL), 2M $Na_2CO_3$ aqueous solution (1.23 mL) and $Pd[Ph_3P]_4$ (40 mg, 0.035 mmol). Purification by silica gel chromatography, eluting with a hexanes/EtOAc gradient gave the product as a white solid. Yield=21 mg (0.049 mmol, 7%). HPLC/MS (ESI) m/z 429.2 ($M^+$+$H^+$). Method 1 retention time=2.37 min.

Example 40. 5-(4-Chloro-3-fluorophenyl)-6-(1-{[p-(trifluoromethyl)phenyl]methyl}-1H-pyrazol-4-yl)-4-pyrimidinylamine (40)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 4-chloro-3-fluorophenylboronic acid (66 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=33 mg (0.074 mmol, 29%). HPLC/MS (ESI) m/z 448.3 ($M^+$+$H^+$). Method 1 retention time=2.38 min.

Example 41. 5-(3-Fluoro-4-methoxyphenyl)-6-(1-{[p-(trifluoromethyl)phenyl]methyl}-1H-pyrazol-4-yl)-4-pyrimidinylamine (41)

This compound was prepared according to the method reported for example 1, step 5 using the following reagents: 5-bromo-6-(1-{[p-(trifluoromethyl)phenyl]methyl}-1H-pyrazol-4-yl)-4-pyrimidinylamine (example 24, step 2, 100 mg, 0.253 mmol), 3-fluoro-4-methoxyphenylboronic acid (65 mg, 0.38 mmol), 1,4-dioxane (1.3 mL), 2M $Na_2CO_3$ aqueous solution (0.44 mL) and $Pd[Ph_3P]_4$ (15 mg, 0.0127 mmol). Purification by silica gel chromatography, eluting with a hexanes/EtOAc gradient gave the product as a white solid. Yield=39 mg (0.088 mmol, 35%). HPLC/MS (ESI) m/z 444.7 ($M^+$+$H^+$). Method 1 retention time=2.23 min.

Example 42. 5-(1H-Pyrazol-4-yl)-6-(1-{[p-(trifluoromethyl)phenyl]methyl}-1H-pyrazol-4-yl)-4-pyrimidinylamine (42)

Step 1: 6-Chloro-5-iodo-4-pyrimidinylamine

A mixture of 4,6-dichloro-5-iodopyrimidine 1 (1.28 g, 4.67 mmol) and ammonia solution (1.92 mL of a 7 N solution in MeOH, 13.4 mmol) in EtOH (15 mL) was stirred for 24 hours at 60° C. The crude mixture was cooled to room temperature and evaporated under reduced pressure. The resulting yellow solid was treated with MeOH (6.0 mL) and the precipitate was filtered to give the corresponding product (1.09 g, 4.27 mmol, 91%) as a light-yellow solid. HPLC/MS (ESI) m/z 256.4 ($M^+$+$H^+$). Method 1 retention time=1.84 min.

Step 2: 6-Chloro-5-(2H-pyrazol-4-yl)-4-pyrimidinylamine

A mixture of 6-chloro-5-iodo-4-pyrimidinylamine (example 42, step 1, 510 mg, 2.00 mmol), 4,4,5,5-tetramethyl-2-(2H-pyrazol-4-yl)-1,3,2-dioxaborolane (495 mg, 2.55 mmol), $PdCl_2(PPh_3)_2$ (70 mg, 0.10 mmol, 5.0 mol %) and 2 M aqueous $Na_2CO_3$ (3.5 mL, 7.00 mmol) in 1,4-dioxane (6.00 mL) was stirred for 22 hr at 80° C. under a nitrogen atmosphere. The mixture was cooled to room temperature and then extracted with EtOAc. The organic layer was washed with brine, dried over $MgSO_4$ and concentrated to give the crude product. The product was purified by C-18, reverse phase column chromatography ($CH_3CN$:$H_2O$; 3% of $CH_3CN$ for 1 min., 3% to 10% for 20 min., 10% for 5 min.) to provide the corresponding product (163 mg, 0.83 mmol, 42%) as a white solid. HPLC/MS (ESI) m/z 196.6 ($M^+$+$H^+$). Method 1 retention time=0.31 min.

Step 3: 4,4,5,5-Tetramethyl-2-(1-{[p-(trifluoromethyl)phenyl]methyl}-1H-pyrazol-4-yl)-1,3,2-dioxaborolane A mixture of 4,4,5,5-tetramethyl-2-(1H-pyrazol-4-yl)-1,3,2-dioxaborolane (2.6 g, 13.4 mmol), p-(bromomethyl)

(trifluoromethyl)benzene (3.2 g, 13.4 mmol) and $K_2CO_3$ (4.63 g, 33.5 mmol) in DMF (25 mL) was stirred for 20 hours at 23° C. The crude mixture was filtered to remove inorganics. The filtrate was treated with $H_2O$ and then extracted with EtOAc. The organic layer was washed with brine, dried over $MgSO_4$ and concentrated to give the corresponding product (4.70 g, 13.3 mmol, 99%) as a light yellow oil. This material was used for next reaction without further purification. HPLC/MS (ESI) m/z 353.4 ($M^+ + H^+$). Method 1 retention time=2.78 min.

Step 4: 5-(1H-Pyrazol-4-yl)-6-(1-{[p-(trifluoromethyl)phenyl]methyl}-1H-pyrazol-4-yl)-4-pyrimidinylamine (42)

This compound was prepared according to the method reported for example 1, step 5 using the following reagents: 6-chloro-5-(2H-pyrazol-4-yl)-4-pyrimidinylamine (example 42, step 2, 163 mg, 0.83 mmol), 4,4,5,5-tetramethyl-2-(1-{[p-(trifluoromethyl)phenyl]methyl}-1H-pyrazol-4-yl)-1,3,2-dioxaborolane (example 42, step 3, 352 mg, 1.00 mmol), 1,4-dioxane (4.0 mL), 2M $Na_2CO_3$ aqueous solution (2.25 mL) and $Pd[Ph_3P]_4$ (48 mg, 0.04 mmol). Purification by The product was purified by C-18 reverse phase column chromatography ($CH_3CN:H_2O$; 10% of $CH_3CN$ for 1 min., 10% to 50% for 30 min.) to provide the corresponding product (140 mg, 0.36 mmol, 43%) as a white solid. HPLC/MS (ESI) m/z 386.3 ($M^+ + H^+$). Method 2 retention time=2.06 min.

Examples 43 and 44. N-[5-(p-Chlorophenyl)-6-(1-{[p-(trifluoromethyl)phenyl]methyl}-1H-pyrazol-4-yl)-4-pyrimidinyl]acetamide (43) and N-Acetyl-N-[5-(p-chlorophenyl)-6-(1-{[p-(trifluoromethyl)phenyl]methyl}-1H-pyrazol-4-yl)-4-pyrimidinyl]acetamide (44)

A stirring suspension of 5-(p-chlorophenyl)-6-(1-{[p-(trifluoromethyl)phenyl]methyl}-1H-pyrazol-4-yl)-4-pyrimidinylamine (example 4, 150 mg, 0.35 mmol) in $CH_2Cl_2$ (2 mL) was treated with diisopropylethylamine (188 μL, 1.05 mmol) and (4-dimethylamino)pyridine (4 mg, 0.035 mmol) under an inert atmosphere of $N_2$. Acetic anhydride (72 μL, 0.77 mol) was added and the resulting mixture was stirred at room temperature for 48 hours. The reaction mixture was concentrated in vacuo and purified directly by preparative TLC plate on silica-gel (20×20 cm), eluting with ethyl acetate. The fast-running spot corresponds to example 44 (113 mg, 0.22 mmol, 63%) and the slow running spot corresponds to example 43 (18 mg, 0.04 mmol, 11%). Example 43: HPLC/MS (ESI) m/z 472.5 ($M^+ + H^+$). Method 1 retention time=2.73 min. Example 44: HPLC/MS (ESI) m/z 514.6 ($M^+ + H^+$). Method 1 retention time=2.85 min.

Example 45. (Methylsulfonyl)[5-(p-chlorophenyl)-6-(1-{[p-(trifluoromethyl)phenyl]methyl}-1H-pyrazol-4-yl)-4-pyrimidinyl]amine (45)

A stirring solution of 5-(p-chlorophenyl)-6-(1-{[p-(trifluoromethyl)phenyl]methyl}-1H-pyrazol-4-yl)-4-pyrimidinylamine (example 4, 150 mg, 0.35 mmol) in THF (1.8 mL) under an inert atmosphere of $N_2$ was treated with sodium hydride (56 mg of a 60% dispersion in oil, 1.40 mmol) and the resulting mixture was stirred for 30 minutes at room temperature. Methanesulfonyl chloride (41 μL, 0.53 mmol) was added via syringe and the resulting mixture was stirred at room temperature for 2 hours. The reaction was carefully poured onto ice/water and the product was extracted with ethyl acetate. The organic layer was washed with 1 N aqueous HCl solution and brine, dried over anhydrous MgSO4, filtered and evaporated. The crude product was purified by silica-gel column chromatography, eluting with hexanes/EtOAc mixture to provide the title compound as a white solid (63 mg, 0.124 mmol, 35%). HPLC/MS (ESI) m/z 508.3 ($M^+ + H^+$). Method 1 retention time=2.70 min.

Examples 46 and 47. N,N-Dimethyl[5-(p-chlorophenyl)-6-(1-{[p-(trifluoromethyl)phenyl]methyl}-1H-pyrazol-4-yl)-4-pyrimidinyl]amine (46) and N-Methyl[5-(p-chlorophenyl)-6-(1-{[p-(trifluoromethyl)phenyl]methyl}-1H-pyrazol-4-yl)-4-pyrimidinyl]amine (47)

A stirring solution of 5-(p-chlorophenyl)-6-(1-{[p-(trifluoromethyl)phenyl]methyl}-1H-pyrazol-4-yl)-4-pyrimidinylamine (example 4, 150 mg, 0.35 mmol) in THF (1.8 mL) under an inert atmosphere of $N_2$ was treated with sodium hydride (56 mg of a 60% dispersion in oil, 1.40 mmol) and the resulting mixture was stirred for 30 minutes at room temperature. Methyl iodide (26 μL, 0.42 mmol) was added via syringe and the resulting mixture was stirred at room temperature for 2 hours. The reaction was carefully poured onto ice/water and the product was extracted with ethyl acetate. The organic layer was washed with 1 N aqueous HCl solution and brine, dried over anhydrous MgSO4, filtered and evaporated. The crude product was purified by silica-gel column chromatography, eluting with hexanes/EtOAc mixture. The fast-running spot corresponds to example 46 (115 mg, 0.25 mmol, 72%) and the slow running spot corresponds to example 47 (12 mg, 0.03 mmol, 8%). Example 46: HPLC/MS (ESI) m/z 458.3 ($M^+ + H^+$). Method 1 retention time=2.64 min. Example 47: HPLC/MS (ESI) m/z 444.6 ($M^+ + H^+$). Method 1 retention time=2.58 min.

Example 48. S6K Enzymatic Inhibition Assay

Enzymatic activity was determined using a commercial HotSpot kinase assay. Recombinant human p70S6K kinase was purchased from ThermoFisher Scientific (cat #PV3815). The substrate S6K/RSK2 peptide 2 was synthesized at Genscript [Piscataway, NJ]. In brief, the substrate was prepared in the reaction buffer [20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO]. Testing compounds were dissolved in 100% DMSO and a serial dilution was conducted in DMSO. The kinase at final concentration of 3 nM was added into the substrate solution and gently mixed. Test compounds were delivered at the appropriate concentrations into the kinase reaction mixture by Echo550, and incubated for 20 minutes at room temperature. $^{33}$P-ATP (Specific activity 10 μCi/μL) was added into the reaction mixture to initiate the reaction. Assay plates were incubated for 2 hours at room temperature. The radioactivity was detected by filter-binding method. Kinase activity data is expressed as the percent remaining kinase activity in test samples compared to vehicle (DMSO) reactions. $IC_{50}$ curves were plotted and $IC_{50}$ values were calculated using the GraphPad Prism 4 program based on a sigmoidal dose-response equation.

Example 49. Cell-Based S6K Inhibition Assay

The functional activity of compounds was determined in a cell line where p70S6K is constitutively activated. Test article was dissolved in DMSO to make a 10 μM stock.

PathScan® Phospho-S6 Ribosomal Protein (Ser235/236) Sandwich ELISA Kit was purchased from Cell Signaling Technology. A549 lung cancer cell line, was purchased from American Type Culture Collection. A549 cells were grown in F-12K Medium supplemented with 10% FBS. 100 µg/mL penicillin and 100 µg/mL streptomycin were added to the culture media. Cultures were maintained at 37° C. in a humidified atmosphere of 5% $CO_2$ and 95% air. $2.0 \times 10^5$ cells were seeded in each well of 12-well tissue culture plates for overnight. Cells were treated with DMSO or test article (starting at 100 µM, 10-dose with 3 fold dilution) for 3 hours. The cells were washed once with ice cold PBS and lysed with 1× cell lysis buffer. Cell lysates were collected and samples were added to the appropriate wells of the ELISA plate. Plate was incubated for overnight at 4° C. 100 µL of reconstituted Phospho-S6 Ribosomal Protein (Ser235/236) Detection Antibody was added to each well and the plate was incubated at 37° C. for 1 hour. Wells were washed and 100 µl of reconstituted HRP-Linked secondary antibody was added to each well. The plate was incubated for 30 minutes at 37° C. Wash procedure was repeated and 100 µL of TMB Substrate was added to each well. The plate was incubated for 10 minutes at 37° C. 100 µL of STOP Solution was added to each well and the absorbance was read at 460 nm using Envision 2104 Multilabel Reader (PerkinElmer, Santa Clara, CA). $IC_{50}$ curves were plotted and $IC_{50}$ values were calculated using the GraphPad Prism 4 program based on a sigmoidal dose-response equation.

TABLE 2

In vitro biological data for representative compounds of Formula I-IX Unless otherwise noted, compounds that were tested had an $IC_{50}$ of less than 50 µM in the S6K binding assay.

| Example Number | S6K Binding Activity |
| --- | --- |
| 1 | A |
| 2 | B |
| 3 | B |
| 4 | A |
| 5 | A |
| 6 | A |
| 7 | A |
| 8 | A |
| 9 | B |
| 10 | B |
| 11 | B |
| 12 | C |
| 13 | C |
| 14 | C |
| 15 | A |
| 16 | A |
| 17 | B |
| 18 | A |
| 19 | A |
| 20 | A |
| 21 | A |
| 22 | C |
| 23 | B |
| 24 | A |
| 25 | A |
| 26 | C |
| 27 | A |
| 28 | C |
| 29 | C |
| 30 | C |
| 31 | A |
| 32 | A |
| 33 | C |
| 34 | C |
| 35 | C |
| 36 | C |
| 37 | C |
| 38 | A |
| 39 | A |
| 40 | A |
| 41 | A |

Unless otherwise noted, compounds that were tested had an $IC_{50}$ of less than 50 µM in the S6K Binding assay. A=less than 0.05 µM; B=greater than 0.05 µM and less than 0.5 µM; C=greater than 0.5 µM and less than 10 µM;

CITATIONS

Hardie, G. and Hanks, S. (1995) The Protein Kinase Facts Book. I and II, Academic Press, San Diego, CA Magnuson B, Ekim B, Fingar D C. (2012). Regulation and function of ribosomal protein S6 kinase (S6K) within mTOR signalling networks. Biochem J. 441(1):1-21.

Khotskaya Y B, Goverdhan A, Shen J, Ponz-Sarvise M, Chang S S, Hsu M C, Wei Y, Xia W, Yu D, Hung M C. (2014). S6K1 promotes invasiveness of breast cancer cells in a model of metastasis of triple-negative breast cancer. Am J Transl Res. 6(4):361-376.

Akar U, Ozpolat B, Mehta K, Lopez-Berestein G, Zhang D, Ueno N T, Hortobagyi G N, Arun B. (2010). Targeting p70S6K prevented lung metastasis in a breast cancer xenograft model. Mol Cancer Ther. 9(5):1180-1187.

Ip C K, Cheung A N, Ngan H Y, Wong A S. (2011). p70 S6 kinase in the control of actin cytoskeleton dynamics and directed migration of ovarian cancer cells. Oncogene. 30(21):2420-2432.

Hwahng S H, Ki S H, Bae E J, Kim H E, Kim S G. (2009). Role of adenosine monophosphate-activated protein kinase-p70 ribosomal S6 kinase-1 pathway in repression of liver X receptor-alpha-dependent lipogenic gene induction and hepatic steatosis by a novel class of dithiolethiones. Hepatology. 49(6):1913-1925.

Gäbele E, Reif S, Tsukada S, Bataller R, Yata Y, Morris T, Schrum L W, Brenner D A, Rippe R A. (2005). The role of p70S6K in hepatic stellate cell collagen gene expression and cell proliferation. J Biol Chem. 280(14):13374-13382.

Bae E J, Xu J, Oh D Y, Bandyopadhyay G, Lagakos W S, Keshwani M, Olefsky J M (2012). Liver-specific p70 S6 kinase depletion protects against hepatic steatosis and systemic insulin resistance. J Biol Chem. 287(22):18769-80.

Ehninger D, Silva A J. (2011). Rapamycin for treating Tuberous sclerosis and Autism spectrum disorders. Trends Mol Med. 17(2):78-87.

Bhattacharya A, Kaphzan H, Alvarez-Dieppa A C, Murphy J P, Pierre P, Klann E (2012). Genetic removal of p70 S6 kinase 1 corrects molecular, synaptic, and behavioral phenotypes in fragile X syndrome mice. Neuron 76(2): 325-37.

Bhattacharya A, Mamcarz M, Mullins C, Choudhury A, Boyle R G, Smith D G, Walker D W, Klann E. (2015). Targeting Translation Control with p70 S6 Kinase 1 Inhibitors to Reverse Phenotypes in Fragile X Syndrome Mice. Neuropsychopharmacology. doi: 10.1038/npp.2015.369

What is claimed is:

1. A compound of Formula I having the structure:

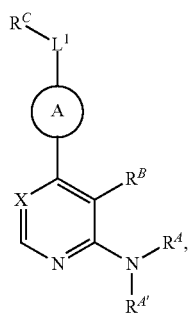

or a salt thereof, wherein X is =N— or a carbon atom that is substituted or unsubstituted;

$R^A$ is —H, —CN, $C_1$-$C_4$ alkyl, $C_1$-$C_4$ fluoroalkyl, —C(O)$R^D$ or —$SO_2R^D$;

$R^{A'}$ is —H, $C_1$-$C_4$alkyl, $C_1$-$C_4$ fluoroalkyl, or —C(O)$R^D$;

$R^B$ is substituted phenyl or $C_5$-$C_6$ heteroaryl (Ar, or HetAr), either of which is unsubstituted or substituted by up to three $R^E$ independently of one another;

$L^1$ is a bond, or a $C_1$-$C_4$ unbranched alkylene, a $C_3$-$C_6$ cycloalkylene or a 3-6-membered heterocycloalkylene, either one of which is unsubstituted or substituted by one or two $R^F$ independently of one another and/or having one, two or three of its —$CH_2$— groups independently replaced by —O—, —NH—, or —CO— or, $L^1$ is a $C_3$-$C_7$ branched alkylene, which is unsubstituted or substituted by one or two $R^F$ independently of one another, and/or having one, two or three of its —$CH_2$— groups independently replaced by —O—, —NH—, or —CO— and/or having one of its —CH— groups replaced by —N—;

$R^C$ is a $C_6$ or $C_{10}$ aryl or $C_5$-$C_{10}$ heteroaryl, either of which is unsubstituted or substituted by up to three $R^G$ independently of one another, Ring A is a pyrazole moiety having the structure of:

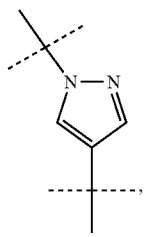

wherein the pyrazole moiety is unsubstituted or substituted with one or two $R^H$ substituents at its aromatic carbon atom(s), wherein each $R^H$, if present, is independently selected from the group consisting of a monovalent C-linked moiety, —OH, —CN, $C_1$-$C_4$ alkoxy, —O$C_1$-$C_4$ fluoroalkyl, $C_1$-$C_{20}$ alkyl, $C_3$-$C_6$ cycloalkyl, $C_1$-$C_4$ fluoroalkyl, and halogen;

$R^D$ is —H or an unsubstituted or substituted $C_1$-$C_4$ alkyl or an amino acid moiety;

each $R^E$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O) $C_1$-$C_4$alkyl, —$SO_2C_1$-$C_4$alkyl, —$NH_2$, —NH$C_1$-$C_4$ alkyl, —N($C_1$-$C_4$ alkyl)$_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCON$H_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —$SO_2C_1$-$C_4$alkyl, —N($C_1$-$C_4$ alkyl)$_2$, —CN, or at least two adjacent $R^E$ are present that taken together define a substituted or unsubstituted $C_5$-$C_6$ carbocycle or heterocycle, and the remaining $R^E$, if present, is as previously defined;

each $R^F$, if present, is independently selected from the group consisting of halogen, —OH, —CN, —$NH_2$, —$NMe_2$, —$CONH_2$, —CONHMe, —$CONMe_2$, —COOH, —$CH_3$ and —$CF_3$;

each $R^G$, if present, is independently selected from the group consisting of halogen, $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O) $C_1$-$C_4$alkyl, —$SO_2C_1$-$C_4$alkyl, —$NH_2$, —NH$C_1$-$C_4$ alkyl, —N($C_1$-$C_4$ alkyl)$_2$, —$NO_2$, —CN, —OCN, —COOH, —COO($C_1$-$C_4$ alkyl), —$CONH_2$, —CONH ($C_1$-$C_4$ alkyl), —CON($C_1$-$C_4$ alkyl)$_2$, —NHCO($C_1$-$C_4$ alkyl), —NHCONH($C_1$-$C_4$ alkyl), —NHCON$H_2$, —CHO and —CO($C_1$-$C_4$ alkyl), or is independently selected from the group consisting of halogen, $C_1$-$C_4$ alkyl, $C_3$-$C_6$ cycloalkyl, $C_1$-$C_4$ fluoroalkyl, $C_1$-$C_4$ alkoxy, $C_3$-$C_6$ cycloalkyloxy, —S$C_1$-$C_4$alkyl, —$SO_2C_1$-$C_4$alkyl, —N($C_1$-$C_4$ alkyl)$_2$, —CN, or at least two adjacent $R^G$ are present that taken together define a substituted or unsubstituted $C_5$-$C_6$ carbocycle or heterocycle, and the remaining $R^G$, if present, is as previously defined;

wherein the remaining aromatic carbon atom(s) of the pyrimidine or pyridine ring of formula I is unsubstituted or independently substituted by $R^J$; and wherein each $R^J$, if present is independently selected from the group consisting of $C_1$-$C_4$ alkyl, $C_3$-$C_6$ cycloalkyl, $C_1$-$C_4$ fluoroalkyl, —OH, —SH, $C_1$-$C_4$ alkoxy, $C_3$-$C_6$ cycloalkyloxy, —S$C_1$-$C_4$alkyl, —S(O)$C_1$-$C_4$alkyl, —$SO_2C_1$-$C_4$alkyl, —$NH_2$, —NH$C_1$-$C_4$ alkyl, —N($C_1$-$C_4$ alkyl)$_2$, and —CN, or is selected from the group consisting of $C_1$-$C_4$ alkyl, $C_1$-$C_4$ fluoroalkyl, $C_1$-$C_4$ alkoxy, halogen, —CN, —$NH_2$, and —OH.

2. The compound of claim 1 wherein the pyrazole moiety is unsubstituted.

3. The compound of claim 1 wherein $R^A$ is —H, X is =N— or =CH—.

4. The compound of claim 1 wherein $R^B$ is substituted phenyl.

5. The compound of claim 4 wherein $R^E$ in $R^B$ is absent or one or two of $R^E$ are present and are independently selected from the group consisting of halogen and $C_1$-$C_4$ alkoxy.

6. The compound of claim 5 wherein one and only one of $R^E$ in $R^B$ is present and is —Cl.

7. The compound of claim 6 wherein two of $R^E$ in $R^B$ are present and are independently selected from the group consisting of —F and —$OCH_3$.

8. The compound of claim 1 wherein $R^C$ is substituted or unsubstituted phenyl.

9. The compound of claim 8 wherein $R^G$ in $R^B$ is present and is -halogen or $C_1$-$C_4$ fluoroalkyl.

10. The compound of claim 9 wherein $R^G$ is —CF$_3$.

11. The compound of claim 1 wherein $L^1$ is —CH($R^F$)—.

12. The compound of claim 11 wherein $R^F$ is replaced by —H or is —CH$_2$NH$_2$.

13. The compound of claim 1 having the structure of Formula VIII:

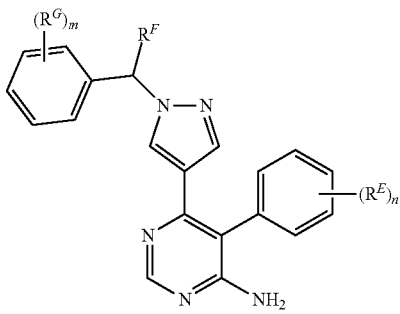

VIII or a salt thereof, wherein
each $R^E$, if present, is independently selected from the group consisting of halogen and C$_1$-C$_4$ alkoxy;
subscript n is 0, 1 or 2;
$R^F$ is replaced by —H or is —CH$_2$NH$_2$;
each $R^G$, if present, is independently selected from the group consisting of halogen and C$_1$-C$_4$ fluoroalkyl; and
subscript m is 0, 1 or 2.

14. The compound of claim 1 having the structure of Formula IX:

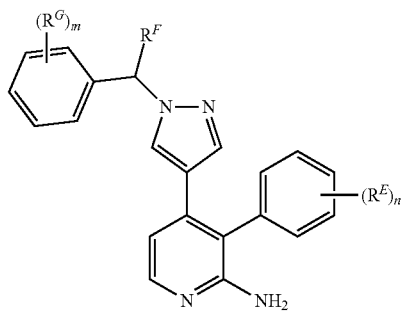

IX wherein $R^E$ if present, is independently selected from the group consisting of halogen and C$_1$-C$_4$ alkoxy;
subscript n is 0, 1 or 2;
$R^F$ is replaced by hydrogen or is —CH$_2$NH$_2$
each $R^G$, if present, is independently selected from the group consisting of halogen and C$_1$-C$_4$ fluoroalkyl; and
subscript m is 0, 1 or 2.

15. The compound of claim 1 wherein the compound is selected from the group consisting of:
  6-(1-Benzyl-1H-pyrazol-4-yl)-5-(p-chlorophenyl)-4-pyrimidinylamine,
  5-(p-Chlorophenyl)-6-(1-methyl-1H-pyrazol-4-yl)-4-pyrimidinylamine,
  5-(p-Chlorophenyl)-6-(1-{1-[m-(trifluoromethyl)phenyl]ethyl}-1H-pyrazol-4-yl)-4-pyrimidinylamine,
  5-(p-Chlorophenyl)-6-(1-{[p-(trifluoromethyl)phenyl]methyl}-1H-pyrazol-4-yl)-4-pyrimidinylamine,
  (R,S)-2-{4-[6-Amino-5-(p-chlorophenyl)-4-pyrimidinyl]-1H-pyrazol-1-yl}-2-phenylethanol,
  (R,S)-6-[1-(2-Amino-1-phenylethyl)-1H-pyrazol-4-yl]-5-(p-chlorophenyl)-4-pyrimidinamine,
  5-(p-Chlorophenyl)-6-[1-(1-phenylethenyl)-1H-pyrazol-4-yl]-4-pyrimidinylamine,
  (R,S)-{4-[6-Amino-5-(p-chlorophenyl)-4-pyrimidinyl]-1H-pyrazol-1-yl}-phenylacetamide,
  (R,S)—N,N-Dimethyl{4-[6-amino-5-(p-chlorophenyl)-4-pyrimidinyl]-1H-pyrazol-1-yl}phenylacetamide,
  5-(p-Chlorophenyl)-6-(1-phenyl-1H-pyrazol-4-yl)-4-pyrimidinylamine,
  5-(p-Chlorophenyl)-6-[1-(o-tolyl)-1H-pyrazol-4-yl]-4-pyrimidinylamine,
  5-(p-Chlorophenyl)-6-[1-(m-chlorophenyl)-1H-pyrazol-4-yl]-4-pyrimidinylamine,
  5-(p-Chlorophenyl)-6-{1-[m-(trifluoromethyl)phenyl]-1H-pyrazol-4-yl}-4-pyrimidinylamine,
  5-(p-Chlorophenyl)-6-[1-(tetrahydro-2H-pyran-2-yl)-1H-pyrazol-4-yl]-4-pyrimidinylamine,
  5-(p-Chlorophenyl)-6-{1-[(m-fluorophenyl)methyl]-1H-pyrazol-4-yl}-4-pyrimidinylamine,
  5-(p-Chlorophenyl)-6-{1-[(p-chlorophenyl)methyl]-1H-pyrazol-4-yl}-4-pyrimidinylamine,
  5-(p-Chlorophenyl)-6-(1-{[o-(trifluoromethyl)phenyl]methyl}-1H-pyrazol-4-yl)-4-pyrimidinylamine,
  5-(p-Chlorophenyl)-6-{1-[(p-fluorophenyl)methyl]-1H-pyrazol-4-yl}-4-pyrimidinylamine,
  5-(p-Chlorophenyl)-6-{1-[(2,4-difluorophenyl)methyl]-1H-pyrazol-4-yl}-4-pyrimidinylamine,
  5-(p-Chlorophenyl)-6-{1-[(p-trifluoromethoxyphenyl)methyl]-1H-pyrazol-4-yl}-4-pyrimidinylamine,
  5-(p-Chlorophenyl)-6-{1-[(o-fluorophenyl)methyl]-1H-pyrazol-4-yl}-4-pyrimidinylamine,
  {1-[6-Amino-5-(p-chlorophenyl)-4-pyrimidinyl]-1H-pyrazol-4-yl}phenylmethanone,
  6-(4-Benzyl-1H-pyrazol-1-yl)-5-(p-chlorophenyl)-4-pyrimidinylamine,
  5-(p-Methoxyphenyl)-6-(1-{[p-(trifluoromethyl)phenyl]methyl}-1H-pyrazol-4-yl)-4-pyrimidinylamine,
  5-(p-Fluorophenyl)-6-(1-{[p-(trifluoromethyl)phenyl]methyl}-1H-pyrazol-4-yl)-4-pyrimidinylamine,
  5-[p-(Methylsulfonyl)phenyl]-6-(1-{[p-(trifluoromethyl)phenyl]methyl}-1H-pyrazol-4-yl)-4-pyrimidinylamine,
  5-(4-Chloro-3-fluorophenyl)-6-(1-{[p-(trifluoromethyl)phenyl]methyl}-1H-pyrazol-4-yl)-4-pyrimidinylamine,
  5-(3,4-Dichlorophenyl)-6-(1-{[p-(trifluoromethyl)phenyl]methyl}-1H-pyrazol-4-yl)-4-pyrimidinylamine,
  5-(4-Chloro-3-methoxyphenyl)-6-(1-{[p-(trifluoromethyl)phenyl]methyl}-1H-pyrazol-4-yl)-4-pyrimidinylamine,
  5-(3-Chloro-4-methoxyphenyl)-6-(1-{[p-(trifluoromethyl)phenyl]methyl}-1H-pyrazol-4-yl)-4-pyrimidinylamine,
  5-(3,4-Difluorophenyl)-6-(1-{[p-(trifluoromethyl)phenyl]methyl}-1H-pyrazol-4-yl)-4-pyrimidinylamine,
  5-(3-Fluoro-4-methoxyphenyl)-6-(1-{[p-(trifluoromethyl)phenyl]methyl}-1H-pyrazol-4-yl)-4-pyrimidinylamine,
  5-(4-Fluoro-3-methoxyphenyl)-6-(1-{[p-(trifluoromethyl)phenyl]methyl}-1H-pyrazol-4-yl)-4-pyrimidinylamine,
  5-(p-Trifluoromethoxyphenyl)-6-(1-{[p-(trifluoromethyl)phenyl]methyl}-1H-pyrazol-4-yl)-4-pyrimidinylamine, 5-(2,2-Difluoro-2H-1,3-benzodioxol-5-yl)-6-(1-{[p-(trifluoromethyl)phenyl]methyl}-1H-pyrazol-4-yl)-4-pyrimidinylamine,
4-(1-{[p-(Trifluoromethyl)phenyl]methyl}-1H-pyrazol-4-yl)-2-pyridylamine,
5-Chloro-4-(1-{[p-(trifluoromethyl)phenyl]methyl}-1H-pyrazol-4-yl)-2-pyridylamine,
3-(p-Methoxyphenyl)-4-(1-{[p-(trifluoromethyl)phenyl]methyl}-1H-pyrazol-4-yl)-2-pyridylamine,
3-(p-Chlorophenyl)-4-(1-{[p-(trifluoromethyl)phenyl]methyl}-1H-pyrazol-4-yl)-2-pyridylamine,
5-(4-Chloro-3-fluorophenyl)-6-(1-{[p-(trifluoromethyl)phenyl]methyl}-1H-pyrazol-4-yl)-4-pyrimidinylamine,
5-(3-Fluoro-4-methoxyphenyl)-6-(1-{[p-(trifluoromethyl)phenyl]methyl}-1H-pyrazol-4-yl)-4-pyrimidinylamine,
5-(1H-Pyrazol-4-yl)-6-(1-{[p-(trifluoromethyl)phenyl]methyl}-1H-pyrazol-4-yl)-4-pyrimidinylamine,
N-[5-(p-Chlorophenyl)-6-(1-{[p-(trifluoromethyl)phenyl]methyl}-1H-pyrazol-4-yl)-4-pyrimidinyl]acetamide,
N-Acetyl-N-[5-(p-chlorophenyl)-6-(1-{[p-(trifluoromethyl)phenyl]methyl}-1H-pyrazol-4-yl)-4-pyrimidinyl]acetamide,
(Methylsulfonyl)[5-(p-chlorophenyl)-6-(1-{[p-(trifluoromethyl)phenyl]methyl}-1H-pyrazol-4-yl)-4-pyrimidinyl]amine,
N,N-Dimethyl[5-(p-chlorophenyl)-6-(1-{[p-(trifluoromethyl)phenyl]methyl}-1H-pyrazol-4-yl)-4-pyrimidinyl]amine,
N-Methyl[5-(p-chlorophenyl)-6-(1-{[p-(trifluoromethyl)phenyl]methyl}-1H-pyrazol-4-yl)-4-pyrimidinyl]amine,
6-(1-Benzyl-3-methyl-1H-pyrazol-4-yl)-5-(p-chlorophenyl)-4-pyrimidinylamine,
5-(p-Chlorophenyl)-6-(3-methyl-1-{[p-(trifluoromethyl)phenyl]methyl}-1H-pyrazol-4-yl)-4-pyrimidinylamine,
6-[1-(2-Amino-1-phenylethyl)-3-methyl-1H-pyrazol-4-yl]-5-(p-chlorophenyl)-4-pyrimidinamine,
6-(1-{2-Amino-1-[p-(trifluoromethyl)phenyl]ethyl}-3-methyl-1H-pyrazol-4-yl)-5-(p-chlorophenyl)-4-pyrimidinamine,
4-(1-Benzyl-3-methyl-1H-pyrazol-4-yl)-3-(p-chlorophenyl)-2-pyridylamine,
3-(p-Chlorophenyl)-4-(3-methyl-1-{[p-(trifluoromethyl)phenyl]methyl}-1H-pyrazol-4-yl)-2-pyridylamine,
4-[1-(2-Amino-1-phenylethyl)-3-methyl-H-pyrazol-4-yl]-3-(p-chlorophenyl)-2-pyridinamine,
4-(1-{2-Amino-1-[p-(trifluoromethyl)phenyl]ethyl}-3-methyl-1H-pyrazol-4-yl)-3-(p-chlorophenyl)-2-pyridinamine,
6-(1-Benzyl-3,5-dimethyl-1H-pyrazol-4-yl)-5-(p-chlorophenyl)-4-pyrimidinylamine,
5-(p-Chlorophenyl)-6-(3,5-dimethyl-1-{[p-(trifluoromethyl)phenyl]methyl}-1H-pyrazol-4-yl)-4-pyrimidinylamine,
6-[1-(2-Amino-1-phenylethyl)-3,5-dimethyl-1H-pyrazol-4-yl]-5-(p-chlorophenyl)-4-pyrimidinamine,
6-(1-{2-Amino-1-[p-(trifluoromethyl)phenyl]ethyl}-3,5-dimethyl-1H-pyrazol-4-yl)-5-(p-chlorophenyl)-4-pyrimidinamine,
4-(1-Benzyl-3,5-dimethyl-1H-pyrazol-4-yl)-3-(p-chlorophenyl)-2-pyridylamine,
3-(p-Chlorophenyl)-4-(3,5-dimethyl-1-{[p-(trifluoromethyl)phenyl]methyl}-1H-pyrazol-4-yl)-2-pyridylamine,
4-[1-(2-Amino-1-phenylethyl)-3,5-dimethyl-1H-pyrazol-4-yl]-3-(p-chlorophenyl)-2-pyridinamine,
4-(1-{2-Amino-1-[p-(trifluoromethyl)phenyl]ethyl}-3,5-dimethyl-1H-pyrazol-4-yl)-3-(p-chlorophenyl)-2-pyridinamine,
{4-[6-Amino-5-(p-chlorophenyl)-4-pyrimidinyl]-1-benzyl-1H-pyrazol-3-yl}methanol,
{4-[6-Amino-5-(p-chlorophenyl)-4-pyrimidinyl]-1-{[p-(trifluoromethyl)phenyl]methyl}-1H-pyrazol-3-yl}methanol,
{4-[6-Amino-5-(p-chlorophenyl)-4-pyrimidinyl]-1-(2-amino-1-phenylethyl)-1H-pyrazol-3-yl}methanol,
{4-[6-Amino-5-(p-chlorophenyl)-4-pyrimidinyl]-1-{2-amino-1-[p-(trifluoromethyl)-phenyl]ethyl}-1H-pyrazol-3-yl}methanol,
{4-[2-Amino-3-(p-chlorophenyl)-4-pyridyl]-1-benzyl-1H-pyrazol-3-yl}methanol,
{4-[2-Amino-3-(p-chlorophenyl)-4-pyridyl]-1-{[p-(trifluoromethyl)phenyl]methyl}-1H-pyrazol-3-yl}methanol,
{4-[2-Amino-3-(p-chlorophenyl)-4-pyridyl]-1-(2-amino-1-phenylethyl)-1H-pyrazol-3-yl}methanol,
{4-[2-Amino-3-(p-chlorophenyl)-4-pyridyl]-1-{2-amino-1-[p-(trifluoromethyl)phenyl]-ethyl}-1H-pyrazol-3-yl}methanol,
6-(1-Benzyl-3-fluoro-1H-pyrazol-4-yl)-5-(p-chlorophenyl)-4-pyrimidinylamine,
5-(p-Chlorophenyl)-6-(3-fluoro-1-{[p-(trifluoromethyl)phenyl]methyl}-1H-pyrazol-4-yl)-4-pyrimidinylamine,
6-[1-(2-Amino-1-phenylethyl)-3-fluoro-1H-pyrazol-4-yl]-5-(p-chlorophenyl)-4-pyrimidinamine,
6-(1-{2-Amino-1-[p-(trifluoromethyl)phenyl]ethyl}-3-fluoro-1H-pyrazol-4-yl)-5-(p-chlorophenyl)-4-pyrimidinamine,
4-(1-Benzyl-3-fluoro-1H-pyrazol-4-yl)-3-(p-chlorophenyl)-2-pyridylamine,
3-(p-Chlorophenyl)-4-(3-fluoro-1-{[p-(trifluoromethyl)phenyl]methyl}-1H-pyrazol-4-yl)-2-pyridylamine,
4-[1-(2-Amino-1-phenylethyl)-3-fluoro-1H-pyrazol-4-yl]-3-(p-chlorophenyl)-2-pyridinamine,
4-(1-{2-Amino-1-[p-(trifluoromethyl)phenyl]ethyl}-3-fluoro-1H-pyrazol-4-yl)-3-(p-chlorophenyl)-2-pyridinamine,
6-[1-Benzyl-3-(trifluoromethyl)-1H-pyrazol-4-yl]-5-(p-chlorophenyl)-4-pyrimidinylamine,
5-(p-Chlorophenyl)-6-[3-(trifluoromethyl)-1-{[p-(trifluoromethyl)phenyl]methyl}-1H-pyrazol-4-yl]-4-pyrimidinylamine,
6-[1-(2-Amino-1-phenylethyl)-3-(trifluoromethyl)-1H-pyrazol-4-yl]-5-(p-chlorophenyl)-4-pyrimidinamine,
6-(1-{2-Amino-1-[p-(trifluoromethyl)phenyl]ethyl}-3-(trifluoromethyl)-1H-pyrazol-4-yl)-5-(p-chlorophenyl)-4-pyrimidinamine,
4-[1-Benzyl-3-(trifluoromethyl)-1H-pyrazol-4-yl]-3-(p-chlorophenyl)-2-pyridylamine,
3-(p-Chlorophenyl)-4-[3-(trifluoromethyl)-1-{[p-(trifluoromethyl)phenyl]methyl}-1H-pyrazol-4-yl]-2-pyridylamine,
4-[1-(2-Amino-1-phenylethyl)-3-(trifluoromethyl)-1H-pyrazol-4-yl]-3-(p-chlorophenyl)-2-pyridinamine,
4-(1-{2-Amino-1-[p-(trifluoromethyl)phenyl]ethyl}-3-(trifluoromethyl)-1H-pyrazol-4-yl)-3-(p-chlorophenyl)-2-pyridinamine, (2S)-2-{4-[6-Amino-5-(p-chlorophenyl)-4-pyrimidinyl]-1H-pyrazol-1-yl}-2-phenylethanol,
(2R)-2-{4-[6-Amino-5-(p-chlorophenyl)-4-pyrimidinyl]-1H-pyrazol-1-yl}-2-phenylethanol,
(2S)-2-{4-[6-Amino-5-(p-chlorophenyl)-4-pyrimidinyl]-1H-pyrazol-1-yl}-2-[p-(trifluoromethyl)phenyl]ethanol,
(2R)-2-{4-[6-Amino-5-(p-chlorophenyl)-4-pyrimidinyl]-1H-pyrazol-1-yl}-2-[p-(trifluoromethyl)phenyl]ethanol,
(2S)-2-{4-[6-Amino-5-(p-chlorophenyl)-4-pyrimidinyl]-1H-pyrazol-1-yl}-2-phenylethanamine,
(2R)-2-{4-[6-Amino-5-(p-chlorophenyl)-4-pyrimidinyl]-1H-pyrazol-1-yl}-2-phenylethanamine,
(2S)-2-{4-[6-Amino-5-(p-chlorophenyl)-4-pyrimidinyl]-1H-pyrazol-1-yl}-2-[p-(trifluoromethyl)phenyl]ethanamine,
(2R)-2-{4-[6-Amino-5-(p-chlorophenyl)-4-pyrimidinyl]-1H-pyrazol-1-yl}-2-[p-(trifluoromethyl)phenyl]ethanamine,
(2S)-2-{4-[6-Amino-5-(p-chlorophenyl)-4-pyrimidinyl]-1H-pyrazol-1-yl}-1-(dimethylamino)-2-phenylethane,
(2R)-2-{4-[6-Amino-5-(p-chlorophenyl)-4-pyrimidinyl]-1H-pyrazol-1-yl}-1-(dimethylamino)-2-phenylethane,
(2S)-2-{4-[6-Amino-5-(p-chlorophenyl)-4-pyrimidinyl]-1H-pyrazol-1-yl}-1-(dimethylamino)-2-[p-(trifluoromethyl)phenyl]ethane,
(2R)-2-{4-[6-Amino-5-(p-chlorophenyl)-4-pyrimidinyl]-1H-pyrazol-1-yl}-1-(dimethylamino)-2-[p-(trifluoromethyl)phenyl]ethane,
(2S)-2-{4-[6-Amino-5-(1H-pyrazol-4-yl)-4-pyrimidinyl]-1H-pyrazol-1-yl}-1-(dimethylamino)-2-[p-(trifluoromethyl)phenyl]ethane,
(R)-2-{4-[6-Amino-5-(1H-pyrazol-4-yl)-4-pyrimidinyl]-1H-pyrazol-1-yl}-1-(dimethylamino)-2-[p-(trifluoromethyl)phenyl]ethane,
(2S)-{4-[6-Amino-5-(p-chlorophenyl)-4-pyrimidinyl]-1H-pyrazol-1-yl}[p-(trifluoromethyl)phenyl]acetic acid,
(2R)-{4-[6-Amino-5-(p-chlorophenyl)-4-pyrimidinyl]-1H-pyrazol-1-yl}[p-(trifluoromethyl)phenyl]acetic acid,
(2S)-{4-[6-Amino-5-(p-chlorophenyl)-4-pyrimidinyl]-1H-pyrazol-1-yl}[p-(trifluoromethyl)phenyl]acetamide,
(2R)-{4-[6-Amino-5-(p-chlorophenyl)-4-pyrimidinyl]-1H-pyrazol-1-yl}[p-(trifluoromethyl)phenyl]acetamide,
3-(1H-Pyrazol-4-yl)-4-(1-{[p-(trifluoromethyl)phenyl]methyl}-1H-pyrazol-4-yl)-2-pyridylamine,
(S)-2-{4-[2-Amino-3-(p-chlorophenyl)-4-pyridyl]-1H-pyrazol-1-yl}-2-[p-(trifluoromethyl)phenyl]ethanol,
(R)-2-{4-[2-Amino-3-(p-chlorophenyl)-4-pyridyl]-1H-pyrazol-1-yl}-2-[p-(trifluoromethyl)phenyl]ethanol,
4-(1-{(S)-2-Amino-1-[p-(trifluoromethyl)phenyl]ethyl}-1H-pyrazol-4-yl)-3-(p-chlorophenyl)-2-pyridinamine,
4-(1-{(R)-2-Amino-1-[p-(trifluoromethyl)phenyl]ethyl}-1H-pyrazol-4-yl)-3-(p-chlorophenyl)-2-pyridinamine,
4-(1-{(S)-2-(Dimethylamino)-1-[p-(trifluoromethyl)phenyl]ethyl}-1H-pyrazol-4-yl)-3-(p-chlorophenyl)-2-pyridinamine,
4-(1-{(R)-2-(Dimethylamino)-1-[p-(trifluoromethyl)phenyl]ethyl}-1H-pyrazol-4-yl)-3-(p-chlorophenyl)-2-pyridinamine,
(S)-{4-[2-Amino-3-(p-chlorophenyl)-4-pyridyl]-1H-pyrazol-1-yl}[p-(trifluoromethyl)phenyl]acetic acid,
(R)-{4-[2-Amino-3-(p-chlorophenyl)-4-pyridyl]-1H-pyrazol-1-yl}[p-(trifluoromethyl)phenyl]acetic acid,
(S)-{4-[2-Amino-3-(p-chlorophenyl)-4-pyridyl]-1H-pyrazol-1-yl}[p-(trifluoromethyl)phenyl]acetamide,
(R)-{4-[2-Amino-3-(p-chlorophenyl)-4-pyridyl]-1H-pyrazol-1-yl}[p-(trifluoromethyl)phenyl]acetamide,
and salts thereof.

16. The compound of claim 1 where the compound is selected from the group consisting of 6-(1-Benzyl-1H-pyrazol-4-yl)-5-(p-chlorophenyl)-4-pyrimidinylamine, 5-(p-Chlorophenyl)-6-(1-methyl-1H-pyrazol-4-yl)-4-pyrimidinylamine, 5-(p-Chlorophenyl)-6-(1-{1-[m-(trifluoromethyl)phenyl]ethyl}-1H-pyrazol-4-yl)-4-pyrimidinylamine, 5-(p-Chlorophenyl)-6-(1-{1[p-(trifluoromethyl)phenyl]methyl}-1H-pyrazol-4-yl)-4-pyrimidinylamine, (R,S)-2-{4-[6-Amino-5-(p-chlorophenyl)-4-pyrimidinyl]-1H-pyrazol-1-yl}-2-phenylethanol, (R,S)-6-[1-(2-Amino-1-phenylethyl)-1H-pyrazol-4-yl]-5-(p-chlorophenyl)-4-pyrimidinamine, 5-(p-Chlorophenyl)-6-[1-(1-phenylethenyl)-1H-pyrazol-4-yl]-4-pyrimidinylamine, (R,S)-{4-[6-Amino-5-(p-chlorophenyl)-4-pyrimidinyl]-1H-pyrazol-1-yl}phenylacetamide, (R,S)—N,N-Dimethyl{4-[6-amino-5-(p-chlorophenyl)-4-pyrimidinyl]-1H-pyrazol-1-yl}phenylacetamide, 5-(p-Chlorophenyl)-6-(1-phenyl-1H-pyrazol-4-yl)-4-pyrimidinylamine, 5-(p-Chlorophenyl)-6-[1-(o-tolyl)-1H-pyrazol-4-yl]-4-pyrimidinylamine, 5-(p-Chlorophenyl)-6-[1-(m-chlorophenyl)-1H-pyrazol-4-yl]-4-pyrimidinylamine, 5-(p-Chlorophenyl)-6-{1-[m-(trifluoromethyl)phenyl]-1H-pyrazol-4-yl}-4-pyrimidinylamine, 5-(p-Chlorophenyl)-6-[1-(tetrahydro-2H-pyran-2-yl)-1H-pyrazol-4-yl]-4-pyrimidinylamine, 5-(p-Chlorophenyl)-6-{1-[(m-fluorophenyl)methyl]-1H-pyrazol-4-yl}-4-pyrimidinylamine, 5-(p-Chlorophenyl)-6-{1-[(p-chlorophenyl)methyl]-1H-pyrazol-4-yl}-4-pyrimidinylamine, 5-(p-Chlorophenyl)-6-(1-{[o-(trifluoromethyl)phenyl]-methyl}-1H-pyrazol-4-yl)-4-pyrimidinylamine, 5-(p-Chlorophenyl)-6-{1-[(p-fluorophenyl)-methyl]-1H-pyrazol-4-yl}-4-pyrimidinylamine, 5-(p-Chlorophenyl)-6-{1-[(2,4-difluorophenyl)-methyl]-1H-pyrazol-4-yl}-4-pyrimidinylamine, 5-(p-Chlorophenyl)-6-{1-[(p-trifluoromethoxyphenyl)methyl]-1H-pyrazol-4-yl}-4-pyrimidinylamine, 5-(p-Chlorophenyl)-6-{1-[(o-fluorophenyl)methyl]-1H-pyrazol-4-yl}-4-pyrimidinylamine, {1-[6-Amino-5-(p-chlorophenyl)-4-pyrimidinyl]-1H-pyrazol-4-yl}phenylmethanone, 6-(4-Benzyl-1H-pyrazol-1-yl)-5-(p-chlorophenyl)-4-pyrimidinylamine, 5-(p-Methoxyphenyl)-6-(1-{[p-(trifluoromethyl)-phenyl]methyl}-1H-pyrazol-4-yl)-4-pyrimidinylamine, 5-(p-Fluorophenyl)-6-(1-{[p-(trifluoromethyl)phenyl]methyl}-1H-pyrazol-4-yl)-4-pyrimidinylamine, 5-[p-(Methylsulfonyl)-phenyl]-6-(1-{[p-(trifluoromethyl)phenyl]methyl}-1H-pyrazol-4-yl)-4-pyrimidinylamine, 5-(4-Chloro-3-fluorophenyl)-6-(1-{[p-(trifluoromethyl)phenyl]methyl}-1H-pyrazol-4-yl)-4-pyrimidinylamine, 5-(3,4-Dichlorophenyl)-6-(1-{[p-(trifluoromethyl)phenyl]methyl}-1H-pyrazol-4-yl)-4-pyrimidinylamine, 5-(4-Chloro-3-methoxyphenyl)-6-(1-{[p-(trifluoromethyl)-phenyl]methyl}-1H-pyrazol-4-yl)-4-pyrimidinylamine, 5-(3-Chloro-4-methoxyphenyl)-6-(1-{[p-(trifluoromethyl)phenyl]methyl}-1H-pyrazol-4-yl)-4-pyrimidinylamine, 5-(3,4-Difluorophenyl)-6-(1-{[p-(trifluoromethyl)phenyl]methyl}-1H-pyrazol-4-yl)-4-pyrimidinylamine, 5-(3-Fluoro-4-methoxyphenyl)-6-(1-{[p-(trifluoromethyl)phenyl]methyl}-1H-pyrazol-4-yl)-4-pyrimidinylamine, 5-(4-Fluoro-3-methoxyphenyl)-6-(1-{[p-(trifluoromethyl)phenyl]methyl}-1H-pyrazol-4-yl)-4- pyrimidinylamine, 5-(p-Trifluoromethoxyphenyl)-6-(1-{[p-(trifluoromethyl)phenyl]methyl}-1H-pyrazol-4-yl)-4-pyrimidinylamine, 5-(2,2-Difluoro-2H-1,3-benzodioxol-5-yl)-6-(1-{1[p-(trifluoromethyl)phenyl]methyl}-1H-pyrazol-4-yl)-4-pyrimidinylamine, 4-(1-{[p-(Trifluoromethyl)phenyl]methyl}-1H-pyrazol-4-yl)-2-pyridylamine, 5-Chloro-4-(1-{[p-(trifluoromethyl)phenyl]methyl}-1H-pyrazol-4-yl)-2-pyridylamine, 3-(p-Methoxyphenyl)-4-(1-{[p-(trifluoromethyl)phenyl]methyl}-1H-pyrazol-4-yl)-2-pyridylamine, 3-(p-Chlorophenyl)-4-(1-{1[p-(trifluoromethyl)phenyl]methyl}-1H-pyrazol-4-yl)-2-pyridylamine, 5-(4-Chloro-3-fluorophenyl)-6-(1-{1[p-(trifluoromethyl)phenyl]methyl}-1H-pyrazol-4-yl)-4-pyrimidinylamine, 5-(3-Fluoro-4-methoxyphenyl)-6-(1-{[p-(trifluoromethyl)phenyl]methyl}-1H-pyrazol-4-yl)-4-pyrimidinylamine, 5-(1H-Pyrazol-4-yl)-6-(1-{[p-(trifluoromethyl)phenyl]methyl}-1H-pyrazol-4-yl)-4-pyrimidinylamine, and salts thereof.

17. A pharmaceutically acceptable formulation comprising a compound of claim 1 and at least one pharmaceutically acceptable excipient.

18. The pharmaceutically acceptable formulation of claim 17, wherein the compound is selected from the group of claim 15.

19. The pharmaceutically acceptable formulation of claim 17, wherein the compound is 6-(1-Benzyl-1H-pyrazol-4-yl)-5-(p-chlorophenyl)-4-pyrimidinylamine, 5-(p-Chlorophenyl)-6-(1-methyl-1H-pyrazol-4-yl)-4-pyrimidinylamine, 5-(p-Chlorophenyl)-6-(1-{1-[m-(trifluoromethyl)phenyl]ethyl}-1H-pyrazol-4-yl)-4-pyrimidinylamine, 5-(p-Chlorophenyl)-6-(1-{1[p-(trifluoromethyl)phenyl]methyl}-1H-pyrazol-4-yl)-4-pyrimidinylamine, (R,S)-2-{4-[6-Amino-5-(p-chlorophenyl)-4-pyrimidinyl]-1H-pyrazol-1-yl}-2-phenylethanol, (R,S)-6-[1-(2-Amino-1-phenylethyl)-1H-pyrazol-4-yl]-5-(p-chlorophenyl)-4-pyrimidinamine, 5-(p-Chlorophenyl)-6-[1-(1-phenylethenyl)-1H-pyrazol-4-yl]-4-pyrimidinylamine, (R,S)-{4-[6-Amino-5-(p-chlorophenyl)-4-pyrimidinyl]-1H-pyrazol-1-yl}phenylacetamide, (R,S)—N,N-Dimethyl{4-[6-amino-5-(p-chlorophenyl)-4-pyrimidinyl]-1H-pyrazol-1-yl}phenylacetamide, 5-(p-Chlorophenyl)-6-(1-phenyl-1H-pyrazol-4-yl)-4-pyrimidinylamine, 5-(p-Chlorophenyl)-6-[1-(o-tolyl)-1H-pyrazol-4-yl]-4-pyrimidinylamine, 5-(p-Chlorophenyl)-6-[1-(m-chlorophenyl)-1H-pyrazol-4-yl]-4-pyrimidinylamine, 5-(p-Chlorophenyl)-6-{1-[m-(trifluoromethyl)phenyl]-1H-pyrazol-4-yl}-4-pyrimidinylamine, 5-(p-Chlorophenyl)-6-[1-(tetrahydro-2H-pyran-2-yl)-1H-pyrazol-4-yl]-4-pyrimidinylamine, 5-(p-Chlorophenyl)-6-{1-[(m-fluorophenyl)methyl]-1H-pyrazol-4-yl}-4-pyrimidinylamine, 5-(p-Chlorophenyl)-6-{1-[(p-chlorophenyl)methyl]-1H-pyrazol-4-yl}-4-pyrimidinylamine, 5-(p-Chlorophenyl)-6-(1-{[o-(trifluoromethyl)phenyl]methyl}-1H-pyrazol-4-yl)-4-pyrimidinylamine, 5-(p-Chlorophenyl)-6-{1-[(p-fluorophenyl)methyl]-1H-pyrazol-4-yl}-4-pyrimidinylamine, 5-(p-Chlorophenyl)-6-{1-[(2,4-difluorophenyl)methyl]-1H-pyrazol-4-yl}-4-pyrimidinylamine, 5-(p-Chlorophenyl)-6-{1-[(p-trifluoromethoxyphenyl)methyl]-1H-pyrazol-4-yl}-4-pyrimidinylamine, 5-(p-Chlorophenyl)-6-{1-[(o-fluorophenyl)methyl]-1H-pyrazol-4-yl}-4-pyrimidinylamine, {1-[6-Amino-5-(p-chlorophenyl)-4-pyrimidinyl]-1H-pyrazol-4-yl}phenylmethanone, 6-(4-Benzyl-1H-pyrazol-1-yl)-5-(p-chlorophenyl)-4-pyrimidinylamine, 5-(p-Methoxyphenyl)-6-(1-{[p-(trifluoromethyl)phenyl]methyl}-1H-pyrazol-4-yl)-4-pyrimidinylamine, 5-(p-Fluorophenyl)-6-(1-{[p-(trifluoromethyl)phenyl]methyl}-1H-pyrazol-4-yl)-4-pyrimidinylamine, 5-[p-(Methylsulfonyl)phenyl]-6-(1-1{[p-(trifluoromethyl)phenyl]methyl}-1H-pyrazol-4-yl)-4-pyrimidinylamine, 5-(4-Chloro-3-fluorophenyl)-6-(1-{[p-(trifluoromethyl)phenyl]methyl}-1H-pyrazol-4-yl)-4-pyrimidinylamine, 5-(3,4-Dichlorophenyl)-6-(1-{[p-(trifluoromethyl)phenyl]methyl}-1H-pyrazol-4-yl)-4-pyrimidinylamine, 5-(4-Chloro-3-methoxyphenyl)-6-(1-{[p-(trifluoromethyl)phenyl]methyl}-1H-pyrazol-4-yl)-4-pyrimidinylamine, 5-(3-Chloro-4-methoxyphenyl)-6-(1-{[p-(trifluoromethyl)phenyl]methyl}-1H-pyrazol-4-yl)-4-pyrimidinylamine, 5-(3,4-Difluorophenyl)-6-(1-{[p-(trifluoromethyl)phenyl]methyl}-1H-pyrazol-4-yl)-4-pyrimidinylamine, 5-(3-Fluoro-4-methoxyphenyl)-6-(1-{[p-(trifluoromethyl)phenyl]methyl}-1H-pyrazol-4-yl)-4-pyrimidinylamine, 5-(4-Fluoro-3-methoxyphenyl)-6-(1-{[p-(trifluoromethyl)phenyl]methyl}-1H-pyrazol-4-yl)-4-pyrimidinylamine, 5-(p-Trifluoromethoxyphenyl)-6-(1-{[p-(trifluoromethyl)phenyl]methyl}-1H-pyrazol-4-yl)-4-pyrimidinylamine, 5-(2,2-Difluoro-2H-1,3-benzodioxol-5-yl)-6-(1-{[p-(trifluoromethyl)phenyl]methyl}-1H-pyrazol-4-yl)-4-pyrimidinylamine, 4-(1-{[p-(Trifluoromethyl)phenyl]methyl}-1H-pyrazol-4-yl)-2-pyridylamine, 5-Chloro-4-(1-{[p-(trifluoromethyl)phenyl]methyl}-1H-pyrazol-4-yl)-2-pyridylamine, 3-(p-Methoxyphenyl)-4-(1-{[p-(trifluoromethyl)phenyl]methyl}-1H-pyrazol-4-yl)-2-pyridylamine, 3-(p-Chlorophenyl)-4-(1-{[p-(trifluoromethyl)phenyl]methyl}-1H-pyrazol-4-yl)-2-pyridylamine, 5-(4-Chloro-3-fluorophenyl)-6-(1-{[p-(trifluoromethyl)phenyl]methyl}-1H-pyrazol-4-yl)-4-pyrimidinylamine, 5-(3-Fluoro-4-methoxyphenyl)-6-(1-{[p-(trifluoromethyl)phenyl]methyl}-1H-pyrazol-4-yl)-4-pyrimidinylamine, 5-(1H-Pyrazol-4-yl)-6-(1-{[p-(trifluoromethyl)phenyl]methyl}-1H-pyrazol-4-yl)-4-pyrimidinylamine, and pharmaceutically acceptable salts thereof.

20. The compound of claim 1, wherein the compound is 5-(p-Chlorophenyl)-6-(1-{[p-(trifluoromethyl)phenyl]methyl}-1H-pyrazol-4-yl)-4-pyrimidinylamine.

21. The pharmaceutically acceptable formulation of claim 17, wherein the compound of claim 1 is 5-(p-Chlorophenyl)-6-(1-{[p-(trifluoromethyl)phenyl]methyl}-1H-pyrazol-4-yl)-4-pyrimidinylamine.

* * * * *